United States Patent
Fujiwara et al.

(10) Patent No.: US 11,448,961 B2
(45) Date of Patent: Sep. 20, 2022

(54) IODONIUM SALT, RESIST COMPOSITION, AND PATTERN FORMING PROCESS

(71) Applicant: Shin-Etsu Chemical Co., Ltd., Tokyo (JP)

(72) Inventors: Takayuki Fujiwara, Joetsu (JP); Masaki Ohashi, Joetsu (JP); Kazuhiro Katayama, Joetsu (JP); Kenji Yamada, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 343 days.

(21) Appl. No.: 16/561,456

(22) Filed: Sep. 5, 2019

(65) Prior Publication Data

US 2020/0081341 A1    Mar. 12, 2020

(30) Foreign Application Priority Data

Sep. 11, 2018   (JP) .............................. JP2018-169547

(51) Int. Cl.
| | | |
|---|---|---|
| *G03F 7/004* | (2006.01) | |
| *C07C 59/115* | (2006.01) | |
| *G03F 7/039* | (2006.01) | |
| *G03F 7/038* | (2006.01) | |
| *C07D 207/27* | (2006.01) | |
| *C07C 43/225* | (2006.01) | |
| *C08F 220/16* | (2006.01) | |
| *C08F 220/28* | (2006.01) | |
| *C08F 212/14* | (2006.01) | |
| *C09D 133/08* | (2006.01) | |
| *C09D 133/14* | (2006.01) | |
| *C09D 125/14* | (2006.01) | |
| *C07C 25/18* | (2006.01) | |
| *G03F 7/16* | (2006.01) | |
| *G03F 7/20* | (2006.01) | |
| *G03F 7/38* | (2006.01) | |
| *G03F 7/32* | (2006.01) | |

(52) U.S. Cl.
CPC ............ *G03F 7/0045* (2013.01); *C07C 25/18* (2013.01); *C07C 43/225* (2013.01); *C07C 59/115* (2013.01); *C07D 207/27* (2013.01); *C08F 212/14* (2013.01); *C08F 220/16* (2013.01); *C08F 220/28* (2013.01); *C09D 125/14* (2013.01); *C09D 133/08* (2013.01); *C09D 133/14* (2013.01); *G03F 7/038* (2013.01); *G03F 7/039* (2013.01); *C08F 220/283* (2020.02); *G03F 7/162* (2013.01); *G03F 7/168* (2013.01); *G03F 7/2004* (2013.01); *G03F 7/2006* (2013.01); *G03F 7/2037* (2013.01); *G03F 7/2041* (2013.01); *G03F 7/322* (2013.01); *G03F 7/325* (2013.01); *G03F 7/38* (2013.01)

(58) Field of Classification Search
CPC ..... C07C 381/12; C07C 59/11; C07C 59/105; C07C 59/115; C07C 59/13; C07C 69/14
See application file for complete search history.

(56) References Cited

U.S. PATENT DOCUMENTS

| | | | |
|---|---|---|---|
| 6,479,210 B2 | 11/2002 | Kinoshita et al. | |
| 6,485,883 B2 | 11/2002 | Kodama et al. | |
| 6,492,091 B2 | 12/2002 | Kodama et al. | |
| 7,214,467 B2 | 5/2007 | Kanna et al. | |
| 9,221,742 B2 * | 12/2015 | Ohashi ................. | G03F 7/0045 |
| 10,120,278 B2 * | 11/2018 | Fukushima ............. | G03F 7/162 |
| 2013/0034813 A1 | 2/2013 | Ohsawa et al. | |
| 2013/0101936 A1 | 4/2013 | Taniguchi et al. | |
| 2015/0086926 A1 * | 3/2015 | Ohashi ................. | C07C 381/12 |
| | | | 430/285.1 |
| 2016/0349612 A1 | 12/2016 | Fujiwara et al. | |
| 2017/0226252 A1 | 8/2017 | Sagehashi et al. | |
| 2018/0039173 A1 | 2/2018 | Hatakeyama et al. | |
| 2019/0391488 A1 * | 12/2019 | Nishikori ............... | C07C 59/13 |

FOREIGN PATENT DOCUMENTS

| | | | |
|---|---|---|---|
| JP | 11-295887 A | | 10/1999 |
| JP | 11-327143 A | | 11/1999 |
| JP | 4105797 B2 | * | 6/2008 |
| JP | 4116340 B2 | | 7/2008 |
| JP | 4226803 B2 | | 2/2009 |
| JP | 4231622 B2 | | 3/2009 |
| JP | 2013-092590 A | | 5/2013 |
| JP | 5556765 B2 | | 7/2014 |
| KR | 10-2016-0140460 A | | 12/2016 |
| KR | 10-2018-0016958 A | | 2/2018 |
| TW | 201736964 A | | 10/2017 |

OTHER PUBLICATIONS

Office Action dated Nov. 25, 2020, issued in counterpart KR Application No. 10-2019-0112192, with English Translation. (18 pages).
Office Action dated Jul. 20, 2021, issued in counterpart JP Application No. 2018-169547, with English Translation. (5 pages).
Office Action dated May 11, 2020, issued in counterpart TW Application No. 108132344. (5 pages).

* cited by examiner

*Primary Examiner* — Amanda C. Walke

(74) *Attorney, Agent, or Firm* — WHDA, LLP

(57) ABSTRACT

A novel carboxylic acid iodonium salt and a resist composition comprising the same as a quencher are provided. When resist composition is processed by photolithography using KrF or ArF excimer laser, EB or EUV, there is formed a resist pattern which is improved in rectangularity, MEF, LWR, and CDU.

12 Claims, No Drawings

IODONIUM SALT, RESIST COMPOSITION, AND PATTERN FORMING PROCESS

CROSS-REFERENCE TO RELATED APPLICATION

This non-provisional application claims priority under 35 U.S.C. § 119(a) on Patent Application No. 2018-169547 filed in Japan on Sep. 11, 2018, the entire contents of which are hereby incorporated by reference.

TECHNICAL FIELD

This invention relates to an iodonium salt, a resist composition comprising the same, and a pattern forming process using the resist composition.

BACKGROUND ART

While a number of recent efforts are being made to achieve a finer pattern rule in the drive for higher integration and operating speeds in LSI devices, DUV and EUV lithography is thought to hold particular promise as the next generation in microfabrication technology. In particular, photolithography using an ArF excimer laser as the light source is thought requisite to the micropatterning technique capable of achieving a feature size of 0.13 μm or less.

For the purpose of meeting the miniaturization requirement, it is essential not only to optimize a base resin in a resist composition, but also to improve the performance of additives, typically photoacid generator (PAG). Particularly in chemically amplified resist compositions, it is important how to control the diffusion of strong acid generated upon exposure.

As the PAG, sulfonium salts, typically triphenylsulfonium nonafluorobutanesulfonate are generally used because of stability in resist compositions. When sulfonium salts are used in resist compositions, however, the generated acids are too diffusive to achieve a high resolution. To address the problem, partially fluorinated alkane sulfonic acids and salts thereof were developed. Studies were made on the PAGs which are endowed with an acid diffusion suppressing effect by introducing a bulky substituent or polar group therein. For example, triphenylsulfonium 2-(1-adamantanecarbonyloxy)-1,1,3,3,3-pentafluoro-propane-1-sulfonate is a PAG having an acid diffusion suppressing effect since it possesses a bulky substituent. A resist composition using this PAG, however, is still insufficient in the control of acid diffusion to a full extent. Its lithography performance is unsatisfactory when line width roughness (LWR) as an index of pattern roughness, resolution and other factors are totally evaluated.

In addition to the structural modification of PAGs, studies are made on quenchers or acid diffusion regulators. Amines and weak acid onium salts are typically used as the quencher. Patent Document 1 describes that the addition of triphenylsulfonium acetate ensures to form a satisfactory resist pattern without T-top profile, a difference in line width between isolated and grouped patterns, and standing waves. Patent Document 2 reports improvements in sensitivity, resolution and exposure margin by the addition of ammonium salts of sulfonic acids or carboxylic acids. Also, Patent Document 3 describes that a resist composition for KrF or EB lithography comprising a PAG capable of generating a fluorinated carboxylic acid is improved in resolution and process latitude such as exposure margin and depth of focus. Further, Patent Document 4 describes that a resist composition for $F_2$ laser lithography comprising a PAG capable of generating a fluorinated carboxylic acid is improved in line edge roughness (LER) and solves the footing problem.

While the foregoing patent documents refer to the KrF, EB and $F_2$ lithography. Patent Document 5 describes a positive photosensitive composition for ArF excimer laser lithography comprising a carboxylic acid onium salt. These systems are based on the mechanism that an ion exchange occurs between a weak acid onium salt and a strong acid (sulfonic acid) generated by another PAG upon exposure, to form a weak acid and a strong acid onium salt. That is, the strong acid (sulfonic acid) having high acidity is replaced by a weak acid (carboxylic acid), thereby suppressing acid-aided decomposition reaction of acid labile group and reducing or controlling the distance of acid diffusion.

Even when these weak acid onium salts are used, however, there are possibilities that pattern collapse occurs, resolution is improved no more, and the solubility in alkaline developer is low, leaving defects after development. Also lithography factors such as LWR are not satisfactory. For solving these problems. Patent Document 6 proposes a resist composition comprising a sulfonium salt of fluorinated carboxylic acid. This composition still fails to give satisfactory results with respect to patient profile and lithography performance.

CITATION LIST

Patent Document 1: JP-A H11-295887
Patent Document 2: JP-A H11-327143
Patent Document 3: JP 4231622 (U.S. Pat. No. 6,485,883)
Patent Document 4: JP 4116340 (U.S. Pat. No. 7,214,467)
Patent Document 5: JP 4226803 (U.S. Pat. No. 6,492,091)
Patent Document 6: JP 5556765

DISCLOSURE OF INVENTION

An object of the invention is to provide a carboxylic acid iodonium salt and a resist composition comprising the same as a quencher, the resist composition being processed by photolithography using high-energy radiation such as KrF or ArF excimer laser, EB or EUV as the energy source to form a resist pattern with improved rectangularity, MEF, LWR, and CDU, and a pattern forming process using the resist composition.

The inventors have found that a resist composition comprising an iodonium salt of specific structure is improved in many lithography performance factors including rectangularity, MEF, LWR, and CDU and thus best suited for precise micropatterning.

In one aspect, the invention provides an iodonium salt having the formula (1).

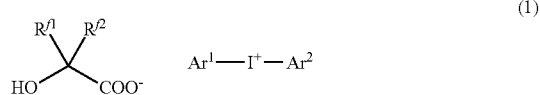

Herein $R^{f1}$ and $R^{f2}$ are each independently hydrogen, fluorine, or a $C_1$-$C_4$ straight or branched monovalent hydrocarbon group which may contain fluorine, at least one of $R^{f1}$ and $R^{f2}$ being fluorine or a $C_1$-$C_4$ straight or branched monovalent hydrocarbon group which may contain fluorine. $Ar^1$ and $Ar^2$ are each independently a $C_6$-$C_{40}$ aryl group which may contain a heteroatom, or $Ar^1$ and $Ar^2$ may bond together to form a ring with the iodine atom to which they are attached.

Preferably, $R^{f1}$ and $R^{f2}$ are each independently hydrogen, fluorine, methyl or trifluoromethyl.

Preferably, $Ar^1$ and $Ar^2$ are each independently unsubstituted phenyl or a phenyl group substituted with halogen, alkyl or alkoxy at the para-position to the iodine atom.

In a second aspect, the invention provides a quencher comprising the iodonium salt defined above.

In a third aspect, the invention provides a resist composition comprising the quencher.

In a preferred embodiment, the resist composition further comprises a base resin containing a polymer comprising recurring units having the formula (a) and reaming units having the formula (b).

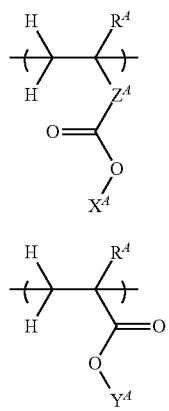

(a)

(b)

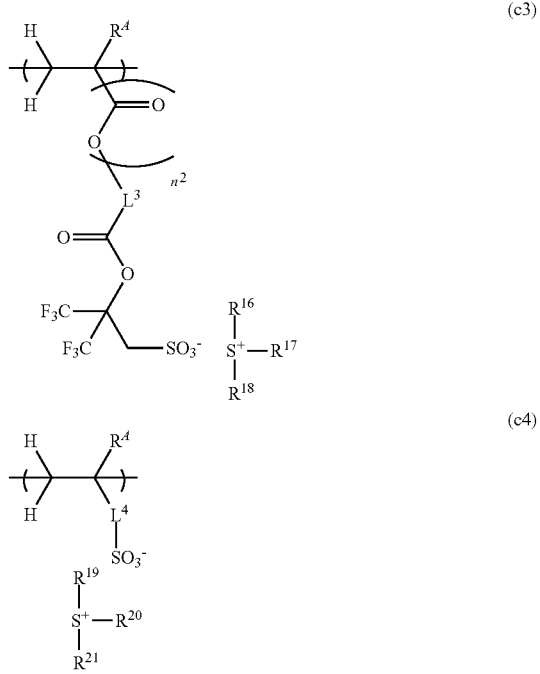

(c3)

(c4)

Herein $R_A$ is hydrogen, fluorine, methyl or trifluoromethyl. $Z^A$ is a single bond, phenylene, naphthylene or (backbone)-C(=O)—O—Z'—, wherein Z' is a $C_1$-$C_{10}$ alkanediyl group which may contain a hydroxyl moiety, ether bond ester bond or lactone ring, or phenylene or naphthylene. $X^A$ is an acid labile group. $Y^A$ is hydrogen or a polar group containing at least one structure selected from the group consisting of hydroxyl, cyano, carbonyl, carboxyl, ether bond, ester bond, sulfonic acid ester bond, carbonate bond, lactone ring, sultone ring and carboxylic anhydride.

In a preferred embodiment, the polymer further comprises recurring units of at least one type selected from recurring units having the formulae (c1) to (c4).

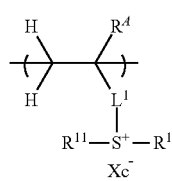

(c1)

(c2)

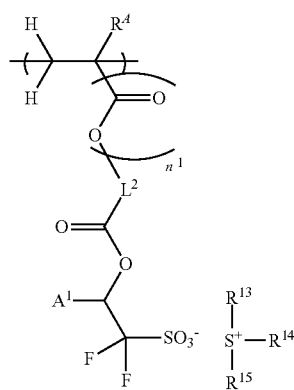

Herein $R^A$ is hydrogen, fluorine, methyl or trifluoromethyl. $L^1$ is a single bond, phenylene. —O-$L^{11}$-, —C(=O)—O-$L^{11}$- or —C(=O)—NH-$L^{11}$-, $L^{11}$ is a $C_1$-$C_{20}$ alkanediyl group, $C_2$-$C_{20}$ alkenediyl group or phenylene group, which may contain a heteroatom. $L^2$ and $L^3$ are each independently a single bond or a $C_1$-$C_{20}$ divalent hydrocarbon group which may contain a heteroatom. $L^4$ is a single bond, methylene, ethylene, phenylene, fluorinated phenylene, —O-$L^{41}$-, —C(=O)—O-$L^{41}$- or —O(=O)NH-$L^{41}$-, $L^{41}$ is an optionally substituted phenylene group. $R^{11}$ to $R^{21}$ are each independently a $C_1$-$C_{20}$ monovalent hydrocarbon group which may contain a heteroatom, any two of $L^1$, $R^{11}$ and $R^{12}$ may bond together to form a ring with the sulfur atom to which they are attached, any two of $R^{13}$, $R^{14}$ and $R^{15}$, any two of $R^{16}$, $R^{17}$ and $R^{18}$, or any two of $R^{19}$, $R^{20}$ and $R^{21}$ may bond together to form a ring with the sulfur atom to which they are attached. $Xc^-$ is a non-nucleophilic counter ion. $A^1$ is hydrogen or trifluoromethyl, $n^1$ is 0 or 1, $n^1$ is 0 when $L^2$ is a single bond, $n^2$ is 0 or 1, $n^2$ is 0 when $L^3$ is a single bond.

The resist composition may further comprise an organic solvent.

The resist composition may further comprise a photoacid generator. Preferably, the photoacid generator has the formula (2) or (3).

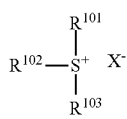

(2)

Herein $R^{101}$, $R^{102}$ and $R^{103}$ are each independently a $C_1$-$C_{20}$ monovalent hydrocarbon group which may contain a heteroatom, any two of $R^{101}$, $R^{102}$ and $R^{103}$ may bond together to form a ring with the sulfur atom to which they are attached. $X^-$ is an anion selected from the following formulae (2A) to (2D):

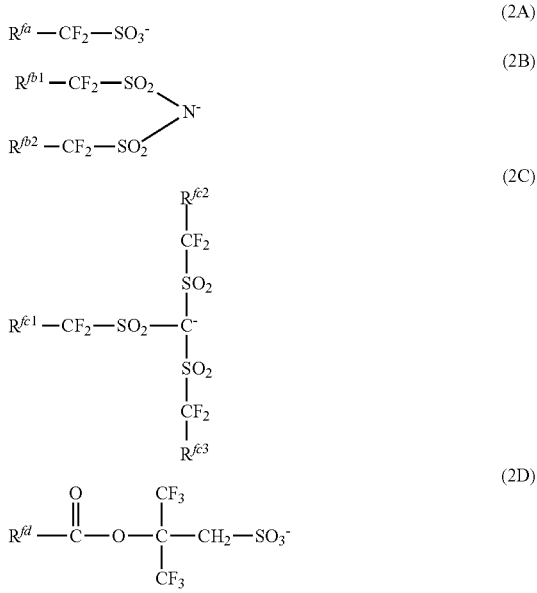

wherein $R^{fa}$, $R^{fb1}$, $R^{fb2}$, $R^{fc1}$, $R^{fc2}$ and $R^{fc3}$ are each independently fluorine or a $C_1$-$C_{40}$ monovalent hydrocarbon group which may contain a heteroatom, or a pair of $R^{fb1}$ and $R^{fb2}$, or $R^{fc1}$ and $R^{fc2}$ may bond together to form a ring with the carbon atom to which they are attached and any intervening atoms, $R^{fd}$ is a $C_1$-$C_{40}$ monovalent hydrocarbon group which may contain a heteroatom.

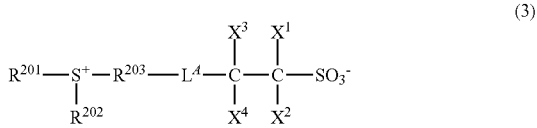

Herein $R^{201}$ and $R^{202}$ are each independently a $C_1$-$C_{30}$ monovalent hydrocarbon group which may contain a heteroatom, $R^{203}$ is a $C_1$-$C_{30}$ divalent hydrocarbon group which may contain a heteroatom, any two of $R^{201}$, $R^{202}$ and $R^{203}$ may bond together to form a ring with the sulfur atom to which they are attached, $L^A$ is a single bond, ether bond or a $C_1$-$C_{20}$ divalent hydrocarbon group which may contain a heteroatom, $X^1$, $X^2$, $X^3$ and $X^4$ are each independently hydrogen, fluorine or trifluoromethyl, at least one of $X^1$, $X^2$, $X^3$ and $X^1$ is fluorine or trifluoromethyl.

The resist composition may further comprise an amine compound.

The resist composition may further comprise a surfactant which is insoluble or substantially insoluble in water and soluble in alkaline developer, and/or a surfactant which is insoluble or substantially insoluble in water and alkaline developer.

In a fifth aspect, the invention provides a pattern forming process comprising the steps of applying the resist composition defined above onto a substrate to form a resist film, exposing a selected region of the resist film to KrF excimer laser, ArF excimer laser, EB or EUV, and developing the exposed resist film in a developer.

In a preferred embodiment, the developing step uses an alkaline aqueous solution as the developer, thereby forming a positive pattern in which an exposed region of the resist film is dissolved away and an unexposed region of the resist film is not dissolved.

In another preferred embodiment, the developing step uses an organic solvent as the developer, thereby forming a negative pattern in which an unexposed region of the resist film is dissolved away and an exposed region of the resist film is not dissolved.

Preferably, the organic solvent is at least one solvent selected from the group consisting of 2-octanone, 2-nonanone, 2-heptanone, 3-heptanone, 4-heptanone, 2-hexanone, 3-hexanone, diisobutyl ketone, methylcyclohexanone, acetophenone, methylacetophenone, propyl acetate, butyl acetate, isobutyl acetate, pentyl acetate, butenyl acetate, isopentyl acetate, propyl formate, butyl formate, isobutyl formate, pentyl formate, isopentyl formate, methyl valerate, methyl pentenoate, methyl crotonate, ethyl crotonate, methyl propionate, ethyl propionate, ethyl 3-vale rate, methyl lactate, ethyl lactate, propyl lactate, butyl lactate, isobutyl lactate, pentyl lactate, isopentyl lactate, methyl 2-hydroxyisobutyrate, ethyl 2-hydroxyisobutyrate, methyl benzoate, ethyl benzoate, phenyl acetate, benzyl acetate, methyl phenylacetate, benzyl formate, phenylethyl formate, methyl 3-phenylpropionate, benzyl propionate, ethyl phenylacetate, and 2-phenylethyl acetate.

In a preferred embodiment, the exposure step is carried out by immersion lithography while a liquid having a refractive index of at least 1.0 is held between the resist film and a projection leas.

The process may further comprise the step of coating a protective film on the resist film prior to the exposure step, wherein immersion lithography is carried out while the liquid is held between the protective film and the projection lens.

Advantageous Effects of Invention

When a resist composition comprising the inventive iodonium salt as a quencher is processed by photolithography using high-energy radiation such as KrF or ArF excimer laser, EB or EUV, especially ArF excimer laser or EUV as the energy source, a resist pattern with improved rectangularity, MEF, LWR, and CDU is formed, because the extent of acid diffusion is significantly controlled.

DESCRIPTION OF EMBODIMENTS

As used herein, the singular forms "a", "an" and "the" include plural referents unless the context clearly dictates otherwise. "Optional" or "optionally" means that the subsequently described event or circumstances may or may not occur, and that description includes instances where the event or circumstance occurs and instances where it does not. The notation (Cn-Cm) means a group containing from n to m carbon atoms per group. In chemical formulae, Me stands for methyl, Ac for acetyl, nBu for n-butyl, tBu for tert-butyl, Ph for phenyl, and the broken line designates a valence bond.

The abbreviations and acronyms have the following meaning.
EB: election beam
EUV: extreme ultraviolet
Mw: weight average molecular weight
Mn: number average molecular weight
Mw/Mn: molecular weight distribution or dispersity
GPC: gel permeation chromatography
PEB: post-exposure bake
PAG: photoacid generator
LWR: line width roughness
MEF: mask error factor CDU: critical dimension uniformity It is understood that for some structures represented by chemical formulae, there can exist enantiomers and diastereomers because of the presence of asymmetric carbon atoms. In such a case, a single formula collectively represents all such isomers. The isomers may be used alone or in admixture.

Iodonium Salt

One embodiment of the invention is an iodonium salt having the formula (1).

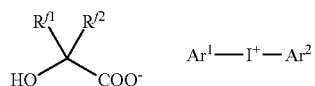

(1)

In formula (1), $R^{f1}$ and $R^{f2}$ are each independently hydrogen, fluorine, or a $C_1$-$C_4$ straight or branched monovalent hydrocarbon group which may contain fluorine. At least one of $R^{f1}$ and $R^{f2}$ is fluorine or a $C_1$-$C_4$ straight or branched monovalent hydrocarbon group which may contain fluorine.

Examples of the monovalent hydrocarbon group include methyl ethyl, n-propyl isopropyl, n-butyl, monofluoromethyl, difluoromethyl, trifluoromethyl, 2,2,2-trifluoromethyl, pentafluoromethyl, heptafluoropropyl, nonafluorobutyl, 2,2,2-trifluoroethyl, and 1-trifluoromethyl-2,2,2-trifluoroethyl. $R^{f1}$ and $R^{f2}$ are preferably hydrogen, methyl, fluorine or trifluoromethyl, most preferably trifluoromethyl. When both $R^{f1}$ and $R^{f2}$ are trifluoromethyl, the conjugated acid of carboxylate anion has an appropriately increased acidity, and the steric structure around the nucleophilic site becomes so bulky that nucleophilicity is appropriately suppressed. An improvement in stability of the resist composition is thus expectable. The inclusion of a fluoroalcohol unit leads to an improvement in compatibility and hence, uniform dispersion in the resist film. Thus improvements in lithography performance factors such as LWR and CDU are expectable.

In formula (1), $Ar^1$ and $Ar^2$ are each independently a $C_6$-$C_{40}$ aryl group which may contain a heteroatom, or $Ar^1$ and $A^2$ may bond together to form a ring with the iodine atom to which they are attached.

Examples of the aryl group include, but are not limited to, phenyl, naphthyl, tolyl, xylyl, trimethylphenyl, ethylphenyl, isopropylphenyl, tert-butylphenyl, 1-adamantylphenyl, triisopropylphenyl, tricyclohexylphenyl, methoxyphenyl, ethoxyphenyl, butoxyphenyl, hydroxyphenyl, dihydroxyphenyl, trimethoxyphenyl, methylthiophenyl, biphenyl, fluorophenyl, difluorophenyl, bromophenyl, iodophenyl, N,N-diphenylaminophenyl, acetoxyphenyl, acetylaminophenyl, 2,2,2-trifluoroethoxyphenyl, (2-methoxyethoxy) phenyl, hydroxynaphthyl, dihydroxynaphthyl, 2,2,2-trifluoroethoxynaphthyl, and (2-methoxyethoxy)naphthyl, with the proviso that in the case of a substituted group, the position of a substituent is arbitrary.

Also included in the aryl group are aryl groups having a polymerizable substituent such as acryloyloxy or methacryloyloxy. Examples include 4-acryloyloxypheuyl, 4-methacryloyloxyphenyl, 4-acryloyloxy-3,5-dimethylphenyl, 4-methacryloyloxy-3,5-dimethylphenyl, 4-vinyloxyphenyl, 4-vinylphenyl, 4-(2-acryloyloxyethoxy)phenyl, and 4-(2-methacryloyloxyethoxy)phenyl.

$Ar^1$ and $Ar^2$ are preferably unsubstituted phenyl groups, or phenyl groups substituted with halogen, alkyl or alkoxy at the para-position to the iodine atom. More preferably $Ar^1$ and $Ar^2$ are phenyl, 4-tert-butylphenyl or 4-fluorophenyl.

Where $Ar^1$ and $Ar^2$ bond together to form a ring with the iodine atom to which they are attached. $Ar^1$ and $Ar^2$ may bond directly or via an oxygen atom, methylene, sulfone or carbonyl group. Examples of the ring structure thus formed are shown below, but not limited thereto. It is noted that in any of the following formulae, a substituent may be attached to an aromatic ring at an arbitrary position.

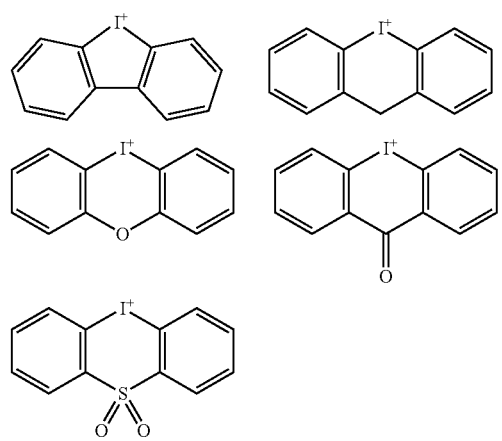

Examples of the anion in the iodonium salt having formula (1) are given below, but not limited thereto.

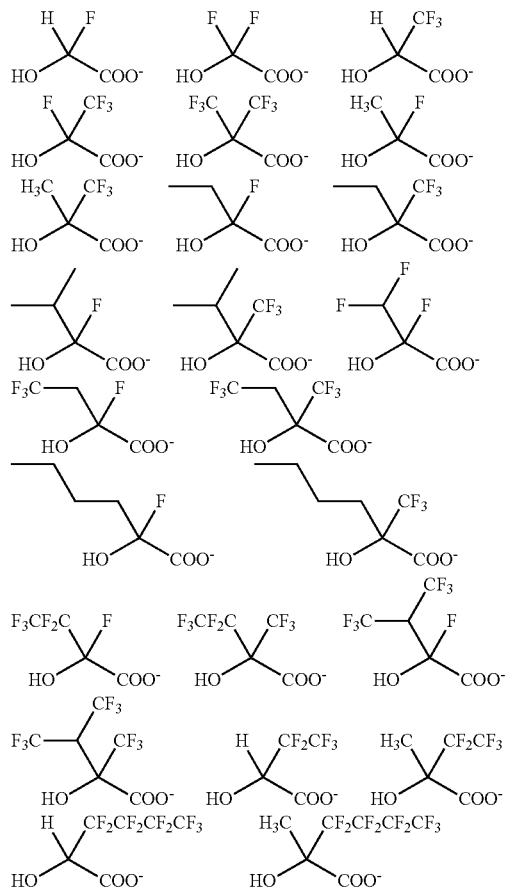

Examples of the cation in the iodonium salt having formula (1) are given below, but not limited thereto.
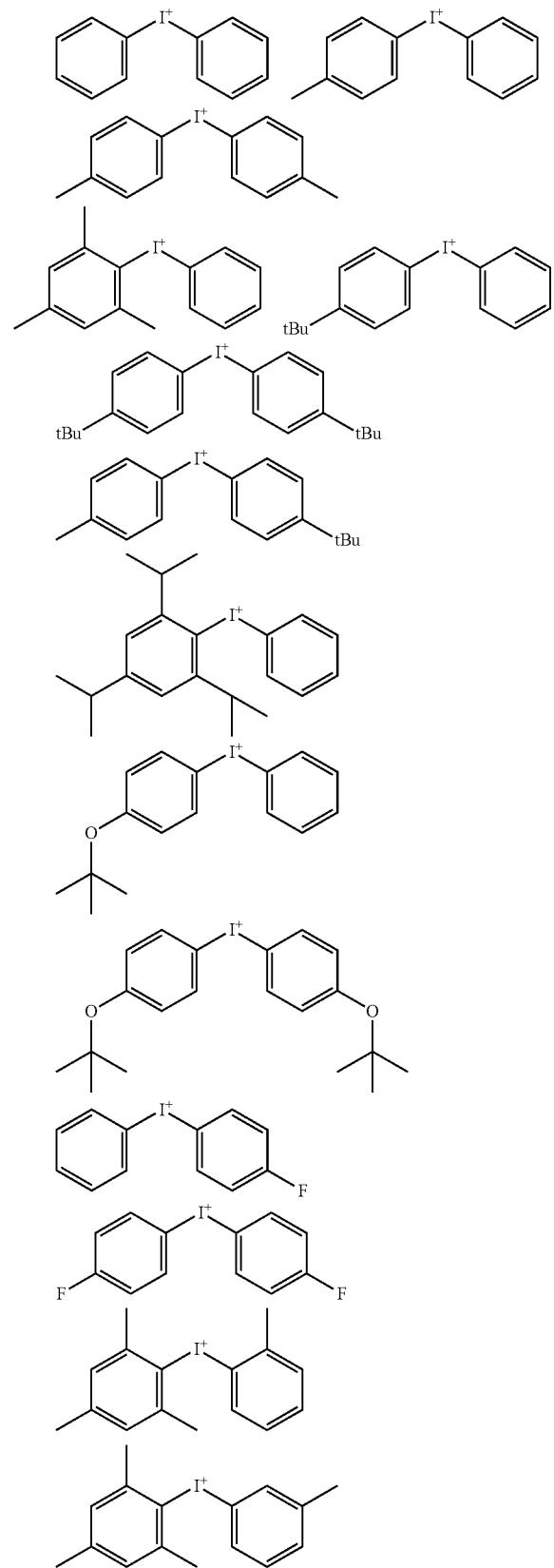
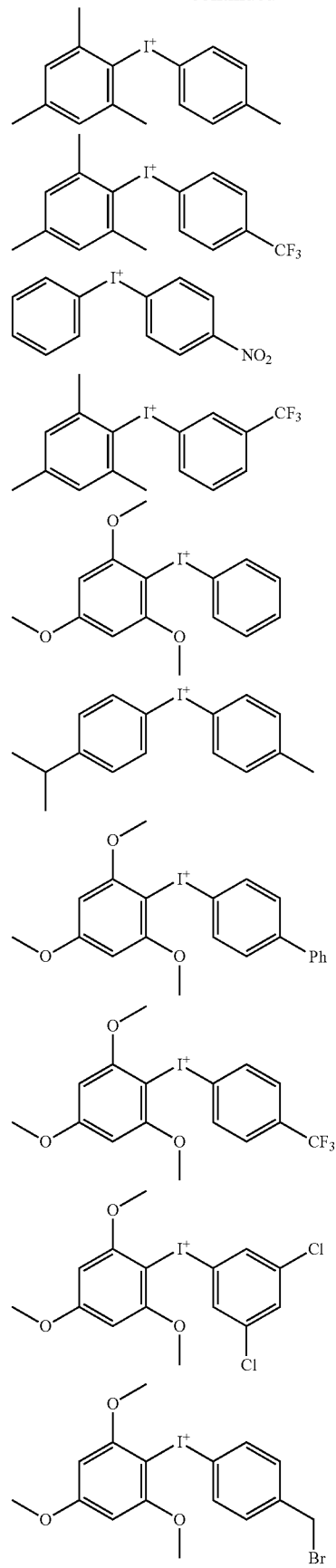

-continued
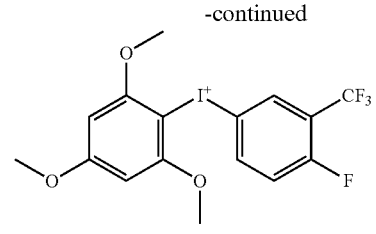
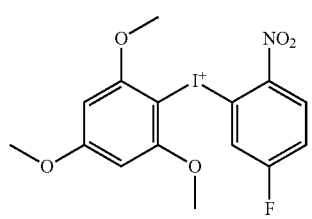
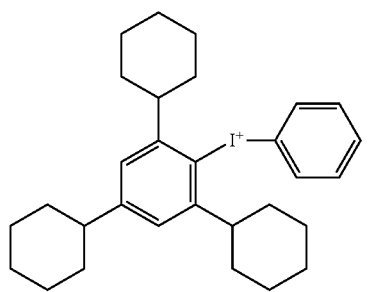
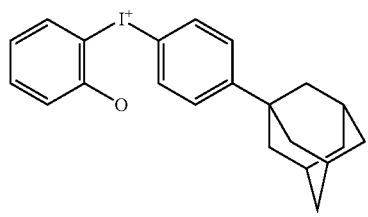
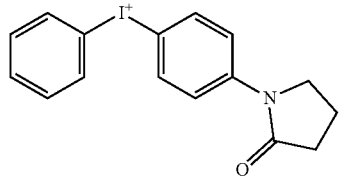
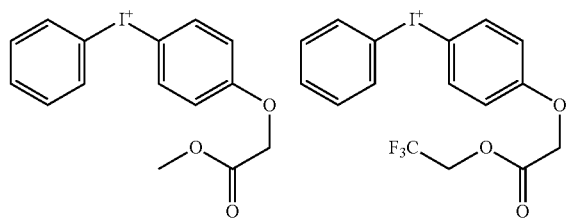
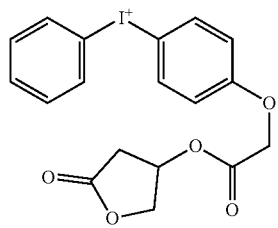
-continued
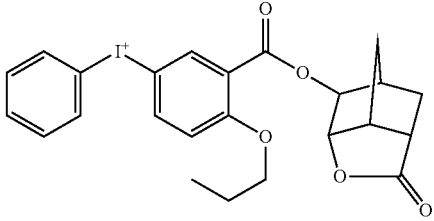
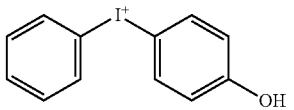
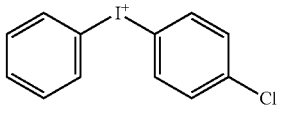
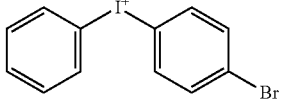
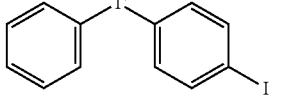
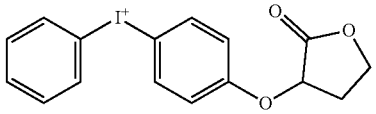
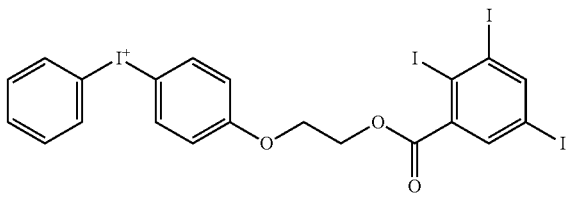
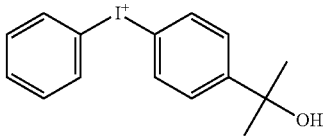
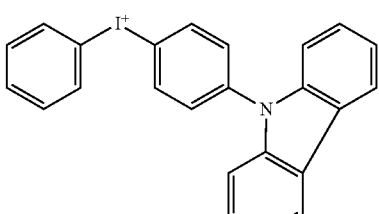
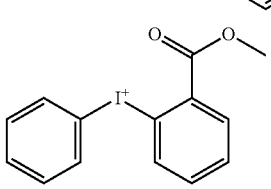
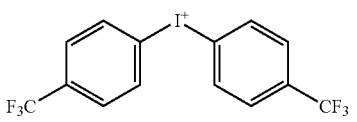

-continued

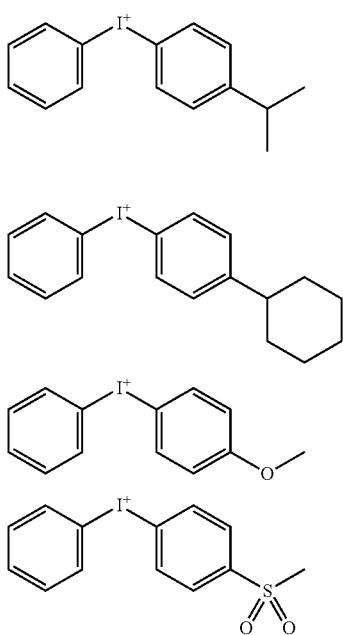

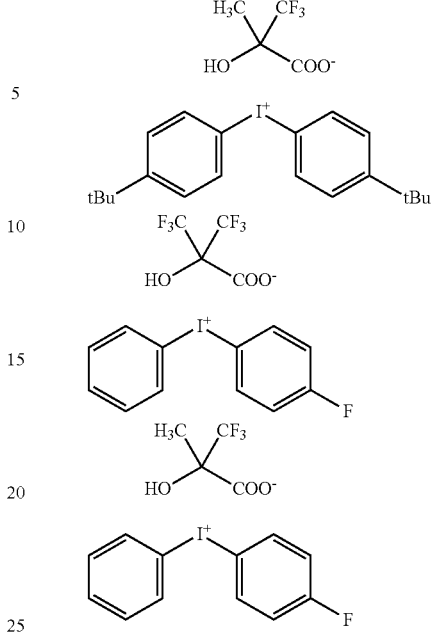

Exemplary structures of the iodonium salt include arbitrary combinations of cations with anions, both as exemplified above, but are not limited thereto. Preferred structures are shown below.

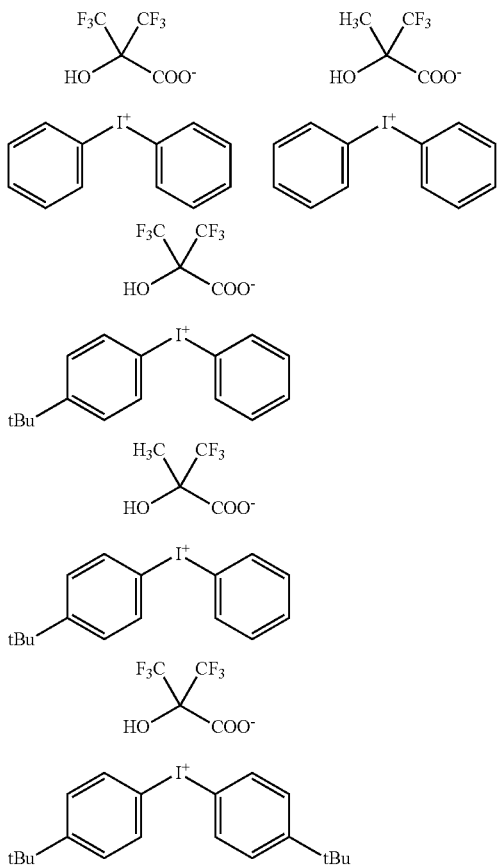

The resist composition comprising the inventive iodonium salt as a quencher is improved in lithography performance factors such as rectangularity, MEF, LWR, and CDU. Although the reason why such benefits are obtainable is not well understood, the following reason is estimated.

By virtue of a fluoroalcohol unit in its anion skeleton the inventive iodonium salt is highly compatible and uniformly dispersed in the resist film, whereby lithography factors such as LWR and CDU are improved. Since the iodonium cation has a high dissolution inhibiting ability as compared with the sulfonium cation, a resist composition of alkaline development type comprising the inventive iodonium salt is improved in rectangularity owing to the suppressed dissolution of the pattern top in the developer.

The inventive iodonium salt is thermally stable as compared with a triarylsulfonium salt having the same anion. Although the reason is not well understood, the following reason is estimated. The inventive iodonium salt has the structure that the anion has hydroxyl and carboxyl groups via methylene. The salt is stabilized through the mechanism that the oxygen atoms on these two functional groups and the cation moiety (M$^+$) form a ring structure as shown by the following formula (1'). In forming the ring structure, the iodonium cation is low in steric hindrance and likely to form a ring structure since the iodine atom at the center has a large atomic radius and two aryl groups bond thereto. In contrast, the triarylsulfonium cation is high in steric hindrance and unlikely to take a stable structure since the sulfur atom at the center has a small atomic radius and three aryl groups bond thereto. These lead to a decline of thermal stability.

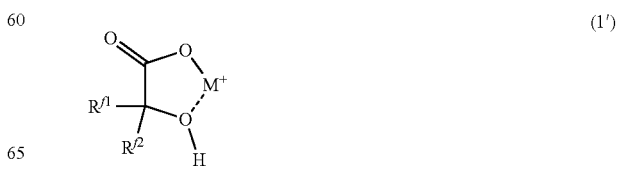

(1')

Herein $R^{f1}$ and $R^{f2}$ are as defined above, and M is iodine or sulfur.

The inventive iodonium salt is likely to take a stable structure, which contributes to an increase in the ability to inhibit dissolution in alkaline developer and an improvement in rectangularity.

The inventive iodonium salt may be synthesized, for example, according to the scheme shown below although the synthesis route is not limited thereto.

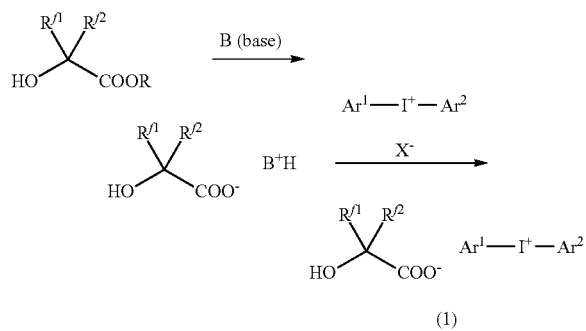

Herein $R^{f1}$, $R^{f2}$, $Ar^1$ and $Ar^2$ are as defined above, R is hydrogen or alkyl, B is a base, and $X^-$ is an anion.

The starting compound may be synthesized by various methods, for example, by adding hydrogen cyanide to a corresponding carbonyl compound and effecting hydrolysis thereof. However, hydrogen cyanide is a virulent poison, and some carbonyl compounds such as hexafluoroacetone are also virulent. They need careful handling. In contrast, 3,3,3-trifluoro-2-hydroxy-2-(trifluoromethyl)propionic acid derivatives, especially methyl esters thereof are obtained from octafluoroisobutylene which is a by-product during the synthesis of hexafluoropropene. These fluorine compounds are available in large volume and at a relatively low cost because their source is the by-product of an industrial product.

The first step of hydrolysis reaction is described in detail. The reactant, α-hydroxycarboxylic acid or ester thereof may be a commercially available compound or synthesized by the above-mentioned method. Examples of the base used herein include lithium hydroxide, sodium hydroxide, potassium hydroxide, calcium hydroxide, tetramethyl ammonium hydroxide, tetraethylammonium hydroxide, tetrabutylammonium hydroxide, and ammonium hydroxide. Inter alia, sodium hydroxide and tetramethylammonium hydroxide are preferred.

The amount of the base used is preferably 0.8 to 3 equivalents, more preferably 0.9 to 1.2 equivalents per equivalent of the α-hydroxycarboxylic acid or ester thereof. Suitable solvents include water, water-methanol, water-ethanol, and water-tetrahydrofuran, with water being preferred. Although the reaction temperature and time are arbitrary, a temperature from room temperature to about 40° C. is preferred in order to accelerate the consumption of the reactant. The reaction solution may be used as such (as carboxylic salt solution) in the subsequent step or ion exchange reaction. The reaction solution may be concentrated (solvent removal), after which crude crystals be taken out (as carboxylic salt). An acid such as hydrochloric acid may be added to the reaction solution for neutralizing basicity. Alternatively, the reaction solution may be washed with a hydrophobic organic solvent in which the carboxylic salt is insoluble, such as hexane, toluene, diethyl ether or diisopropyl ether, prior to use in the second step.

The second step of ion exchange reaction is described in detail. The ion exchange reaction may be performed by any well-known method, typically in an organic solvent or a mixture of an organic solvent and water. Suitable organic solvents include dichloroethane, chloroform, ethyl acetate, methyl isobutyl ketone, methanol, ethanol, acetonitrile, and 1-pentanol while they may be used alone or in admixture. After the salt by-product is removed, the product may be purified by a standard method such as recrystallization or chromatography.

While an iodonium salt is used in the ion exchange reaction, examples of the anion of the iodonium salt include, but are not limited to, chloride, bromide, methansulfonate, p-toluenesulfonate, nitrate, sulfate, carbonate, hydrogencarbonate, methylsulfate, and acetate ions. Inter alia, chloride, p-toluenesulfonate and acetate ions are preferred.

Resist Composition

Another embodiment of the invention is directed to a resist composition comprising (A) a quencher in the form of the iodonium salt having formula (1) as an essential component, (B) a base resin and (C) an organic solvent as optional components. If necessary, the resist composition may further comprise at least one component selected from (D) a photoacid generator, (E) a surfactant, (F) a quencher other than component (A), and (G) another component.

(A) Iodonium Salt

Component (A) in the resist composition is the inventive iodonium salt, which is added as a quencher. The amount of the iodonium salt as component (A) is preferably 0.1 to 20 parts by weight, more preferably 0.5 to 10 parts by weight per 100 parts by weight of the base resin as component (B). When the amount is at least 0.1 part, the iodonium salt may function as the quencher. When the amount is up to 20 parts, any performance losses such as formation of foreign particles due to a shortage of dissolution may be avoided.

The iodonium salt having formula (1) may be used alone or in admixture. Since the inventive iodonium salt mainly functions as a photo-decomposable quencher, it is preferably used in combination with a photoacid generator capable of generating a strong acid such as α-fluorinated sulfonic acid. In this embodiment, the photoacid generator capable of generating a strong acid may take the form of a base resin having recurring units containing an acid-generating site incorporated therein, or be added to the resist composition separately from the base resin.

Typically the inventive iodonium salt is used as a quencher to formulate a resist composition. The resist composition exhibits excellent lithography performance in terms of rectangularity, LWR and CDU, when applied to photolithography using high-energy radiation such as KrF or ArF excimer Laser, EB or EUV as the energy source.

(B) Base Resin

The base resin used in the resist composition is preferably a polymer comprising recurring units having the formula (a) and recurring units having the formula (b).

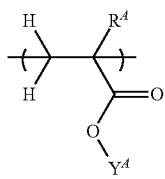

(b)

In formulae (a) and (b), $R^A$ is hydrogen, fluorine, methyl or trifluoromethyl. $Z^A$ is a single bond, phenylene, naphthylene or (backbone)-C(=O)—O—Z'—, wherein Z' is a $C_1$-$C_{10}$ alkanediyl group winch may contain a hydroxyl moiety, ether bond, ester bond or lactone ring, or a phenylene or naphthylene group. $X^A$ is an acid labile group. $Y^A$ is hydrogen or a polar group having at least one structure selected from the group consisting of hydroxyl, cyano, carbonyl, carboxyl, ether bond, ester bond, sulfonate bond, carbonate bond, lactone ring, sultone ring, and carboxylic anhydride (—C(=O)—O—C(=O)—).

The alkanediyl group may be straight, branched or cyclic, and examples thereof include methylene, ethane-1,1-diyl, ethane-1,2-diyl, propane-1,2-diyl, propane-2,2-diyl, propane-1,3-diyl, 2-methylpropane-1,3-diyl, butane-1,3-diyl, butane-2,3-diyl, butane-1,4-diyl, pentane-1,3-diyl, pentane-1,4-diyl, 2,2-dimethylpropane-1,3-diyl, pentane-1,5-diyl, hexane-1,6-diyl, cyclopentane-1,2-diyl, cyclopentane-1,3-diyl, and cyclohexane-1,6-diyl.

Examples of the structure of formula (a) wherein $Z^A$ is a variant are illustrated below, but not limited thereto. Herein $R^A$ and $X^A$ are as defined above.

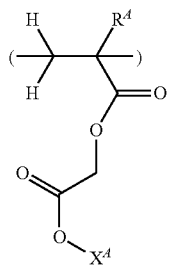
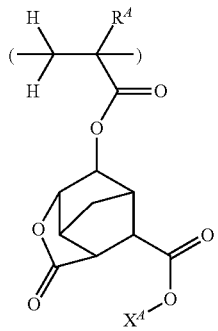
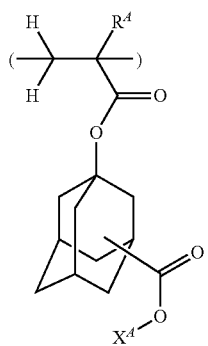

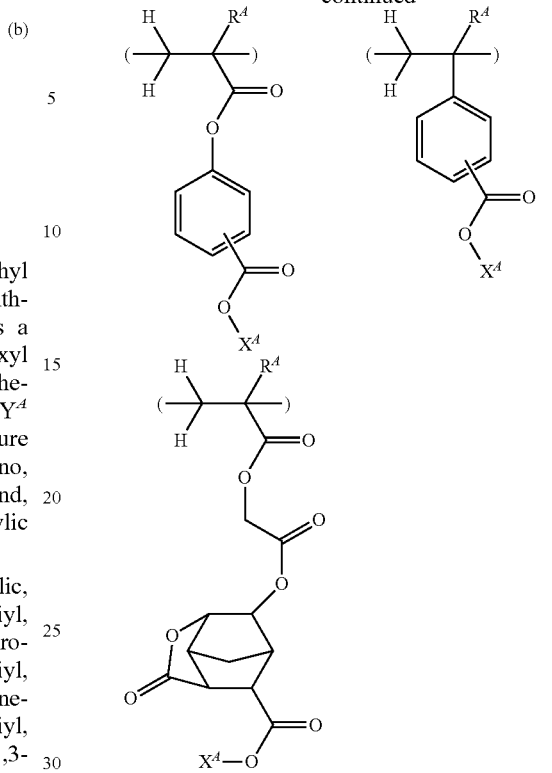

The acid labile group represented by $X^A$ may be selected from a variety of such groups. Examples of the acid labile group include $C_4$-$C_{20}$ tertiary alkyl groups, trialkylsilyl groups in which each alkyl moiety has 1 to 6 carbon atoms, and $C_4$-$C_{20}$ oxoalkyl groups. With respect to the structure of these acid labile groups, reference should be made to JP-A 2014-225005, paragraphs [0016]-[0035].

Groups of the following formulae (xa), (xb) and (xc) are especially preferred as the acid labile group.

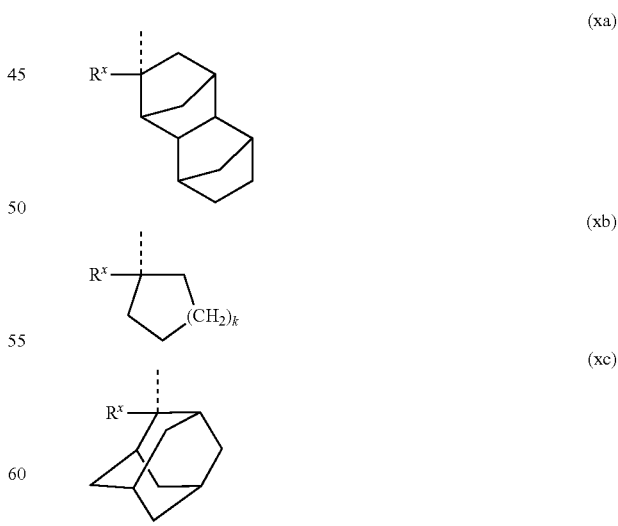

Herein $R^x$ is a $C_1$-$C_{10}$ monovalent hydrocarbon group which may contain a heteroatom, and k is 1 or 2.

When a tertiary alicyclic hydrocarbon group represented by formula (xa), (xb) or (xc) is bonded to the ester oxygen, the group becomes more acid labile due to steric repulsion, than other tertiary alkyl groups, for example, tert-butyl and tert-pentyl. When the tertiary alicyclic hydrocarbon group is used as a polarity switch unit in a resist composition, the dissolution contrast between exposed and unexposed regions is enhanced. Then a pattern having improved lithography performance in terms of LWR, CDU and rectangularity is obtained.

Examples of the recurring unit having formula (a) are given below, but not limited thereto. Herein $R^A$ is as defined above.

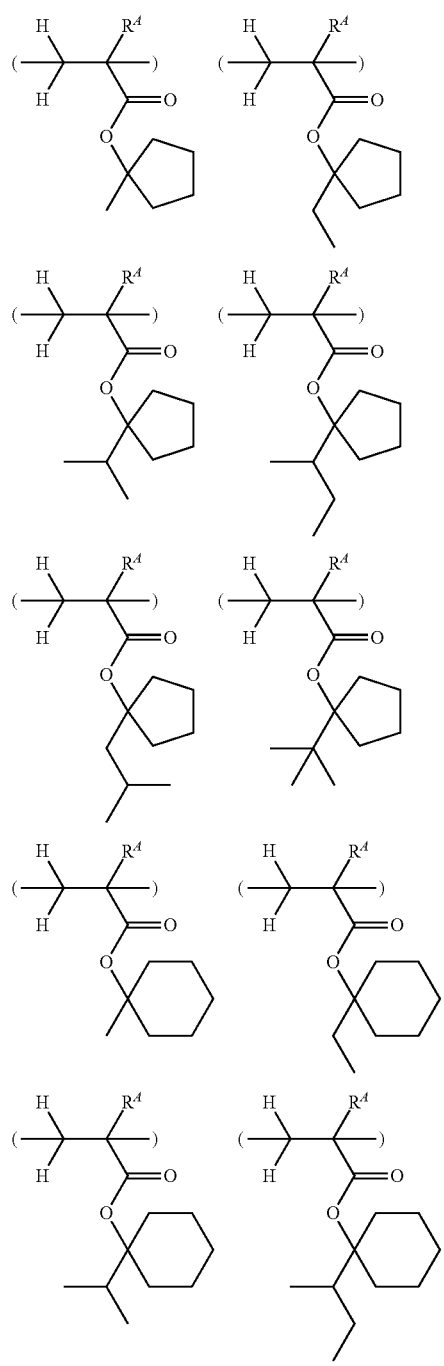

-continued

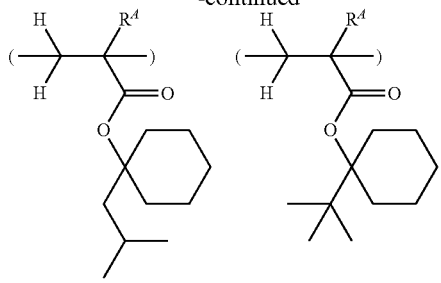

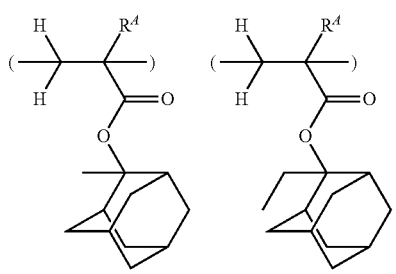

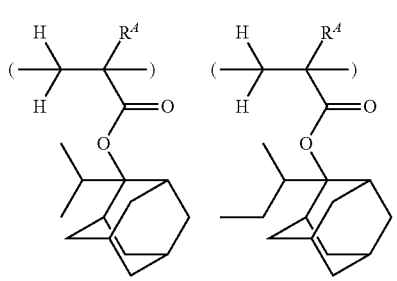

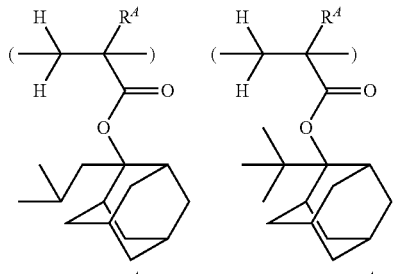

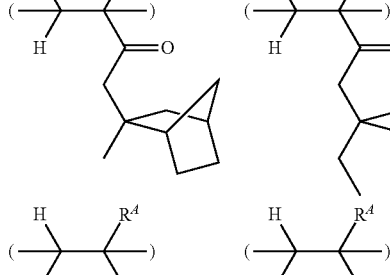

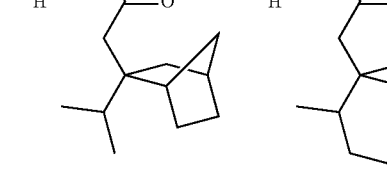

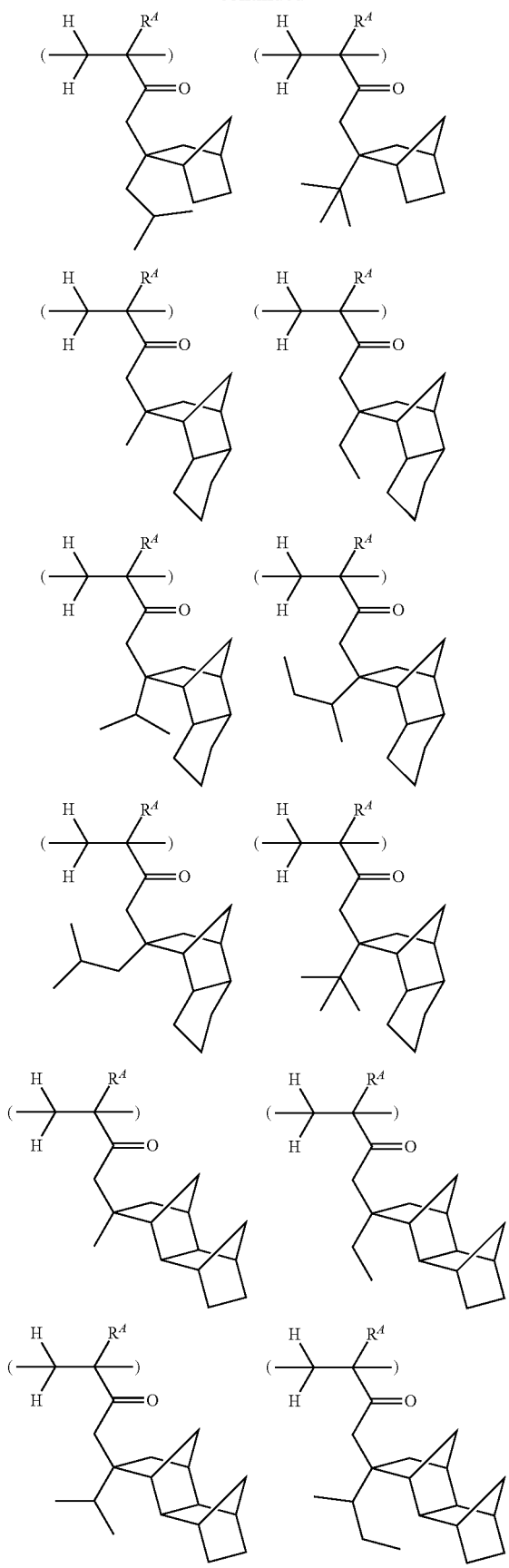
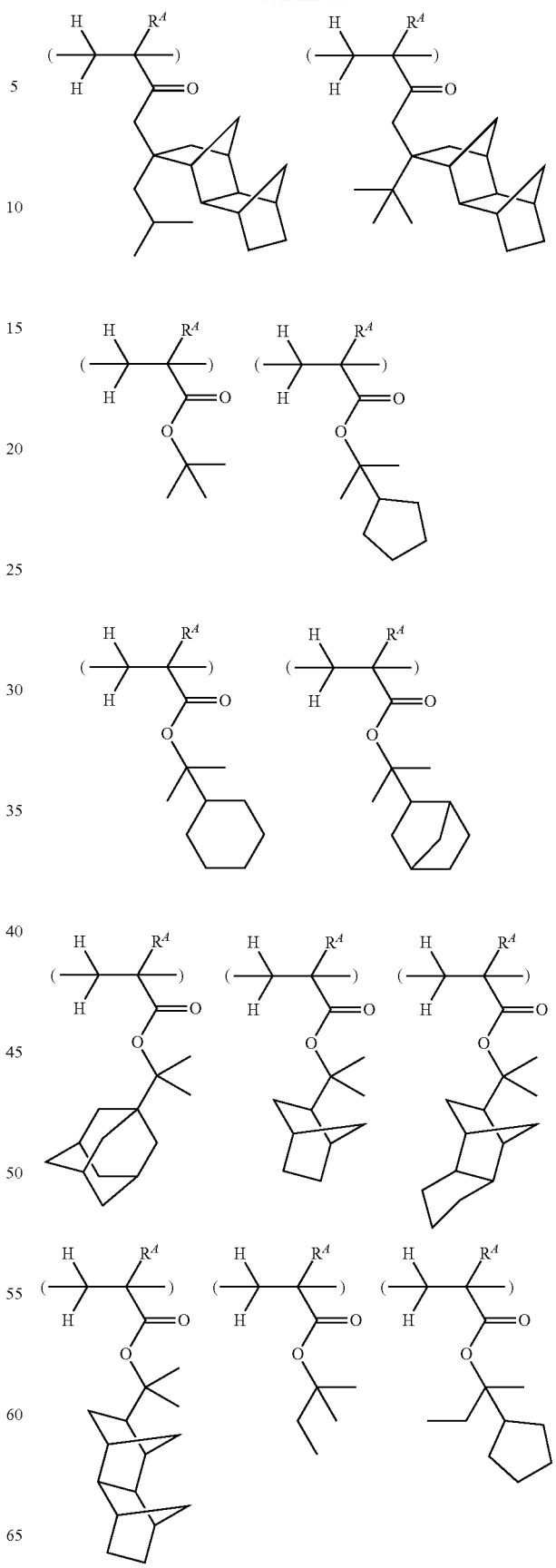

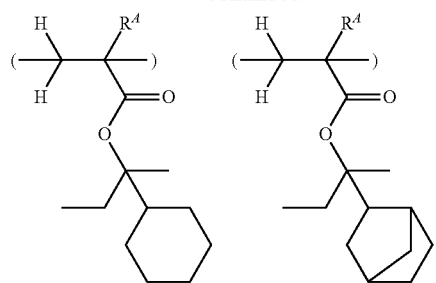
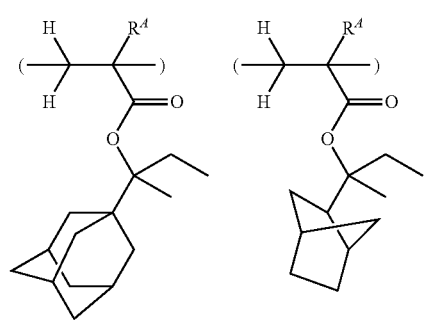
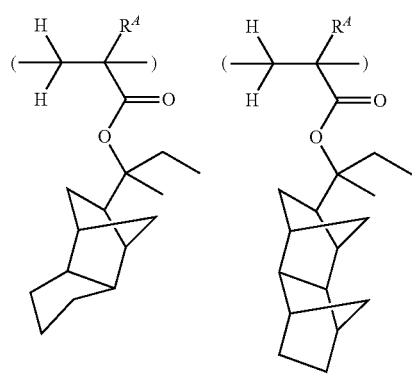
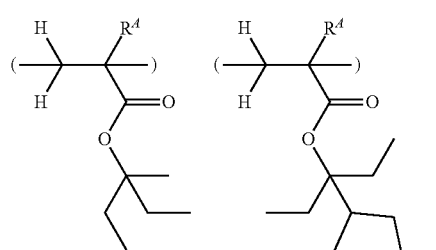
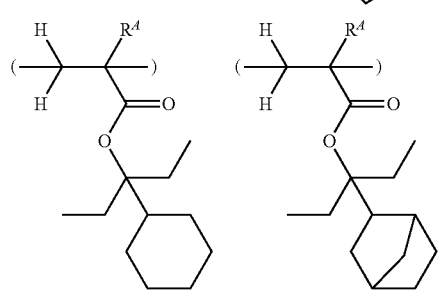
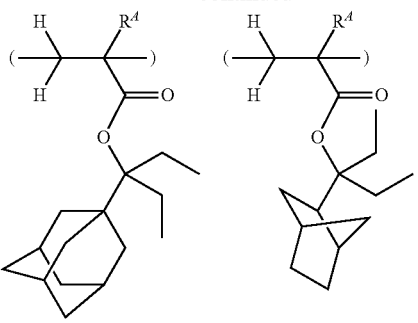
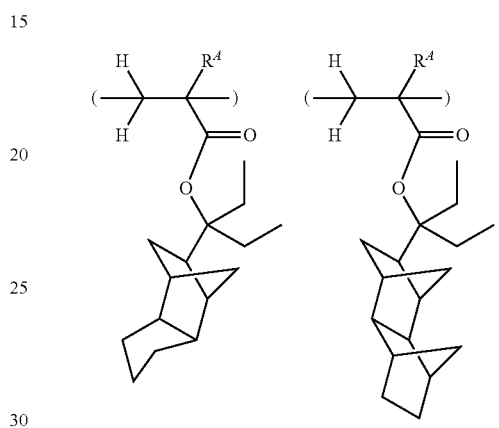
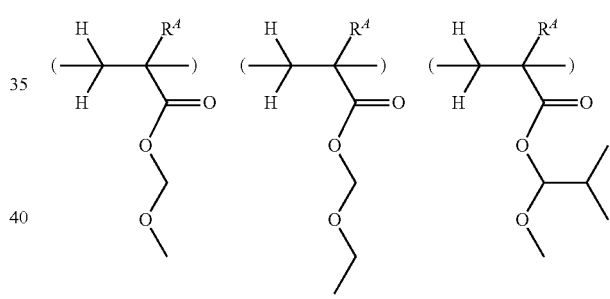
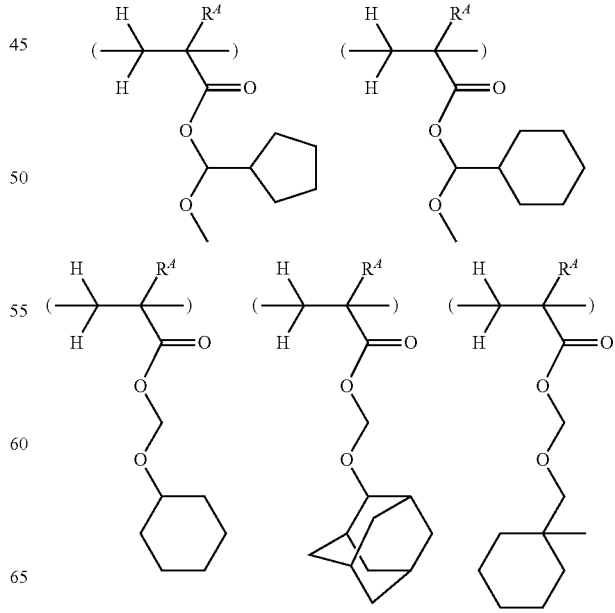

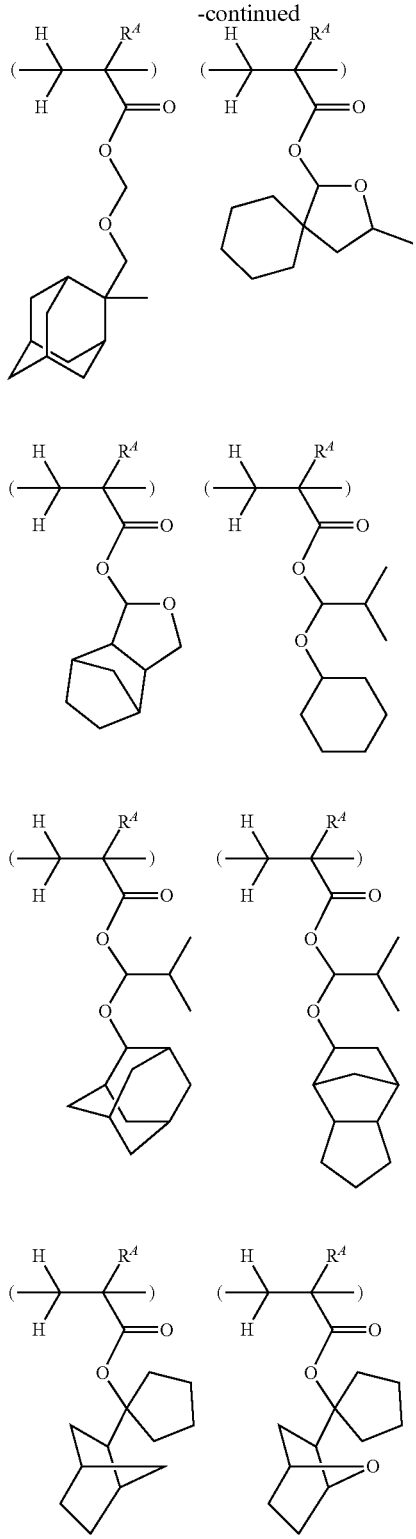

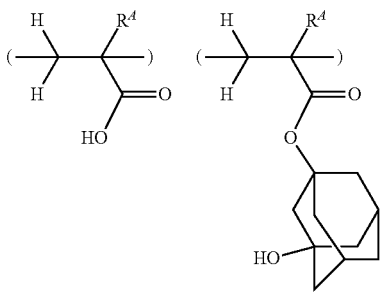

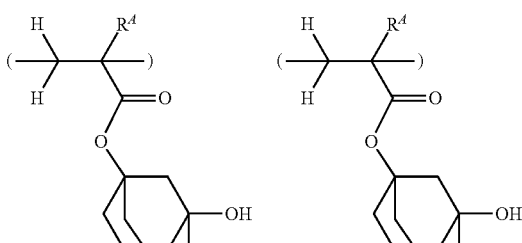

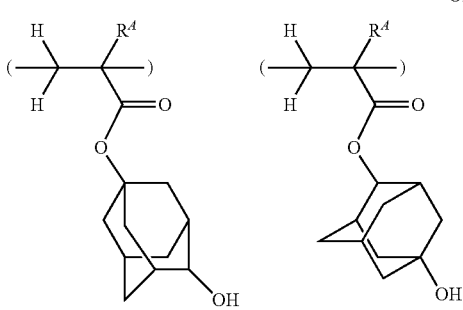

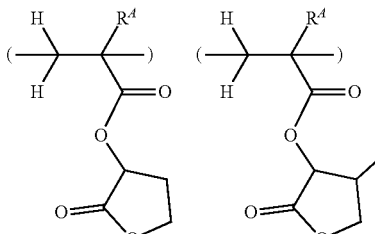

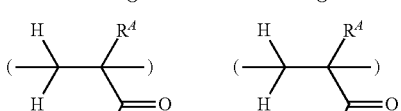

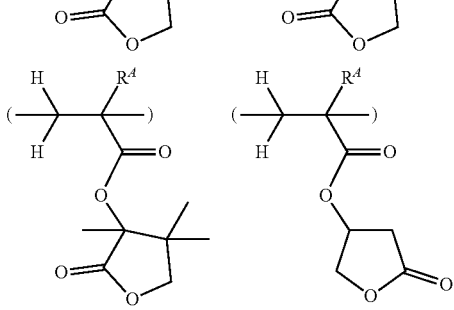

Although the above examples correspond to the unit having formula (a) wherein $Z^A$ is a single bond, combinations with similar acid labile groups are possible where $Z^A$ is other than a single bond. Groups of $Z^A$ other than a single bond are as shown above.

Examples of the recurring unit having formula (b) are given below, but not limited thereto. Herein $R^A$ is as defined above.

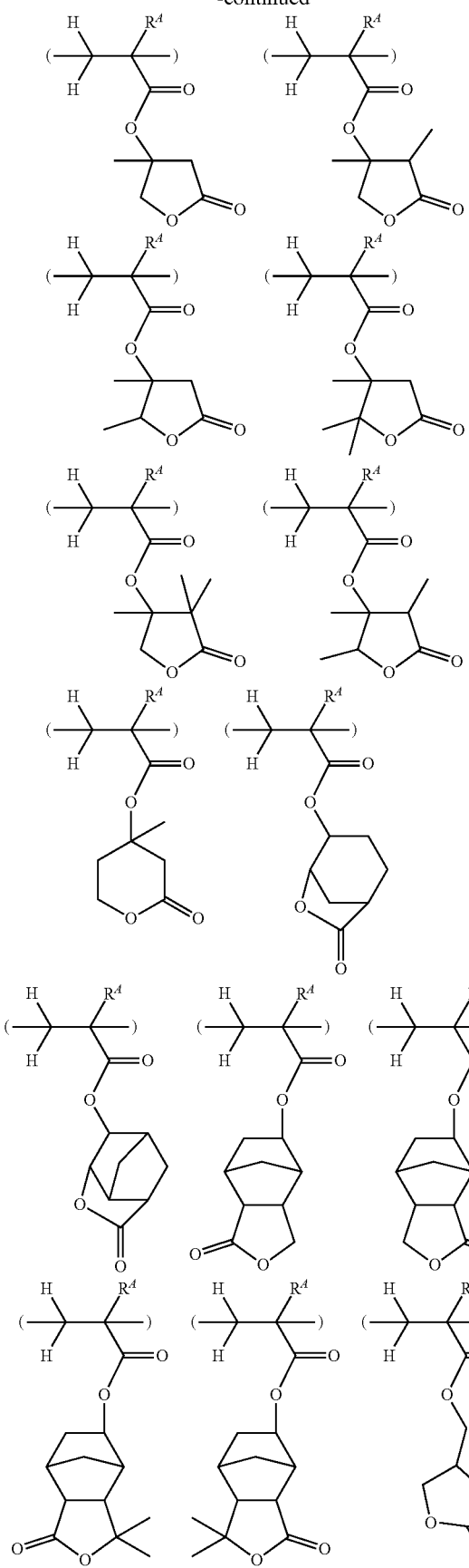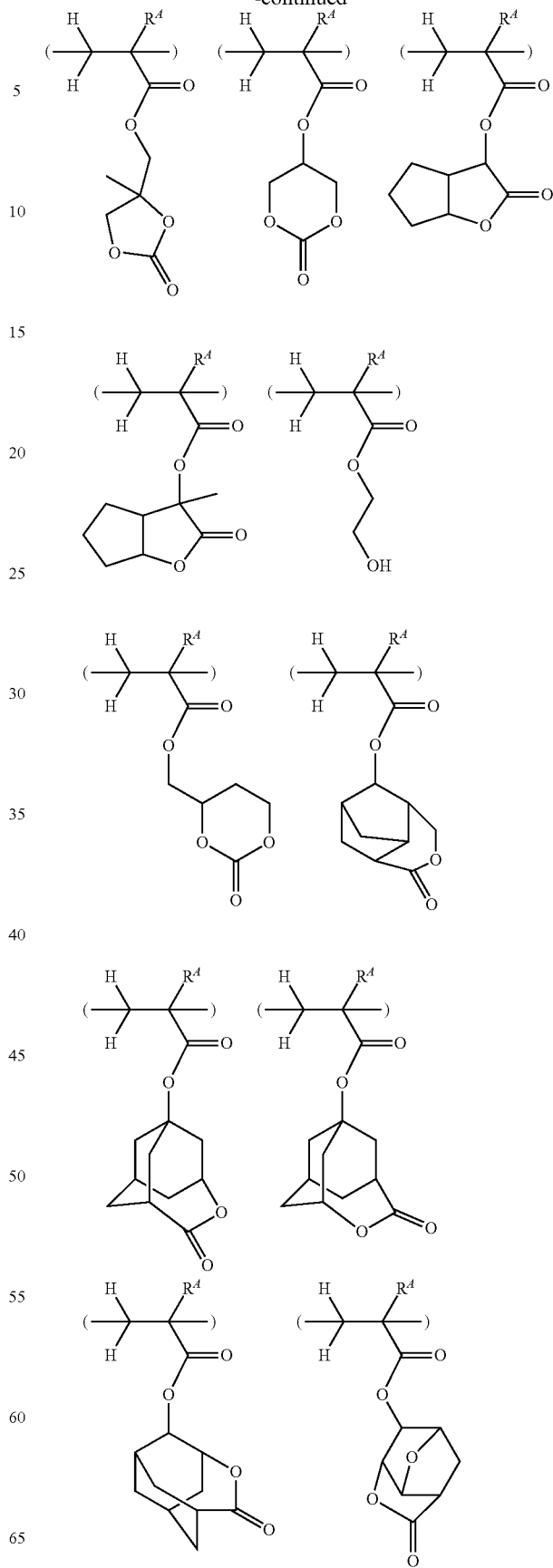

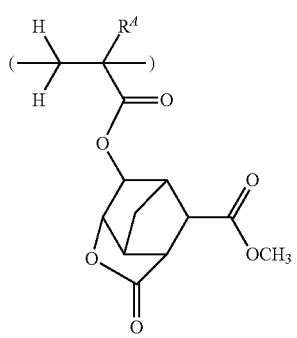
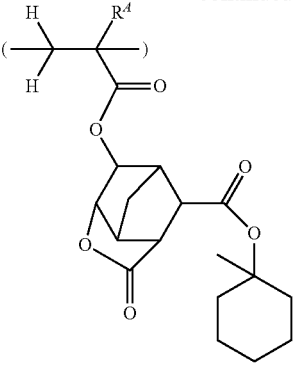
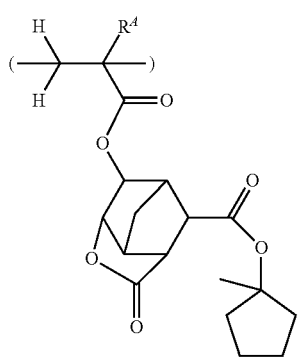
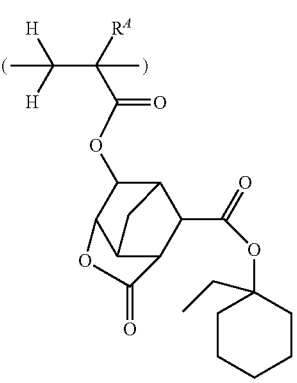
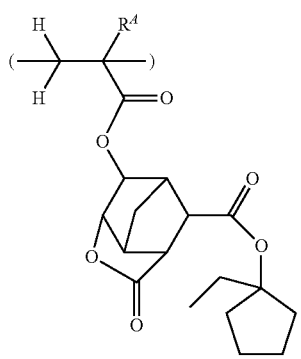
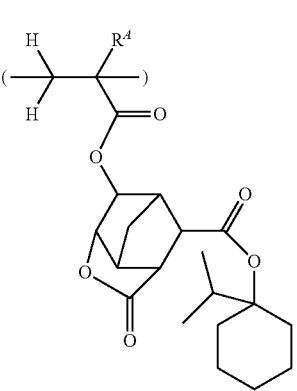
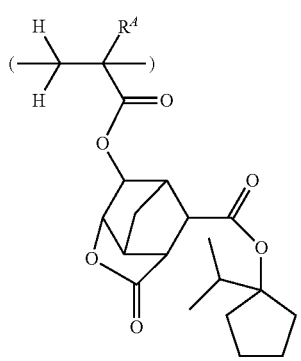
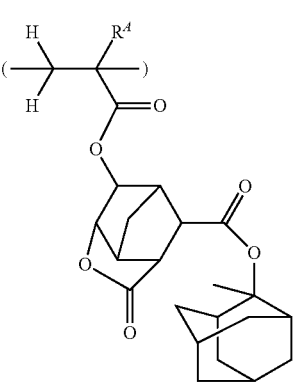

-continued
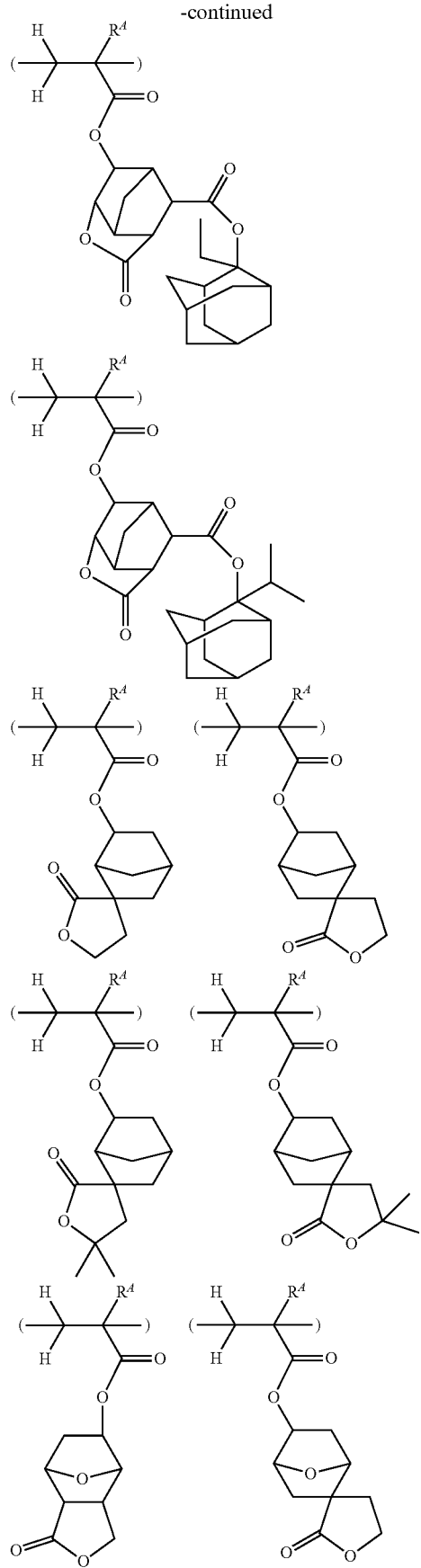
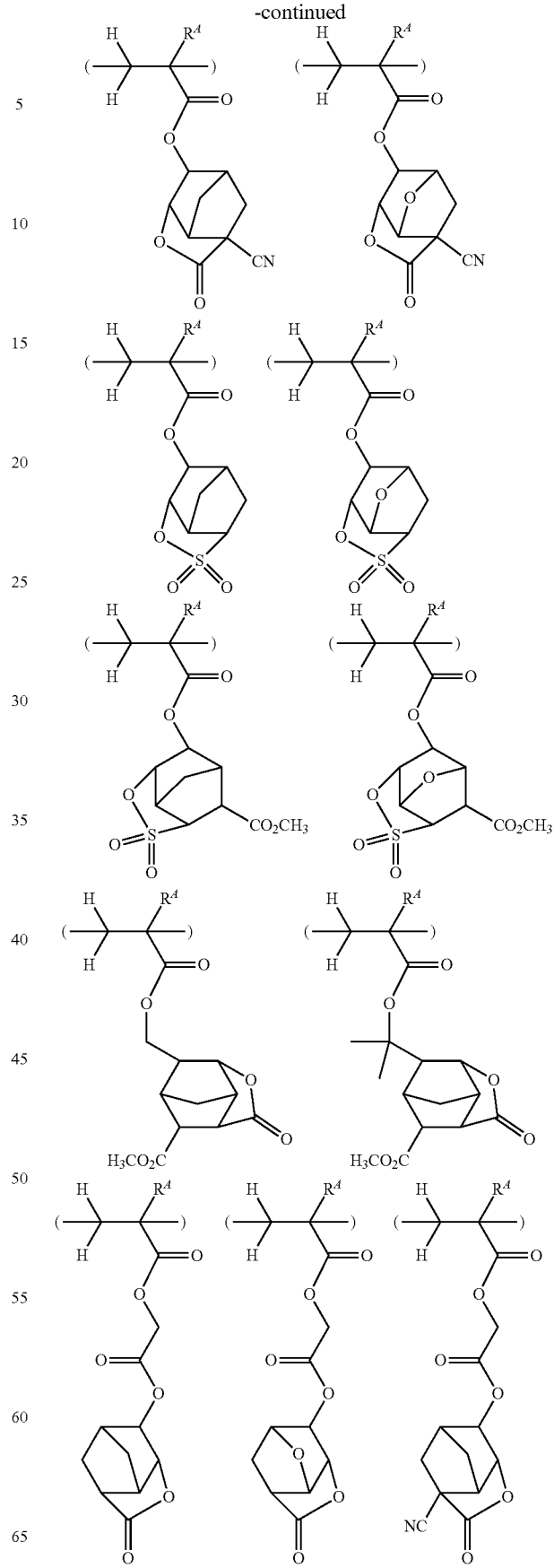

-continued
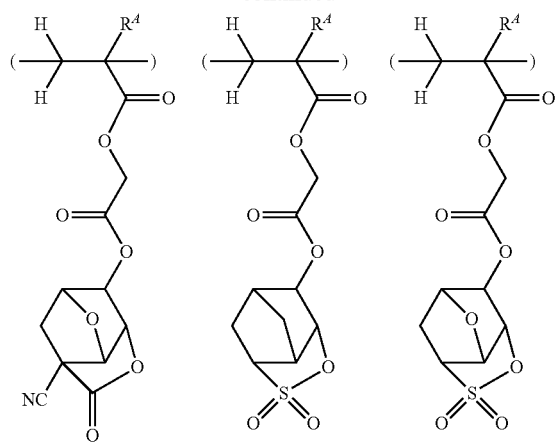
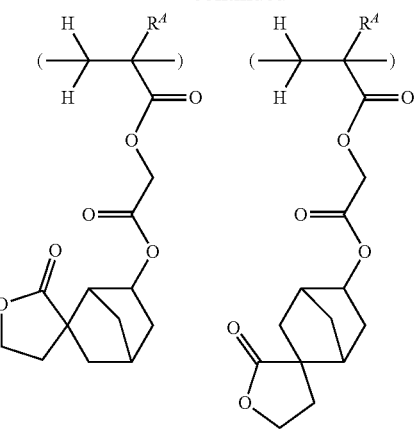
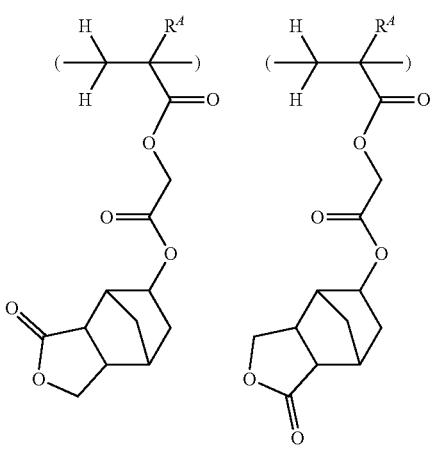
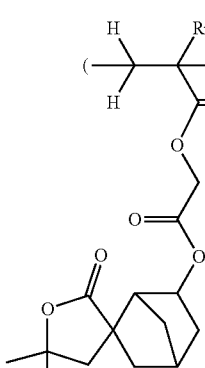
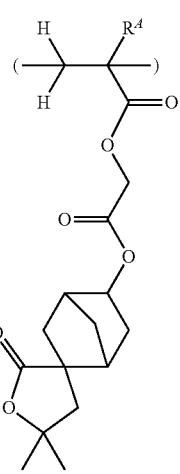
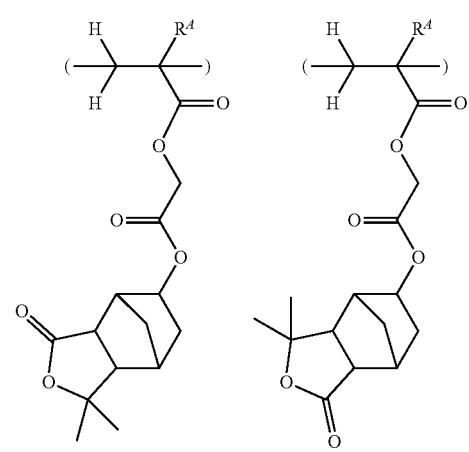
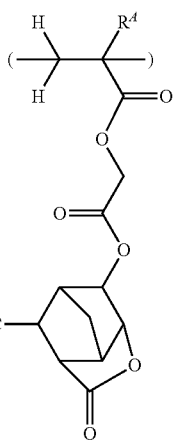
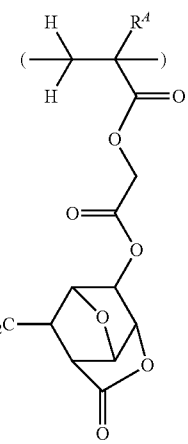
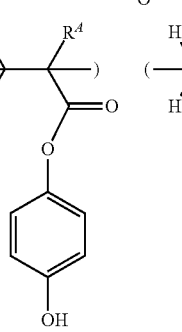
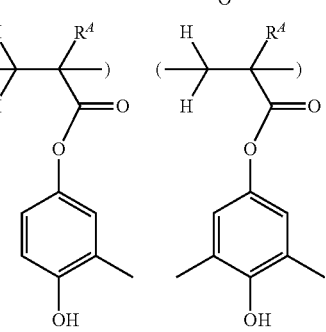

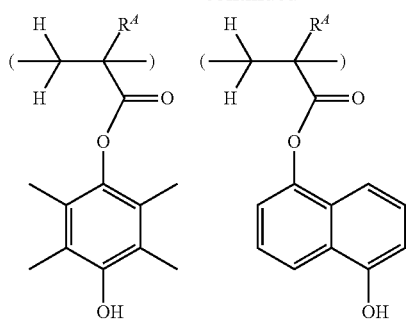

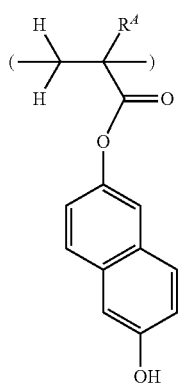

The polymer may further comprise reclining units of at least one type selected from recurring units having the formulae (c1) to (c4).

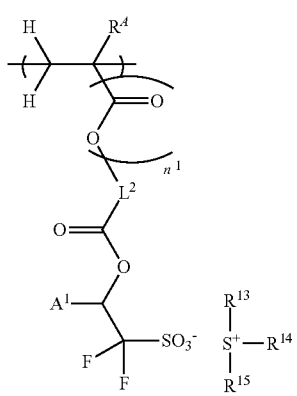

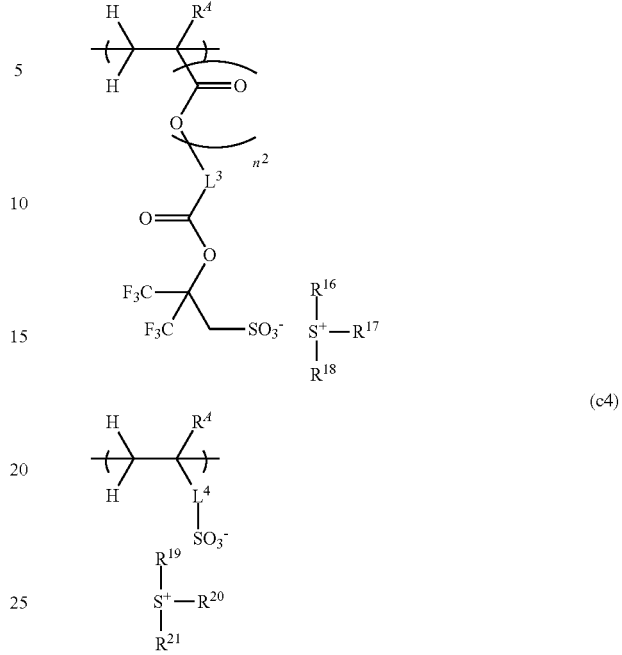

In formulae (c1) to (c4). $R^A$ is hydrogen, fluorine, methyl or trifluoromethyl. $L^1$ is a single bond, phenylene. —O-$L^{11}$-, —C(=O)—O-$L^{11}$- or —C(=O)—NH-$L^{11}$-, wherein $L^{11}$ is a $C_1$-$C_{20}$ alkanediyl group, $C_2$-$C_{20}$ alkenediyl group or phenylene group, which may contain a heteroatom. $L^2$ and $L^3$ are each independently a single bond or a $C_1$-$C_{20}$ divalent hydrocarbon group which may contain a heteroatom. $L^4$ is a single bond, methylene, ethylene, phenylene, fluorinated phenylene. —O-$L^{41}$-, —C(=O)—O-$L^{41}$- or —C(=O)—NH-$L^{41}$-, wherein $L^{41}$ is an optionally substituted phenylene group. $A^1$ is hydrogen or trifluoromethyl, $n^1$ is 0 or 1, $n^1$ is 0 when $L^2$ is a single bond, $n^2$ is 0 or 1, $n^2$ is 0 when $L^3$ is a single bond.

The alkanediyl group represented by $L^{11}$ may be straight, branched or cyclic. Examples thereof include methylene, ethane-1,1-diyl, ethane-1,2-diyl, propane-1,2-diyl, propane-2,2-diyl, propane-1,3-diyl, 2-methylpropane-1,3-diyl, butane-1,3-diyl, butane-2,3-diyl)butane-1,4-diyl, pentane-1,3-diyl, pentane-1,4-diyl, 2,2-dimethylpropane-1,3-diyl, pentane-1,5-diyl, hexane-1,6-diyl, cyclopentane-1,2-diyl, cyclopentane-1,3-diyl, and cyclohexane-1,6-diyl. The alkenediyl group represented by $L^{11}$ may be straight, branched or cyclic, and examples thereof include ethene-1,2-diyl, 1-propene-1,3-diyl, 2-butene-1,4-diyl, 1-methyl-1-butene-1,4-diyl, and 2-cyclohexene-1,4-diyl.

The divalent hydrocarbon group represented by $L^2$ and $L^3$ may be straight, branched or cyclic, and examples thereof include alkanediyl and alkenediyl groups as exemplified above.

In formulae (c1) to (c4). $R^{11}$ to $R^{21}$ are each independently a $C_1$-$C_{20}$ monovalent hydrocarbon group which may contain a heteroatom. The monovalent hydrocarbon group may be straight, branched or cyclic. Examples include alkyl groups such as methyl, ethyl, n-propyl, isopropyl, n-butyl, and t-butyl, monovalent saturated cycloaliphatic hydrocarbon groups such as cyclopropyl, cyclopentyl, cyclohexyl, cyclopropylmethyl, 4-methylcyclohexyl, cyclohexylmethyl, norbornyl, and adamantyl, alkenyl groups such as vinyl, allyl, propenyl, butenyl, and hexenyl, monovalent unsaturated cycloaliphatic hydrocarbon groups such as cyclohexenyl, aryl groups such as phenyl and naphthyl, heteroaryl groups such as thienyl, and aralkyl groups such as benzyl, 1-phenylethyl and 2-phenylethyl. Inter alia, aryl groups are preferred. In these hydrocarbon groups, some hydrogen may be substituted by a moiety containing a heteroatom such as oxygen, sulfur, nitrogen or halogen, and some carbon may be replaced by a moiety containing a heteroatom such as oxygen, sulfur or nitrogen, so that the group may contain a hydroxyl moiety, cyano moiety, carbonyl moiety, ether bond, ester bond, sulfonic acid ester bond, carbonate bond, lactone ring, sultone ring, carboxylic anhydride or haloalkyl moiety.

Any two of $L^1$, $R^{11}$ and $R^{12}$ may bond together to form a ring with the sulfur atom to which they are attached, any two of $R^{13}$, $R^{14}$ and $R^{15}$, any two of $R^{16}$, $R^{17}$ and $R^{18}$, or any two of $R^{19}$, $R^{20}$ and $R^{21}$ may bond together to form a ring with the sulfur atom to which they are attached.

In formula (c1), $Xc^-$ is a non-nucleophilic counter ion. Examples of the non-nucleophilic counter ion include halide ions such as chloride and bromide ions; fluoroalkylsulfonate ions such as triflate, 1,1,1-trifluoroethanesulfonate, and nonafluorobutanesulfonate; arylsulfonate ions such as tosylate, benzenesulfonate, 4-fluorobenzeuesulfonate, and 1,2,3,4,5-pentafluorobenzenesulfonate; alkylsulfonate ions such as mesylate and butanesulfonate; imide ions such as bis(trifluoromethylsulfonyl)imide, bis(perfluoroethylsulfonyl)imide and bis(perfluorobutylsulfonyl)imide; and methide ions such as tris(trifluoromethylsulfonyl)methide and tris(perfluoroethylsulfonyl)methide.

Other examples of the non-nucleophilic counter ion represented by $Xc^-$ include anions having the formulae (c5) and (c6).

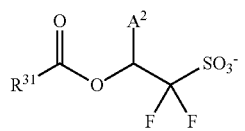

(c5)

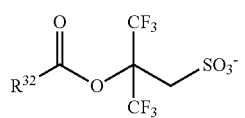

(c6)

Herein $R^{31}$ and $R^{32}$ are each independently a $C_1$-$C_{40}$ monovalent hydrocarbon group which may contain a heteroatom, and $A^2$ is hydrogen or trifluoromethyl.

Exemplary structures of the anion moiety in formula (c2) are as described in JP-A 2014-177407, paragraphs [0021]-[0026]. Exemplary structures of the anion moiety in formula (c2) wherein $A^1$ is hydrogen are as described in JP-A 2010-116550, paragraphs [0021]-[0028]. Exemplary structures of the anion moiety in formula (c2) wherein $A^1$ is trifluoromethyl are as described in JP-A 2010-077404, paragraphs [0021]-[0027], Exemplary structures of the anion moiety in formula (c3) include the exemplary structures of the anion moiety in formula (c2) wherein —$CH(A^1)CF_2SO_3^-$ is replaced by —$C(CF_3)_2CH_2SO_3^-$.

Preferred examples of the anion moiety in formula (c2) are shown below, but not limited thereto. Herein $A^1$ is as defined above.

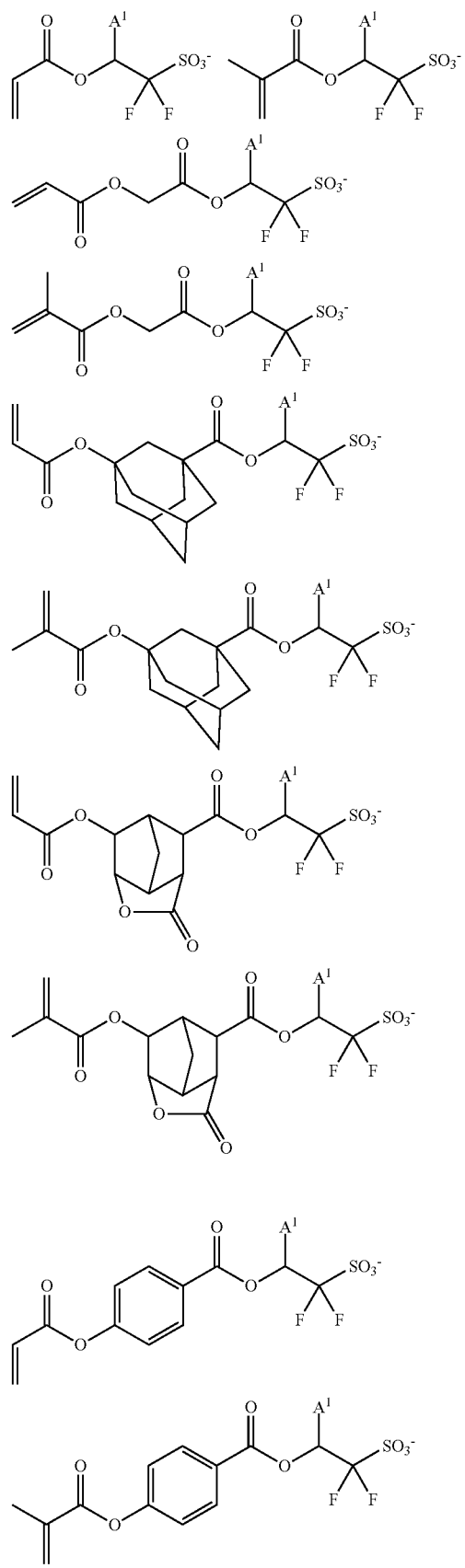

Preferred examples of the anion moiety in formula (c3) are shown below, but not limited thereto.
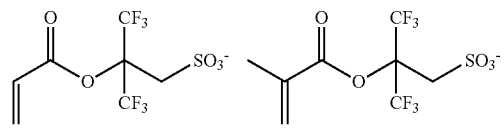
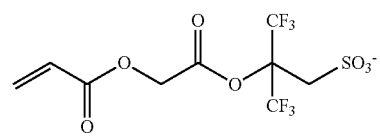
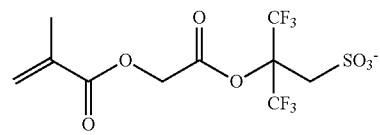
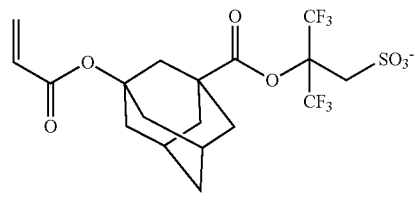
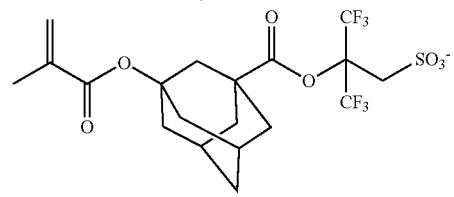
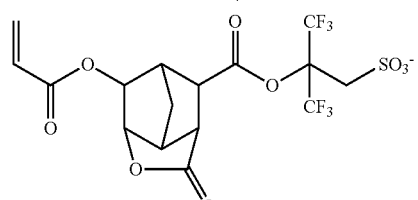
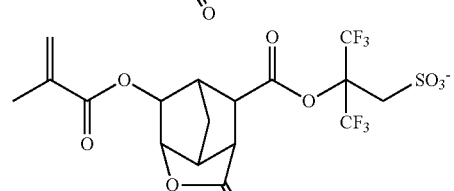
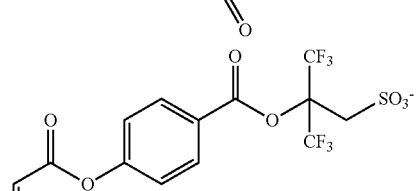
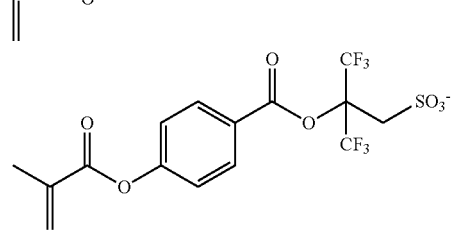
Examples of the sulfonium cation in formulae (c2) to (c4) are shown below, but not limited thereto.
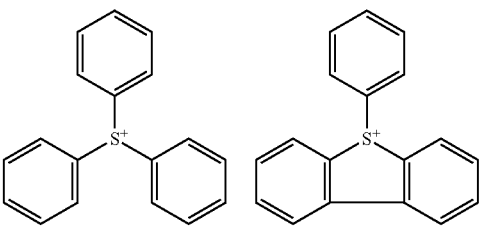
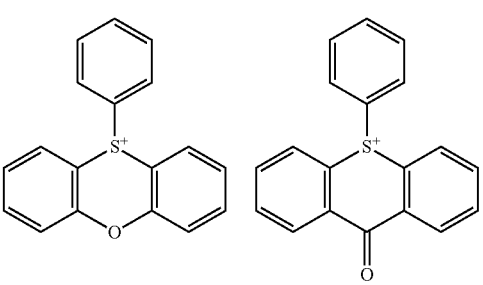
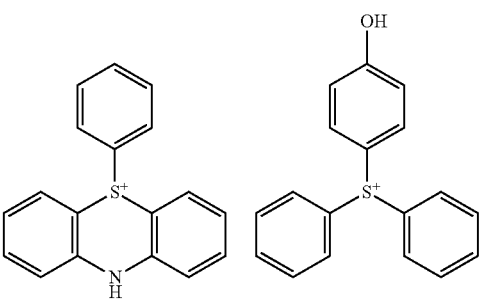
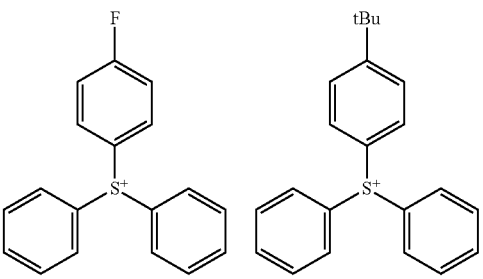
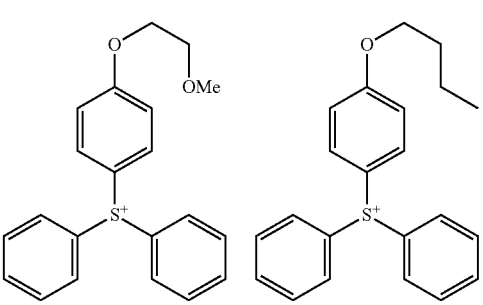

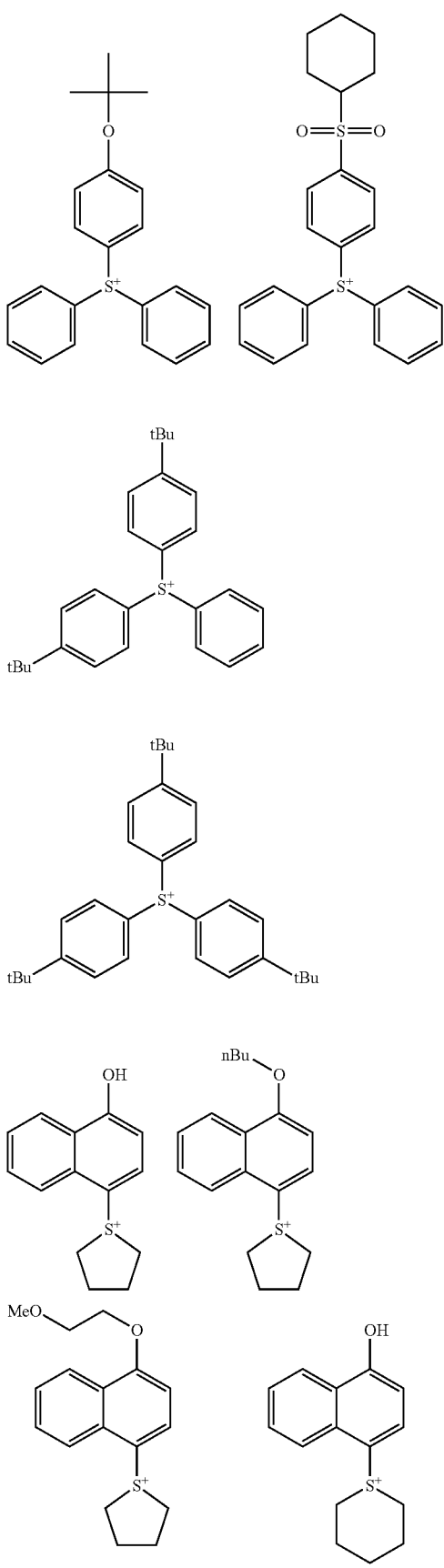
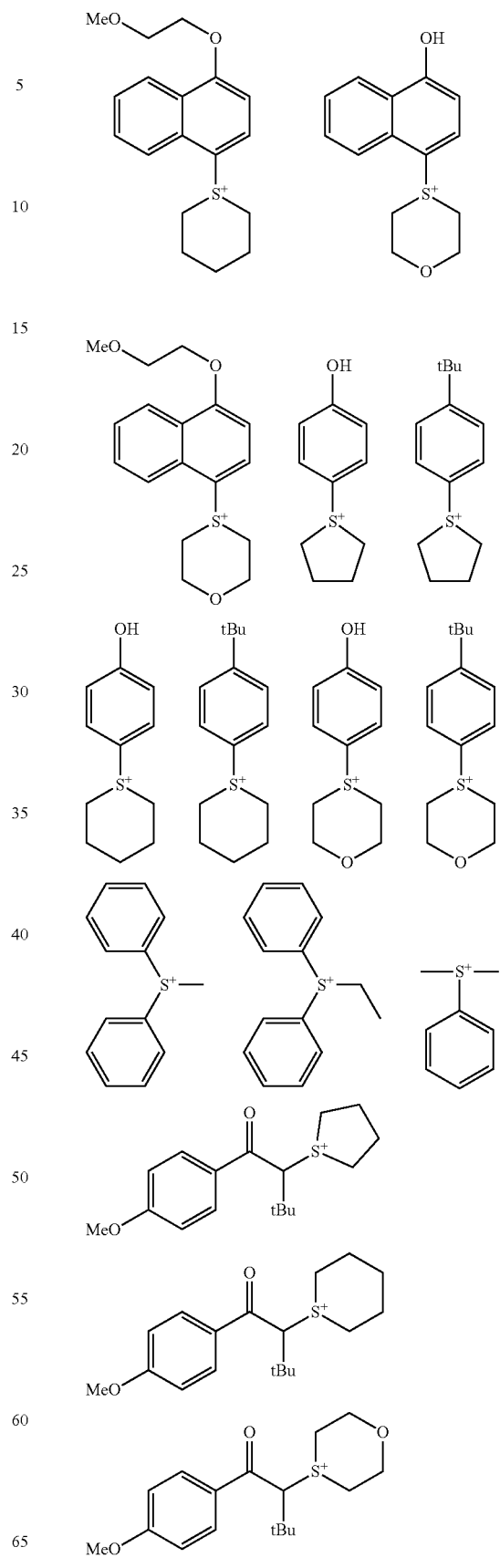

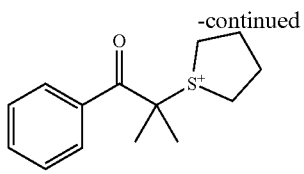

The polymer may further comprise reclining units of the structure having a hydroxyl group protected with an acid labile group. The recurring unit of the structure having a hydroxyl group protected with an acid labile group is not particularly limited as long as the unit has at least one protected hydroxyl structure wherein a hydroxyl group is resumed as a result of decomposition of the protective group under the action of acid. Such recurring units are described in JP-A 2014-225005, paragraphs [0055]-[0065] and JP-A 2015-214634, paragraphs [0110]-[0115].

The polymer may further comprise other recurring units. Typical of the other recurring units are recurring units having an oxirane or oxetane ring. A polymer comprising recurring units having an oxirane or oxetane ring is cross-linked in exposed regions, leading to improvements in retention and etching resistance of a resist film in exposed regions.

The polymer may further comprise still other recurring units, for example, units derived from substituted acrylates such as methyl methacrylate, methyl crotonate, dimethyl maleate, and dimethyl itaconate, unsaturated carboxylic acids such as maleic acid, fumaric acid, and itaconic acid, cyclic olefins such as norbornene, norbornene derivatives, tetracyclo[$6.2.1.1^{3,6}.0^{2.7}$]dodecene derivatives, unsaturated acid anhydrides such as itaconic anhydride, vinyl aromatics such as styrene, vinylnaphthalene, hydroxystyrene, hydroxyvinylnaphthalene, and 4-tert-butoxystyrene, and other monomers. Examples of the other recurring units are described in JP-A 2015-214634, paragraphs [0120]-[0132], but not limited thereto. Particularly when the resist composition is used in the EUV lithography, preferably recurring units derived from hydroxystyrene, hydroxystyrene derivatives such as o-hydroxystyrene, m-hydroxystyrene, p-hydroxystyrene, or tertiary ethers thereof are included, and more preferably recurring units derived from m-hydroxystyrene or p-hydroxystyrene are included.

The polymer should preferably have a Mw of 1,000 to 500,000, and more preferably 3,000 to 100,000. A Mw within the range eliminates any risks including an extreme drop of etching resistance, a failure to gain a difference in dissolution rate before and after exposure, and a lowering of resolution. As used herein, Mw is measured by GPC versus polystyrene standards. Also preferably the polymer has a dispersity (Mw/Mn) of 1.2 to 2.5, more preferably 1.3 to 1.8.

The polymer may be synthesized by any method, for example, by using one or more monomers corresponding to the desired recurring units in an organic solvent, adding a radical polymerization initiator, and heating for polymerization. For the polymerization method, reference should be made to U.S. Pat. No. 9,256,127 (JP-A 2015-214634, paragraphs [0134]-[0137]). The acid labile group that has been incorporated in the monomer may be kept as such, or polymerization may be followed by protection or partial protection.

While the polymer comprises recurring units derived from monomers, the molar fractions of respective units preferably fall in the following range (mol %), but are not limited thereto:

(I) 1 to 80 mol % more preferably 5 to 70 mol %, even more preferably 10 to 60 mol % of recurring units of at least one type having formula (a), (II) 20 to 99 mol %, more preferably 30 to 95 mol %, even more preferably 40 to 90 mol % of recurring units of at least one type having formula (b), and optionally.

(III) 0 to 30 mol %, more preferably 0 to 20 mol %, and even more preferably 0 to 15 mol % of recurring units of at least one type selected from formulae (c1) to (c4), and optionally, (IV) 0 to 80 mol %, more preferably 0 to 70 mol %, and even more preferably 0 to 60 mol % of recurring units of at least one type derived from another monomer(s).

In addition to the foregoing polymer, the base resin (B) may contain a hydrogenated product of ring-opening metathesis polymerization (ROMP) polymer. The hydrogenated ROMP polymer is as described in JP-A 2003-066612.

(C) Organic Solvent

Any organic solvent may be used as long as the foregoing components and other additives are soluble therein. Examples of the organic solvent are described in JP-A 2008-111103, paragraphs [0144]-[0145] (U.S. Pat. No. 7,537,880). Specifically, exemplary solvents include ketones such as cyclohexanone and methyl-2-n-pentyl ketone: alcohols such as 3-methoxybutanol, 3-methyl-3-methoxybutanol, 1-methoxy-2-propanol, 1-ethoxy-2-propanol and diacetone alcohol, ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; esters such as propylene glycol monomethyl ether acetate (PGMEA), propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, and propylene glycol mono-tert-butyl ether acetate; and lactones such as γ-butyrolactone, and mixtures thereof. Where an acid labile group of acetal form is used, a high-boiling alcohol solvent such as diethylene glycol, propylene glycol glycerol, 1,4-butanediol or 1,3-butanediol may be added for accelerating deprotection reaction of acetal. Of the above organic solvents, it is recommended to use 1-ethoxy-2-propanol, PGMEA, diacetone alcohol, cyclohexanone, γ-butyrolactone, and mixtures thereof because the acid generator is most soluble therein.

An appropriate amount of the organic solvent used is 100 to 8,000 parts, more preferably 400 to 5,000 parts by weight pet 100 parts by weight of the base resin (B).

(D) Photoacid Generator

The resist composition may comprise (D) a photoacid generator capable of generating a strong acid. As used herein, the "strong acid" is an acid having a higher acidity than the acid generated from the iodonium salt having formula (1). In the embodiment wherein the base resin (B) is adapted to change its solubility under the action of acid and contains recurring units having formula (c1), (c2), (c3) or (c4), the PAG (D) may or may not be added to the resist composition.

The PAG may be any compound capable of generating an acid upon exposure to high-energy radiation. Suitable PAGs include sulfonium salts, iodonium salts, sulfonyldiazomethanes, N-sulfonyloxydicarboxyimides. O-arylsulfonyloximes, and O-alkylsulfonyloximes. Suitable examples are described in JP-A 2007-145797, paragraphs [0102]-[0113], JP-A 2008-111103, paragraphs [0122]-[0142]. JP-A 2014-001259, paragraphs [0081]-[0092], JP-A 2012-041320, JP-A 2012-153644, JP-A 2012-106986, and JP-A 2016-

018007. The PAGs capable of generating partially fluorinated sulfonic acids described in the foregoing patent documents are preferably used in a resist composition because the strength and diffusion length of the generated acid are appropriate when the resist composition is applied to the EUV or ArF lithography. When the PAG is used in combination with the iodonium salt, the cation of the PAG is preferably selected from diphenyliodonium, p-fluorophenylphenyliodonium, tert-butylphenylphenyliodonium, and di-tert-butylphenyliodonium cations.

Sulfonium salts having the formula (2) are also preferred as the PAG (D).

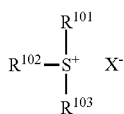
(2)

In formula (2), $R^{101}$, $R^{102}$ and $R^{103}$ are each independently a $C_1$-$C_{20}$ monovalent hydrocarbon group which may contain a heteroatom. Any two of $R^{101}$, $R^{102}$ and $R^{103}$ may bond together to form a ring with the sulfur atom to which they are attached. The monovalent hydrocarbon group is as defined and exemplified above for $R^{11}$ to $R^{21}$. Preferably at least one of $R^{101}$, $R^{102}$ and $R^{103}$ is aryl.

The sulfonium cation in formula (2) is described in JP-A 2014-001259, paragraphs [0082]-[0085]. Exemplary cations are described in JP-A 2007-145797, paragraphs [0027]-[0033], JP-A 2010-113209, paragraph [0059], JP-A 2012-041320, JP-A 2012-153644, and JP-A 2012-106986. Preferred examples of the cation in formula (2) are as exemplified above for the sulfonium cation in formulae (c2) to (c4).

In formula (2), X is an anion selected from the formulae (2A) to (2D).

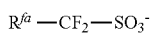
(2A)

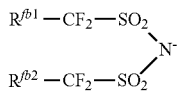
(2B)

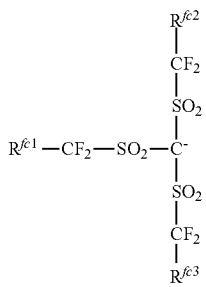
(2C)

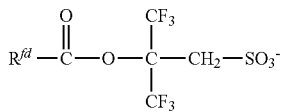
(2D)

In formula (2A), $R^{fa}$ is fluorine or a $C_1$-$C_{40}$ monovalent hydrocarbon group which may contain a heteroatom. Of the anions of formula (2A), a structure having the formula (2A') is preferred.

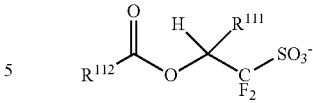
(2A')

In formula (2A), $R^{111}$ is hydrogen or trifluoromethyl, preferably trifluoromethyl. $R^{112}$ is a $C_1$-$C_{35}$ monovalent hydrocarbon group which may contain a heteroatom. Suitable heteroatoms include oxygen, nitrogen, sulfur and halogen, with oxygen being preferred. Of the monovalent hydrocarbon groups, those of 6 to 30 carbon atoms are preferred because a high resolution is available in fine pattern formation. The monovalent hydrocarbon group may be straight, branched or cyclic. Examples include straight or branched alkyl groups such as methyl, ethyl, propyl, isopropyl, butyl, isobutyl, sec-butyl, tert-butyl, pentyl, neopentyl, hexyl, heptyl, 2-ethylhexyl, nonyl, undecyl, tridecyl, pentadecyl, heptadecyl, and icosanyl; monovalent saturated cycloaliphatic hydrocarbon groups such as cyclopentyl, cyclohexyl, 1-adamantyl, 2-adamantyl, 1-adamantylmethyl, norbornyl, norbornylmethyl, tricyclodecanyl, tetracyclododecanyl, tetracyclododecanylmethyl, dicyclohexylmethyl; monovalent unsaturated aliphatic hydrocarbon groups such as allyl and 3-cyclohexenyl; and aralkyl groups such as benzyl and diphenylmethyl. Examples of the heteroatom-containing monovalent hydrocarbon group include tetrahydrofuryl, methoxymethyl, ethoxymethyl, methylthiomethyl, acetamidomethyl, trifluoromethyl, (2-methoxyethoxy)methyl, acetoxymethyl, 2-carboxy-1-cyclohexyl, 2-oxopropyl, 4-oxo-1-adamantyl, and 3-oxocyclohexyl. In these groups, some hydrogen may be substituted by a moiety containing a heteroatom such as oxygen, sulfur, nitrogen or halogen, or some carbon may be replaced by a moiety containing a heteroatom such as oxygen, sulfur or nitrogen, so that the group may contain a hydroxyl cyano, carbonyl, ether, ester, sulfonic acid ester, carbonate, lactone ring, sultone ring, carboxylic anhydride or haloalkyl moiety.

The anion having formula (2A') is described in JP-A 2007-145797, JP-A 2008-106045, JP-A 2009-007327, JP-A 2039-258695, and JP-A 2012-181306.

In formula (2B), $R^{fb1}$ and $R^{fb2}$ are each independently fluorine or a $C_1$-$C_{40}$ monovalent hydrocarbon group which may contain a heteroatom. The monovalent hydrocarbon group may be straight, branched or cyclic. Examples thereof are as exemplified for $R^{112}$. Preferably $R^{fb1}$ and $R^{fb2}$ are fluorine or $C_1$-$C_4$ straight fluorinated alkyl groups. Also, $R^{fb1}$ and $R^{fb2}$ may bond together to form a ring with the linkage: —$CF_2$—$SO_2$—$N^-$—$SO_2$—$CF_2$— to which they are attached. In this case, the combination of $R^{fb1}$ and $R^{fb2}$ is preferably a fluorinated ethylene or fluorinated propylene group.

In formula (2C), $R^{fc1}$, $R^{fc2}$ and $R^{fc3}$ are each independently fluorine or a $C_1$-$C_{40}$ monovalent hydrocarbon group which may contain a heteroatom. The monovalent hydrocarbon group may be straight, branched or cyclic. Examples thereof are as exemplified for $R^{112}$. Preferably $R^{fc1}$, $R^{fc2}$ and $R^{fc1}$ are fluorine or $C_1$-$C_4$ straight fluorinated alkyl groups. Also, $R^{fc1}$ and $R^{fc2}$ may bond together to form a ring with the linkage: —$CF_2$—$SO_2$—$C^-$—$SO_2$—$CF_2$— to which they are attached. The combination of $R^{fc1}$ and $R^{fc2}$ is preferably a fluorinated ethylene or fluorinated propylene group.

In formula (2D), $R^{fd}$ is a $C_1$-$C_{40}$ monovalent hydrocarbon group which may contain a heteroatom. The monovalent hydrocarbon group may be straight, branched or cyclic.

Examples thereof are as exemplified for $R^{112}$. The anion having formula (2D) is described in JP-A 2010-215608 and JP-A 2014-133723. Notably, the compound having the anion of formula (2D) does not have fluorine at the α-position relative to the sulfo group, but two trifluoromethyl groups at the β-position. For this reason, it has a sufficient acidity to sever the acid labile groups in the base resin. Thus the compound is an effective PAG.

Examples of the anion represented by $X^-$ are shown below, but not limited thereto. Herein "A" is hydrogen or trifluoromethyl.

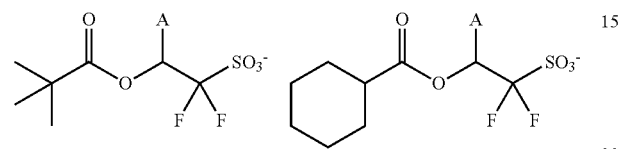
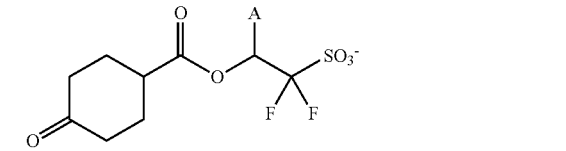
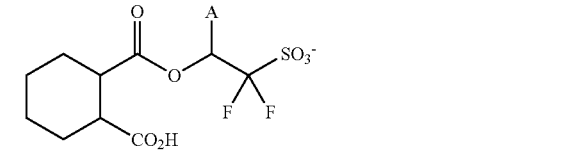
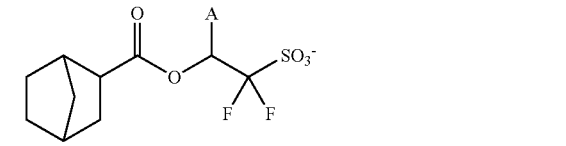
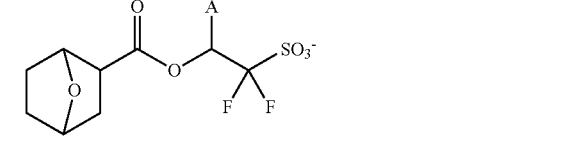
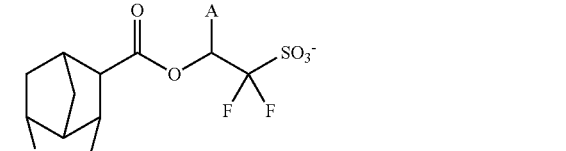
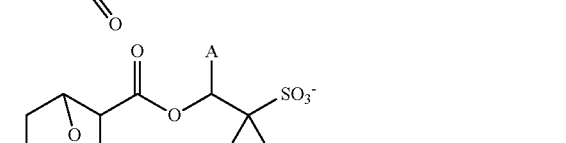
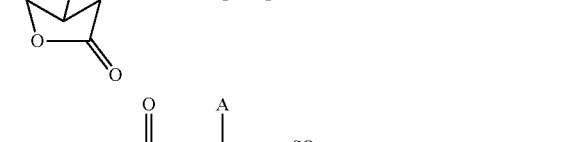
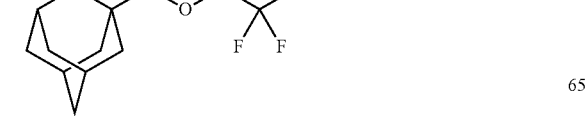

-continued

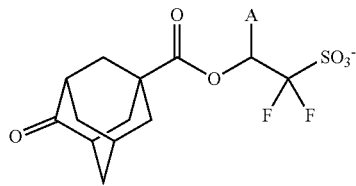
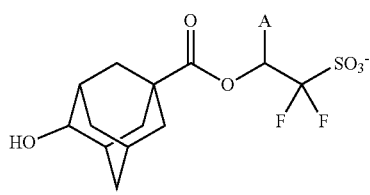
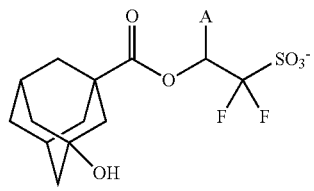
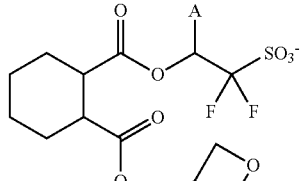
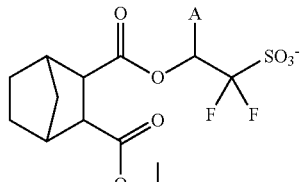
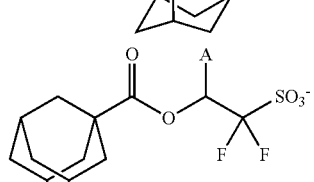
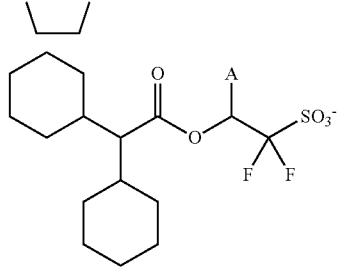

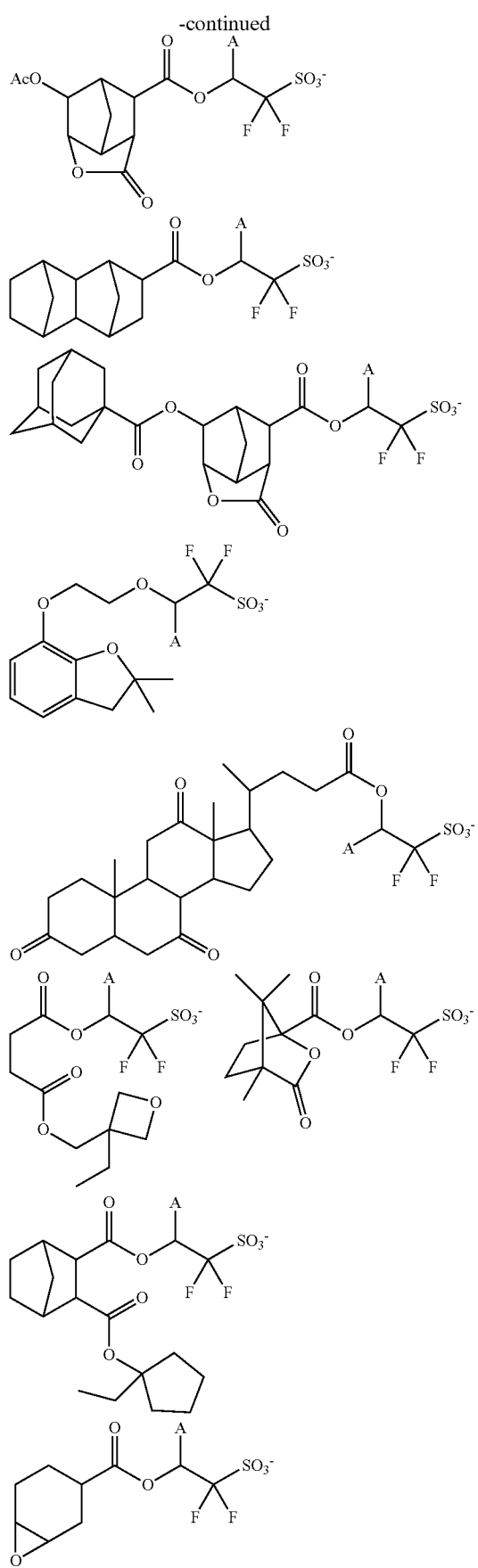

51
-continued
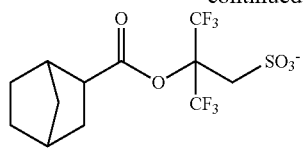
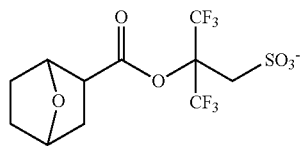
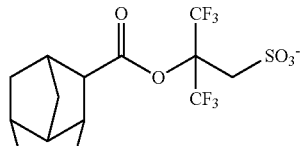
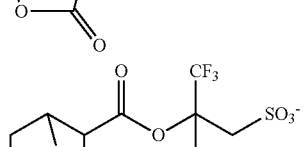
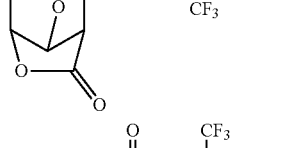
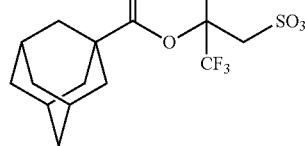
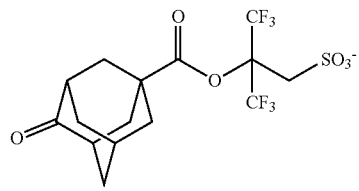
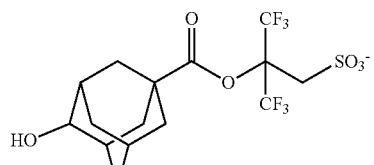
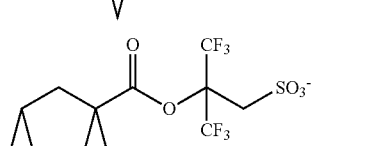
52
-continued
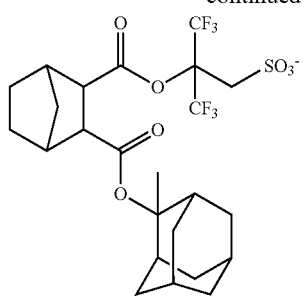
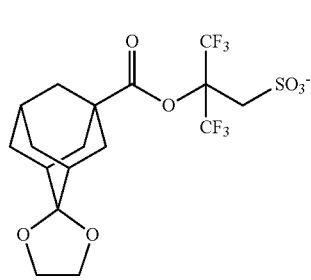
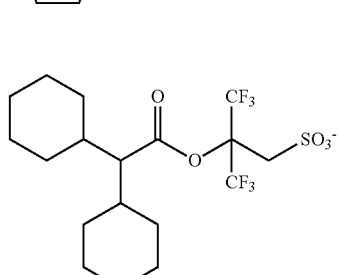
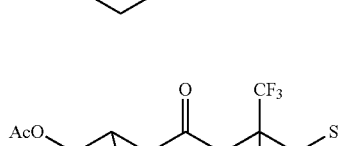
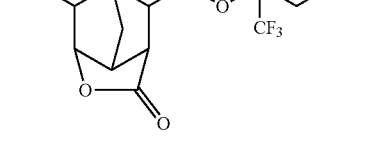
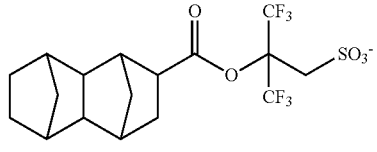
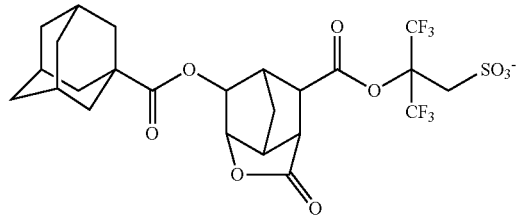
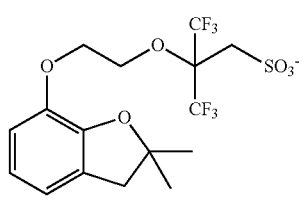

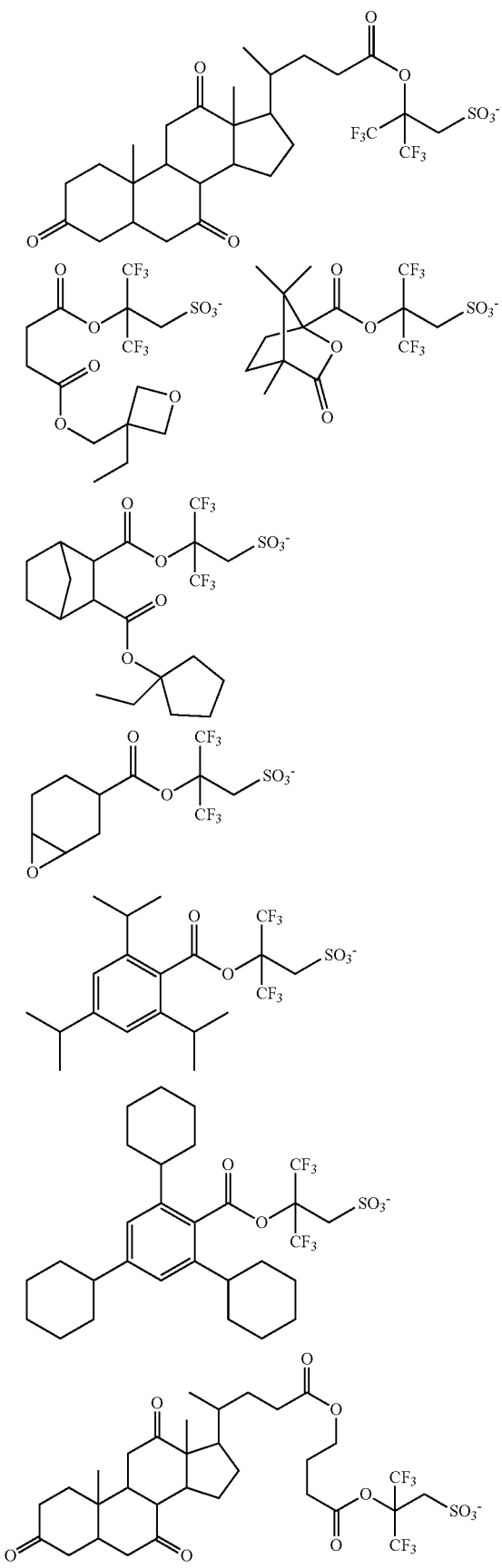

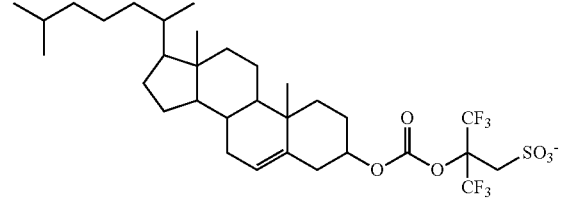

Exemplary structures of the sulfonium salt having formula (2) include arbitrary combinations of cations with anions, both as exemplified above, but are not limited thereto.

Another preferred PAG (D) is a compound having the formula (3).

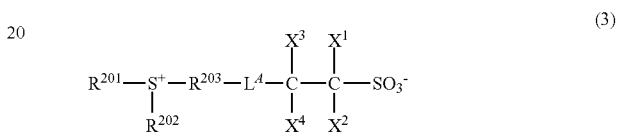

In formula (3), $R^{201}$ and $R^{202}$ are each independently a $C_1$-$C_{30}$ monovalent hydrocarbon group which may contain a heteroatom. $R^{203}$ is a $C_1$-$C_{30}$ divalent hydrocarbon group which may contain a heteroatom. Any two of $R^{201}$, $R^{202}$ and $R^{203}$ may bond together to form a ring with the sulfur atom to which they are attached. $L^A$ is a single bond, ether bond or a $C_1$-$C_{20}$ divalent hydrocarbon group which may contain a heteroatom, $X^1$, $X^2$, $X^3$ and $X^4$ are each independently hydrogen, fluorine or trifluoromethyl, with the proviso that at least one of $X^1$, $X^2$, $X^3$ and $X^4$ is fluorine or trifluoromethyl.

Among the compounds having formula (3), compounds having the formula (3') are more preferred.

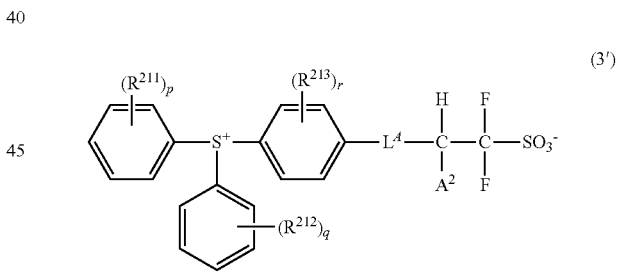

In formula (3'), $L^A$ is as defined above. $A^2$ is hydrogen or trifluoromethyl, preferably trifluoromethyl. $R^{211}$, $R^{212}$ and $R^{213}$ are each independently hydrogen or a $C_1$-$C_{20}$ straight, branched or cyclic monovalent hydrocarbon group which may contain a heteroatom, p and q are each independently an integer of 0 to 5, and r is an integer of 0 to 4.

In formula (3) or (3'), $L^A$ is preferably an ether bond or $Q_X$-O-$L^{A'}$-O-$Q_Y$ wherein $Q_X$ is a bond to benzene ring, $Q_Y$ is a bond to —CH($A^2$)—CF$_2$—SO$_3^-$, and $L^{A'}$ is a $C_1$-$C_{10}$ divalent hydrocarbon group which may contain a heteroatom.

The PAGs having formula (3) or (3') are described in JP-A 2011-016746. Examples include the sulfonium compounds described in JP-A 2011-016746 and the sulfonium compounds described in JP-A 2015-214634, paragraphs [0149]-[0150].

Examples of the PAG having formula (3) are shown below, but not limited thereto. Herein A² is as defined above.
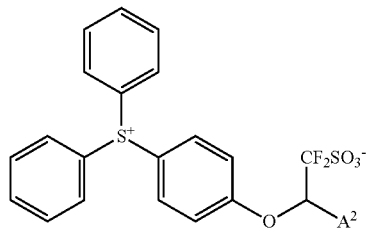
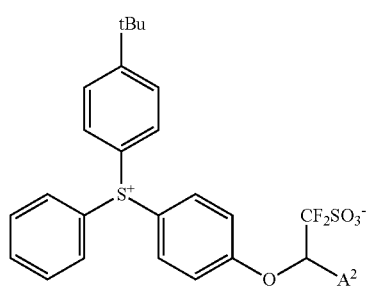
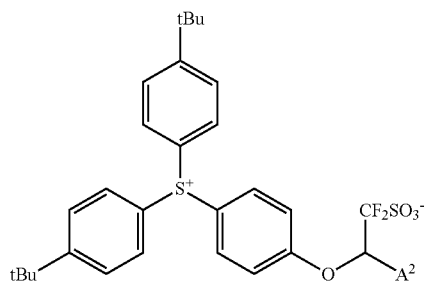
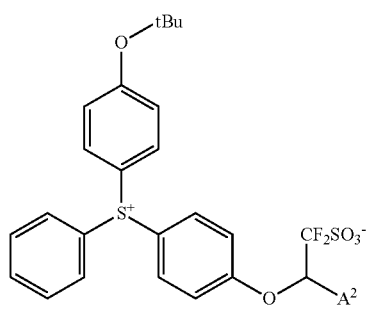
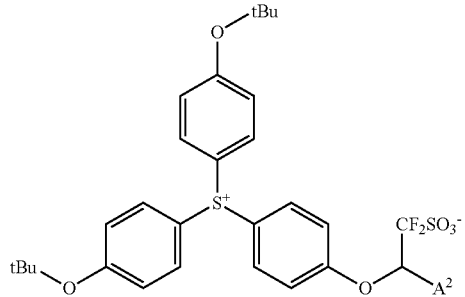
-continued
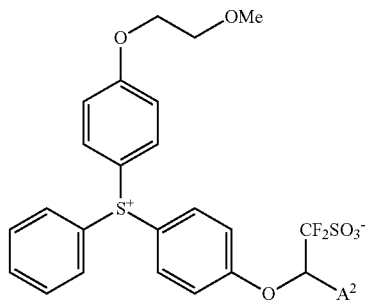
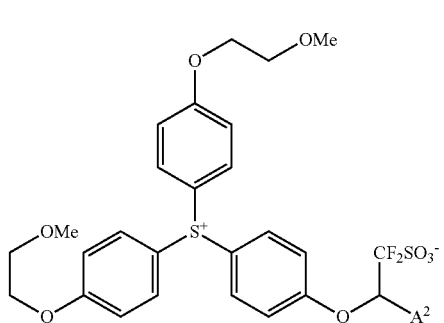
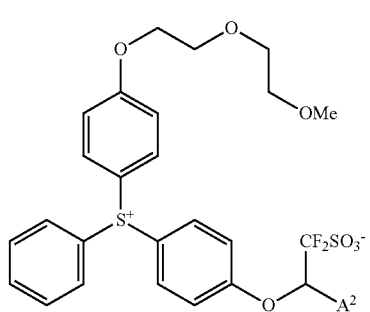
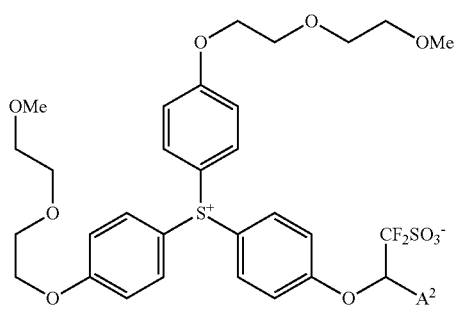
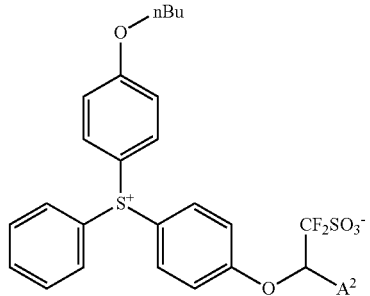

-continued

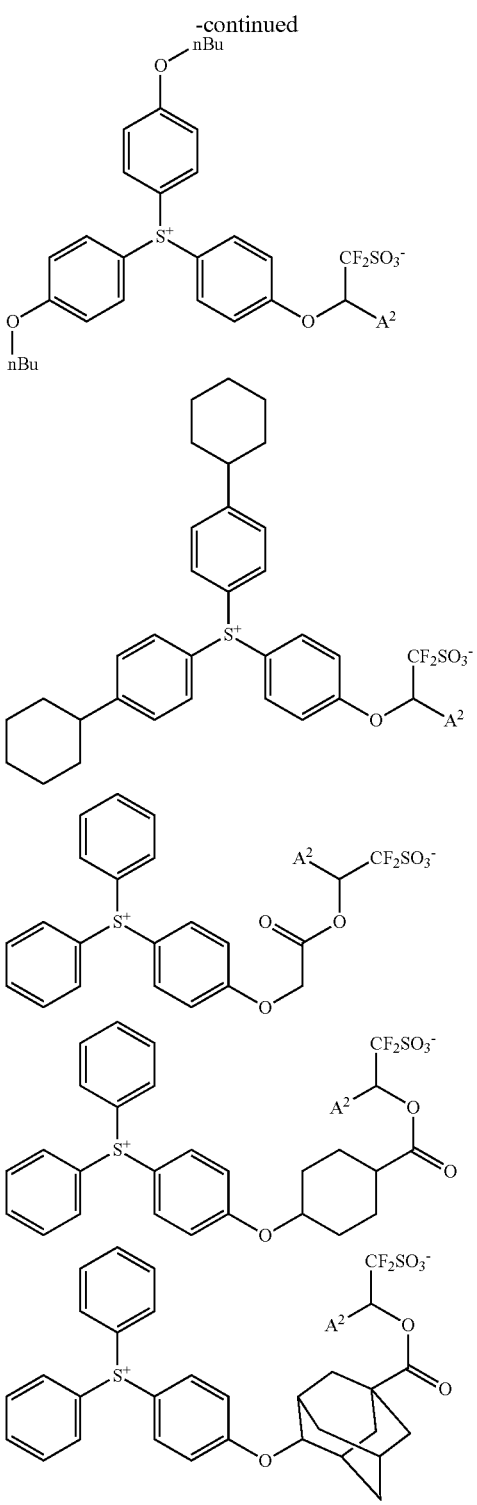

Of the foregoing PAGs, those having an anion of formula (2A') or (2D) are especially preferred because of reduced acid diffusion and high solubility in the resist solvent. Also the compounds having formula (3') are especially preferred because of extremely reduced acid diffusion.

The PAG as component (D) is preferably used in an amount of 0 to 40 parts, and when added, preferably 0.5 to 30 parts, more preferably 0.5 to 20 parts by weight per 100 parts by weight of the base resin as component (B). An amount within the range eliminates any risks including degraded resolution, and foreign particles alter resist development or during resist film stripping (E) Surfactant The resist composition may further comprise (E) a surfactant which is commonly used for facilitating coating operation. The surfactant may be used in a conventional amount. For the surfactant, reference should be made to those compounds described in JP-A 2010-215608 and JP-A 2011-016746.

Component (E) is typically a surfactant which is insoluble or substantially insoluble in water and soluble in alkaline developer, or a surfactant (hydrophobic resin) which is insoluble or substantially insoluble in water and alkaline developer.

While many examples of the surfactant which is insoluble or substantially insoluble in water and alkaline developer are described in the patent documents cited herein, preferred examples are fluorochemical surfactants FC-4430 (3M). Olfine® E1004 (Nissin Chemical Co., Ltd.), Surflon® S-381, KH-20 and KH-30 (AGO Seimi Chemical Co., Ltd.). Partially fluorinated oxetane ring-opened polymers having the formula (surf-1) are also useful.

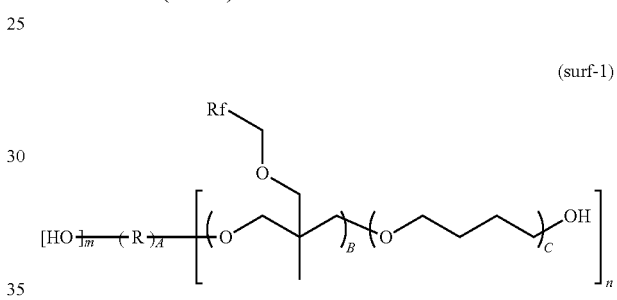

(surf-1)

It is provided herein that R, Rf, A, B, C, m, and n are applied to only formula (surf-1), independent of their descriptions other than for the surfactant. R is a di- to tetra-valent $C_2$-$C_5$ aliphatic group. Exemplary divalent aliphatic groups include ethylene, 1,4-butylene, 1,2-propylene, 2,2-dimethyl-1,3-propylene and 1,5-pentylene. Exemplary tri- and tetra-valent groups are shown below.

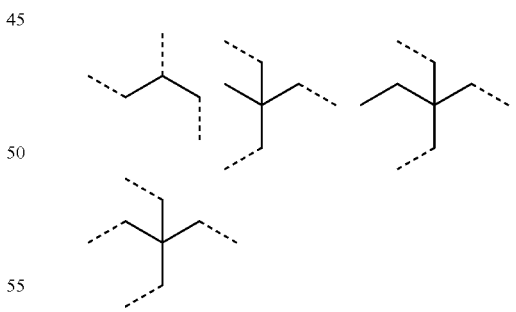

Herein the broken line denotes a valence bond. These formulae are partial structures derived from glycerol, trimethylol ethane, trimethylol propane, and pentaerythritol, respectively. Of these, 1,4-butylene and 2,2-dimethyl-1,3-propylene are preferably used.

Rf is trifluoromethyl or pentafluoroethyl, and preferably trifluoromethyl. The letter m is an integer of 0 to 3, n is an integer of 1 to 4, and the sum of m and n, which represents the valence of R, is an integer of 2 to 4. "A" is equal to 1, B is an integer of 2 to 25, and C is an integer of 0 to 10.

Preferably, B is an integer of 4 to 20, and C is 0 or 1, Note that the formula (surf-1) does not prescribe the arrangement of respective constituent units while they may be arranged either blockwise or randomly. For the preparation of surfactants in the form of partially fluorinated oxetane ring-opened polymers, reference should be made to U.S. Pat. No. 5,650,483, for example.

The surfactant which is insoluble or substantially insoluble in water and soluble in alkaline developer is useful when ArF immersion lithography is applied to the resist composition in the absence of a resist protective film. In this embodiment, the surfactant has a propensity to segregate on the resist surface after spin coating for achieving a function of minimizing water penetration or leaching. The surfactant is also effective for preventing water-soluble components from being leached out of the resist film for minimizing any damage to the exposure tool. The surfactant becomes solubilized during alkaline development following exposure and PEB, and thus forms few or no foreign particles which become defects. The preferred surfactant is a polymeric surfactant which is insoluble or substantially insoluble in water, but soluble in alkaline developer, also referred to as "hydrophobic resin" in this sense, and especially which is water repellent and enhances water sliding.

Suitable polymeric surfactants include those containing recurring units of at least one type selected from the formulae (4) to (6).

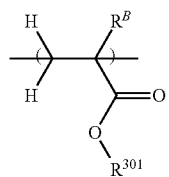

(4)

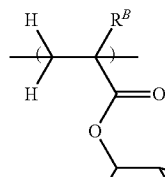

(5)

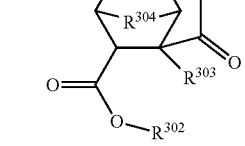

(6)

In formulae (4) to (6), $R^B$ is hydrogen, fluorine or a $C_1$-$C_4$ alkyl or fluoroalkyl group. $R^{301}$ is hydrogen, —$R^{301A}$—$CO_2H$ or —$R^{301A}$—OH wherein $R^{301A}$ is a divalent organic group which may contain a heteroatom. $R^{302}$ is a $C_2$-$C_{20}$ fluorinated alkyl group. $R^{303}$ is hydrogen, methyl or trifluoromethyl. —$R^{304}$— is a methylene group or ether bond. $R^{305}$ is a $C_2$-$C_{20}$ fluorinated alkyl group.

The $C_1$-$C_4$ alkyl or fluoroalkyl group represented by $R^B$ is preferably straight or branched. The divalent organic group represented by $R^{301A}$ is preferably a $C_1$-$C_{20}$ alkanediyl group which may contain an oxygen atom. The fluorinated alkyl group represented by $R^{302}$ or $R^{305}$ may be straight, branched or cyclic.

The polymeric surfactant preferably has a Mw of 1,000 to 500,000, more preferably 2,000 to 30,000.

In the polymeric surfactant, provided that x is a proportion (mol %) of recurring units having formula (4), y is a proportion (mol %) of recurring units having formula (5), and z is a proportion (mol %) of recurring units having formula (6), x, y and z are preferably in the range: $0 \le x < 1$, $0 < y < 1$, $0 \le z < 1$, and $0 < x+y+z \le 1$.

For the polymeric surfactant, reference may be made to JP-A 2007-297590, 2008-088343, 2008-122932, 2009-098638, 2009-191151, 2009-192784, 2009-276363, 2010-107695, 2010-134012, 2010-250105, and 2011-042789.

The polymeric surfactant is preferably formulated in an amount of 0.001 to 20 parts, and more preferably 0.01 to 10 parts by weight per 100 parts by weight of the base resin (B).

(F) Quencher Other than Component (A)

To the resist composition, there may be added (F) a quencher other than component (A), that is a quencher other than the iodonium salt having formula (1). As used herein, the "quencher" refers to a compound capable of suppressing the rate of diffusion when the acid generated by the PAG diffuses within the resist film.

Suitable quenchers include amine compounds, typically primary, secondary and tertiary amine compounds, specifically amine compounds having a hydroxyl group, ether bond, ester bond, lactone ring, cyano group or sulfonate bond, as described in JP-A 2008-111103, paragraphs [0146]-[0164] (U.S. Pat. No. 7,537,880), and primary or secondary amine compounds having a carbamate group, as described in JP 3790649. Such a protected amine compound is effective particularly when the resist composition contains a base-labile component.

Other examples of the quencher (F) include a compound (i.e., onium salt of sulfonic acid which is not fluorinated at α-position) having the formula (7), and a compound (i.e., onium salt of carboxylic acid) having the formula (8).

$$R^{401}\text{—}SO_3^- \ Mq^+ \quad (7)$$

$$R^{402}\text{—}CO_2^- \ Mq^+ \quad (8)$$

In formula (7), $R^{401}$ is hydrogen or a $C_1$-$C_{40}$ monovalent hydrocarbon group which may contain a heteroatom, exclusive of the group wherein hydrogen bonded to the carbon atom at α-position relative to the sulfo group is substituted by fluorine or fluoroalkyl. The monovalent hydrocarbon groups include alkyl, alkenyl, aryl, aralkyl, and aryloxyalkyl groups. Suitable alkyl groups include methyl, ethyl, propyl, isopropyl, n-butyl, sec-butyl, tert-butyl, tert-pentyl, n-pentyl, n-hexyl, n-octyl, n-nonyl, n-decyl, cyclopentyl, cyclohexyl, 2-ethylhexyl, cyclopentylmethyl, cyclopentylethyl, cyclopentylbutyl, cyclohexylmethyl, cyclohexylethyl, cyclohexylbutyl, norbornyl, tricyclo[5.2.1.0$^{2,6}$]decanyl, adamantyl, and adamantylmethyl. Suitable alkenyl groups include vinyl, allyl, propenyl, butenyl, hexenyl, and cyclohexenyl. Suitable alkenyl groups include phenyl, naphthyl, thienyl, 4-hydroxyphenyl, alkoxyphenyl groups such as 4-methoxyphenyl, 3-methoxyphenyl, 2-methoxyphenyl, 4-ethoxyphenyl, 4-tert-butoxyphenyl, and 3-tert-butoxyphenyl; alkylphenyl groups such as 2-methylphenyl, 3-methylphenyl, 4-methylphenyl, 4-ethylphenyl, 4-tert-butylphenyl, 4-n-butylphenyl, 2,4-dimethylphenyl, and 2,4,6-triisopropylphenyl; alkylnaphthyl groups such as methylnaphthyl and ethylnaphthyl; alkoxynaphthyl groups such as methoxynaphthyl, ethoxynaphthyl, n-propoxynaphthyl and n-butoxynaphthyl; dialkylnaphthyl groups such as dimethylnaphthyl and diethylnaphthyl; and dialkoxynaphthyl groups such as dimethoxynaphthyl and diethoxynaphthyl. Suitable aralkyl groups include benzyl, 1-phenylethyl and 2-phenylethyl. Suitable aryloxoalkyl groups include 2-aryl-2-oxoethyl groups such as 2-phenyl-2-oxoethyl, 2-(1-naphthyl)-2-oxoethyl, and 2-(2-naphthyl)-2-oxoethyl. In these groups, some hydrogen may be substituted by a moiety containing a heteroatom such as oxygen, sulfur, nitrogen or halogen, and some carbon may be replaced by a moiety containing a heteroatom such as oxygen, sulfur or nitrogen, so that the group may contain a hydroxyl moiety, cyano moiety, carbonyl moiety, ether bond, ester bond, sulfonic acid ester bond, carbonate bond, lactone ring, sultone ring, carboxylic anhydride, or haloalkyl moiety.

In formula (8), $R^{402}$ is a $C_1$-$C_{40}$ monovalent hydrocarbon group which may contain a heteroatom. Examples of the monovalent hydrocarbon group $R^{402}$ are as exemplified above for the monovalent hydrocarbon group $R^{401}$. Also included are fluorinated alkyl groups such as trifluoromethyl, trifluoroethyl, 2,2,2-trifluoro-1-methyl-1-hydroxyethyl, 2,2,2-trifluoro-1-(trifluoromethyl)-1-hydroxyethyl, aryl groups such as phenyl, tolyl, xylyl, 4-tert-butylphenyl, and naphthyl, and fluorinated aryl groups such as pentafluorophenyl and 4-trifluoromethylphenyl.

For the sulfonic acid onium salt having formula (7) and the carboxylic acid onium salt having formula (8), reference should be made to JP-A 2008-158339 and JP-A 2010-155824.

Preferred examples of the anion in formula (7) are shown below, but not limited thereto.

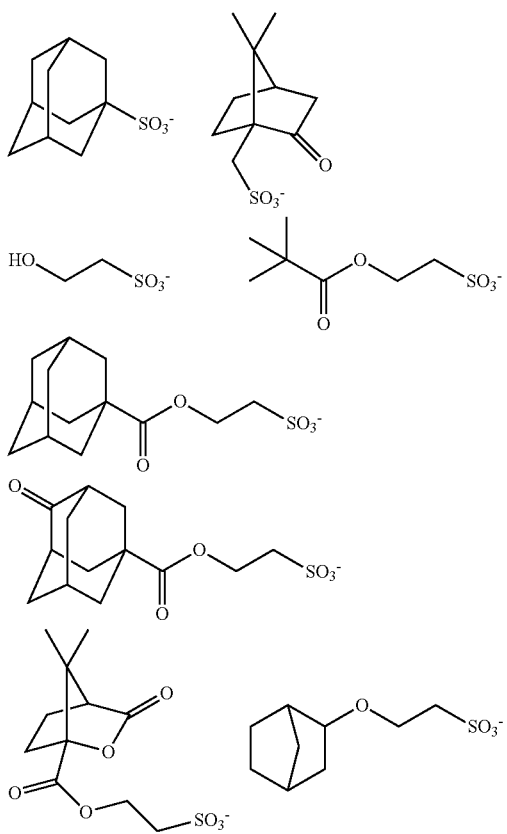

-continued

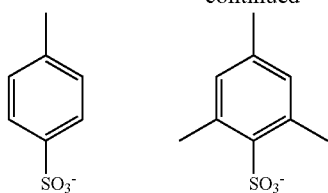

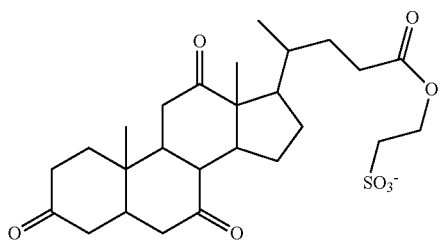

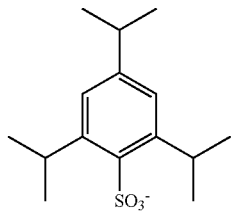

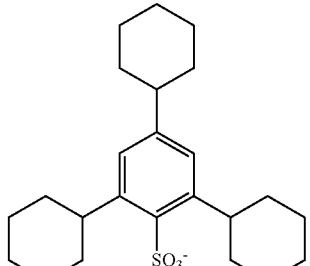

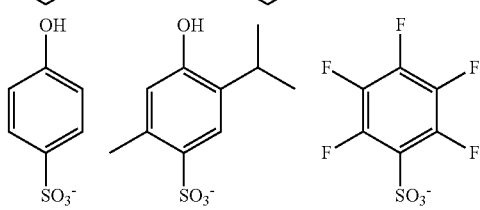

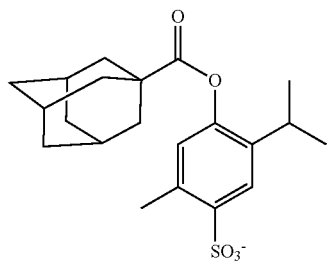

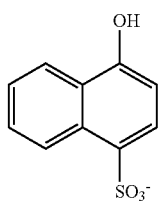

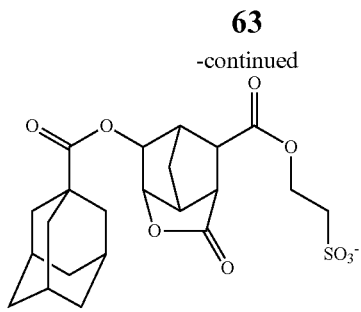
Preferred examples of the anion in formula (8) are shown below, but not limited thereto.
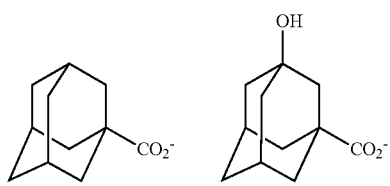
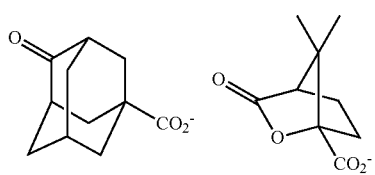
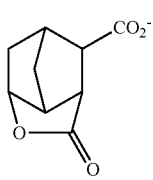
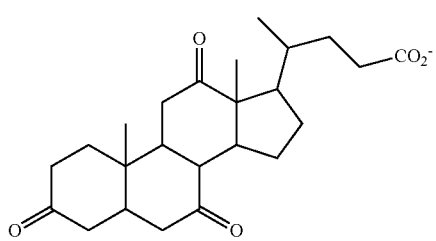
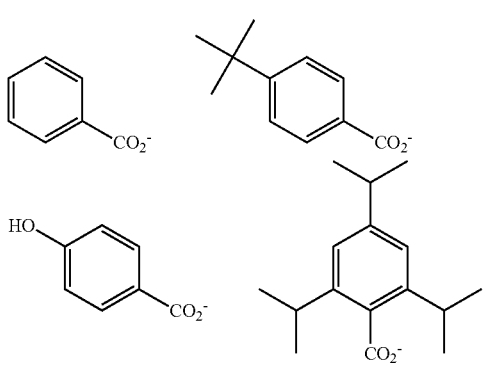
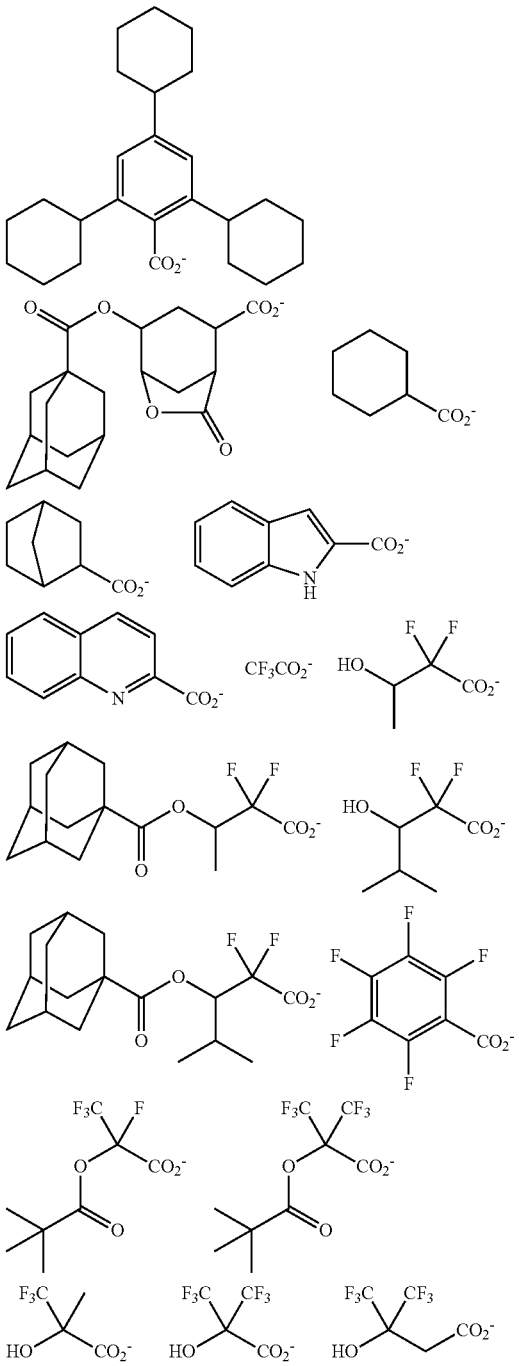
In formulae (7) and (8), $M_q^+$ is an onium cation, which is preferably selected from cations having the formulae (9) to (11).
$$\begin{array}{c} R^{411} \\ | \\ S^+ - R^{412} \\ | \\ R^{413} \end{array} \quad (9)$$
$$R^{414} - I^+ - R^{415} \quad (10)$$

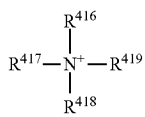

(11)

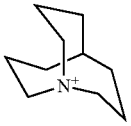

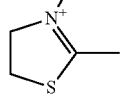

In formulae (9) to (11), $R^{411}$ to $R^{419}$ are each independently a $C_1$-$C_{40}$ monovalent hydrocarbon group which may contain a heteroatom. A pair of $R^{411}$ and $R^{412}$, or $R^{416}$ and $R^{417}$ may bond together to form a ring with the sulfur or nitrogen atom to which they are attached.

Examples of the sulfonium cation having formula (9) are as exemplified above as the cation in formulae (c2) to (c4). Examples of the iodonium cation having formula (10) are as exemplified above as the cation in the iodonium salt having formula (1). Examples of the ammonium cation having formula (11) are shown below, but not limited thereto.

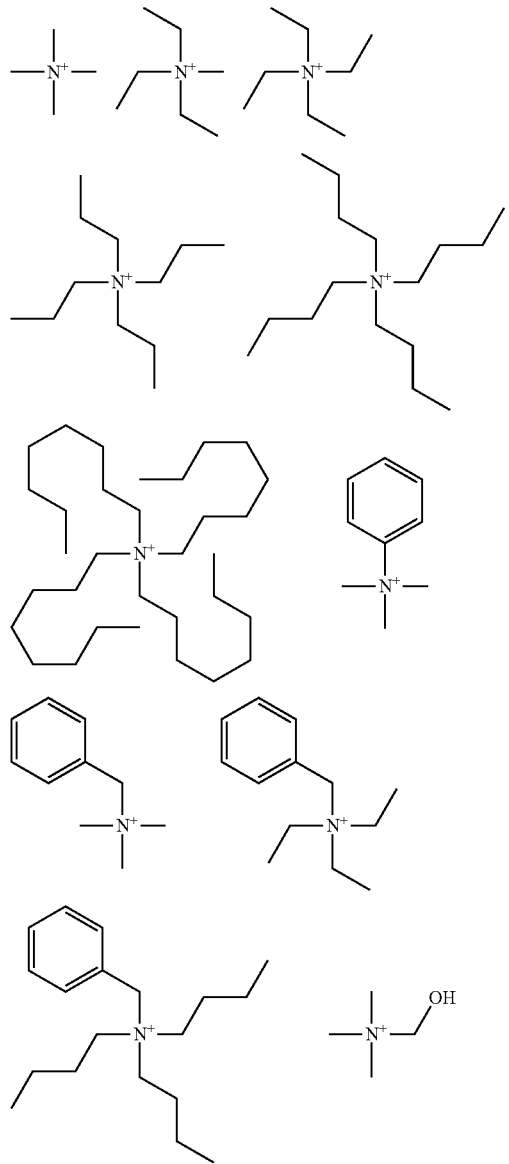

Exemplary structures of the onium salt having formula (7) or (8) include arbitrary combinations of anions with cations, both as exemplified above. These onium salts may be readily obtained from ion exchange reaction using any well-known organic chemistry technique. For the ion exchange reaction, reference may be made to JP-A 2007-145797, for example.

The anion in formula (7) or (8) is a conjugated base of weak acid. As used herein, the weak acid indicates an acidity insufficient to deprotect an acid labile group from an acid labile group-containing unit in the base resin. The onium salt having formula (7) or (8) functions as a quencher when used in combination with an onium salt type PAG having a conjugated base of a strong acid (typically a sulfonic acid which is fluorinated at α-position) as the counter anion. In a system using a mixture of an onium salt capable of generating a strong acid (e.g., α-position fluorinated sulfonic acid) and an onium salt capable of generating a weak acid (e.g., α-position non-fluorinated sulfonic acid or carboxylic acid), if the strong acid generated from the PAG upon exposure to high-energy radiation collides with the unreacted onium salt having a weak acid anion, then a salt exchange occurs whereby the weak acid is released and an onium salt having a strong acid anion is formed. In this course, the strong acid is exchanged into the weak acid having a low catalysis, inclining apparent deactivation of the acid for enabling to control acid diffusion.

In particular, since the onium salt having formula (7) or (8) wherein $Mq^+$ is a sulfonium cation having formula (9) or an iodonium cation having formula (10) is photo-decomposable, those portions receiving a high light intensity are reduced in quenching capability and increased in the concentration of a strong acid originating from the PAG. This enables to form a pattern having an improved contrast in exposed area, a further improved depth of focus (DOF) and satisfactory dimensional control.

If a PAG capable of generating a strong acid is an onium salt, an exchange from the strong acid generated upon exposure to high-energy radiation to a weak acid as above can take place, but it never happens that the weak acid generated upon exposure to high-energy radiation collides with the unreacted onium salt capable of generating a strong acid to induce a salt exchange. This is because of a likelihood of an onium cation forming an ion pair with a stronger acid anion.

While the inventive iodonium salt mainly functions as a quencher, various lithography performance factors are improved by the aforementioned effects.

In case the acid labile group is an acetal group which is very sensitive to acid, the acid for eliminating the protective group need not necessarily be an α-fluorinated sulfonic acid, imide acid or methide acid. Sometimes, deprotection reaction may take place even with α-position non-fluorinated sulfonic acid. In this case, an onium salt of carboxylic acid having formula (8) is preferably used as the quencher.

As the quencher or component (F), quenchers of betaine type may be used as well as the aforementioned quenchers of onium salt type. Suitable betaine type quenchers include well-known compounds such as diphenyliodonium-2-carboxylate.

Also, a photo-decomposable onium salt having a nitrogen-containing substituent may be used as the quencher or component (F). This compound functions as a quencher in the unexposed region, but as a so-called photo-degradable base in the exposed region because it loses the quencher function in the exposed region due to neutralization thereof with the acid generated by itself. Using a photo-degradable base, the contrast between exposed and unexposed regions can be further enhanced. With respect to the photo-degradable base, reference may be made to JP-A 2009-109595, 2012-046501 and JP-A 2013-209360, for example.

The amount of component (F) used is preferably 0 to 40 parts by weight, and when added. 0.1 to 40 parts by weight, more preferably 0.5 to 20 parts by weight per 100 parts by weight of the base resin (B). As long as the amount of component (F) is up to 40 parts, the problem of foreign particles after resist development or during stripping is avoided. The inclusion of the quencher facilitates adjustment of resist sensitivity and holds down the rate of acid diffusion within the resist film, resulting in better resolution. In addition, it suppresses changes in sensitivity following exposure and reduces substrate and environment dependence, as well as improving the exposure latitude and the pattern profile. The inclusion of the quencher is also effective for improving adhesion to the substrate. The quencher (F) may be used alone or in admixture.

(G) Other Components

The resist composition may further comprise (G) another component, for example, a compound which is decomposed with an acid to generate another acid (i.e., acid amplifier compound), an organic acid derivative, a fluorinated alcohol, a crosslinker, a compound having a Mw of up to 3,000 which changes its solubility in developer under the action of an acid (i.e., dissolution inhibitor), and an acetylene alcohol. Specifically, the acid amplifier compound is described in JP-A 2009-269953 and JP-A 2010-215608 and preferably used in an amount of 0 to 5 parts, more preferably 0 to 3 parts by weight per 100 parts by weight of the base resin (B). An amount of the acid amplifier compound in the range makes the acid diffusion control easy and causes no degradations to resolution and pattern profile. With respect to the remaining additives, reference should be made to JP-A 2008-122932, paragraphs [0155]-[0182], JP-A 2009-269953, and JP-A 2010-215608.

Process

A further embodiment of the invention is a pattern forming process using the resist composition defined above. A pattern may be formed from tire resist composition using any well-known lithography process. The preferred process includes the steps of applying the resist composition onto a substrate to form a resist film, exposing a selected region of the resist film to KrF excimer laser, ArF excimer laser, EB or EUV, and developing the exposed resist film in a developer. Any desired steps may be added to the process if necessary.

The substrate used herein may be a substrate for integrated circuitry fabrication, e.g., Si, $SiO_2$, SiN, SiON, TiN, WSi, BPSG, SOG, organic antireflective film, etc. or a substrate for mask circuitry fabrication, e.g., Cr, CrO, CrON, $MoSi_2$, $SiO_2$, etc.

The resist composition is applied onto a substrate by a suitable coating technique such as spin coating. The coating is prebaked on a hot plate at a temperature of 60 to 180° C. for 10 to 600 seconds, preferably at 70 to 150° C. for 15 to 300 seconds. The resulting resist film preferably has a thickness of 10 to 2,000 nm, more preferably 20 to 500 nm.

Then the resist film is exposed patternwise to excimer laser, EUV or EB. On use of KrF excimer laser, ArF excimer laser or EUV of wavelength 13.5 nm, the resist film is exposed through a mask having a desired pattern, preferably in a dose of 1 to 200 $mJ/cm^2$, more more preferably 10 to 100 $mJ/cm^2$. On use of EB, a pattern may be written directly or through a mask having the desired pattern, preferably in a dose of 1 to 300 $\mu C/cm^2$, more preferably 10 to 200 $\mu C/cm^2$.

The exposure may be performed by conventional lithography whereas the immersion lithography of holding a liquid between the mask and the resist film may be employed if desired. In the immersion lithography, preferably a liquid having a refractive index of at least 1.0 is held between the resist film and the projection lens. The liquid is typically water, and in this case, a protective film which is insoluble in water may be formed on the resist film.

While the water-insoluble protective film which is used in the immersion lithography serves to prevent any components from being leached out of the resist film and to improve water sliding on the film surface, it is generally divided into two types. The first type is an organic solvent-strippable protective film which mast be stripped, prior to alkaline development, with an organic solvent in which the resist film is not dissolvable. The second type is an alkali-soluble protective film which is soluble in an alkaline developer so that it can be removed simultaneously with the removal of solubilized regions of the resist film. The protective film of the second type is preferably of a material comprising a polymer having a 1,1,1,3,3,3-hexafluoro-2-propanol residue (which is insoluble in water and soluble m an alkaline developer) as a base in an alcohol solvent of at least 4 carbon atoms, an ether solvent of 8 to 12 carbon atoms or a mixture thereof. Alternatively, the aforementioned surfactant which is insoluble in water and soluble in an alkaline developer may be dissolved in an alcohol solvent of at least 4 carbon atoms, an ether solvent of 8 to 12 carbon atoms or a mixture thereof to form a material from which the protective film of the second type is formed.

After the exposure, the resist film may be baked (PEB), for example, on a hotplate at 60 to 150° C. for 1 to 5 minutes, preferably at 80 to 140° C. for 1 to 3 minutes.

The resist film is then developed with a developer in the form of an aqueous base solution, for example, 0.1 to 5 wt %, preferably 2 to 3 wt % aqueous solution of tetramethylammonium hydroxide (TMAH) or an organic solvent developer for 0.1 to 3 minutes, preferably 0.5 to 2 minutes by conventional techniques such as dip, puddle and spray techniques. In this way, a desired resist pattern is formed on the substrate.

With respect to the developer used in the pattern forming process of the invention, the aqueous base solution may be the above-mentioned aqueous solution of TMAH or another aqueous base solution as described in JP-A 2015-180748, paragraphs [0148-0149]. A 2 to 3 wt % aqueous solution of TMAH is preferred.

In the organic solvent development, the organic solvent used as the developer is preferably selected from 2-octanone, 2-nonanone, 2-heptanone, 3-heptanone, 4-heptanone, 2-hexanone, 3-hexanone, diisobutyl ketone, methylcyclohexanone, acetophenone, methylacetophenone, propyl acetate, butyl acetate, isobutyl acetate, pentyl acetate, isopentyl acetate, butenyl acetate, propyl formate, butyl formate, isobutyl formate, pentyl formate, isopentyl formate, methyl valerate, methyl pentenoate, methyl crotonate, ethyl crotonate, methyl propionate, ethyl propionate, ethyl 3-ethoxypropionate, methyl lactate, ethyl lactate, propyl lactate, butyl lactate, isobutyl lactate, pentyl lactate, isopentyl lactate, methyl 2-hydroxyisobutyrate, ethyl 2-hydroxyisobutyrate, methyl benzoate, ethyl benzoate, phenyl acetate, benzyl acetate, methyl phenylacetate, benzyl formate, phenylethyl formate, methyl 3-phenylpropionate, benzyl propionate, ethyl phenylacetate, and 2-phenylethyl acetate. These organic solvents may be used alone or in admixture of two or more.

Any desired step may be added to the pattern forming process. For example, after the resist film is formed, a step of rinsing with pure water (post-soaking) may be introduced to extract the acid generator or the like from the film surface or wash away particles. After exposure, a step of rinsing (post-soaking) may be introduced to remove any water remaining on the film after exposure.

Also, a double patterning process may be used for pattern formation. The double patterning process includes a trench process of processing an underlay to a 1:3 trench pattern by a first step of exposure and etching, shifting the position, and forming a 1:3 trench pattern by a second step of exposure, for forming a 1:1 pattern; and a line process of processing a first underlay to a 1:3 isolated left pattern by a first step of exposure and etching, shifting the position, processing a second under lay formed below the first underlay by a second step of exposure through the 1:3 isolated left pattern, for forming a hall-pitch 1:1 pattern.

Where a hole pattern is formed by negative tone development using organic solvent developer, exposure by double dipole illuminations of X- and Y-direction line patterns provides the highest contrast light. The contrast may be further increased by combining two dipole illuminations of X- and Y-direction line patterns with s-polarized illumination. These pattern forming processes are described in JP-A 2011-221513.

A hole or trench pattern after development may be shrunk by the thermal flow, resolution enhancement lithography assisted by chemical shrink (RELACS) or directed self-assembly (DSA) process. A hole pattern is shrunk by coating a shrink agent thereto, and baking such that the shrink agent may undergo crosslinking at the resist surface as a result of the acid catalyst diffusing from the resist layer during bake, and the shrink agent may attach to the sidewall of the hole pattern. The bake is at a temperature of 70 to 180° C., preferably 80 to 170° C., for a time of 10 to 300 seconds. The extra shrink agent is stripped and the hole pattern is shrunk.

By the pattern forming process using the resist composition comprising the inventive iodonium salt, a fine size pattern which is improved in lithography performance factors including rectangularity, MEF, CDU, and LWR can be readily formed.

EXAMPLE

Examples and Comparative Examples are given below by way of illustration and not by way of limitation. All parts are by weight (pbw). For all polymers, Mw and Mn are determined by GPC versus polystyrene standards using tetrahydrofuran (THF) solvent. Analysis is made by time-of-flight mass spectrometry (TOFMS), $^1$H- and $^{19}$F-NMR spectroscopy.

[1] Synthesis of Intermediate

Synthesis Example 1

Synthesis of Anion Intermediate C-1

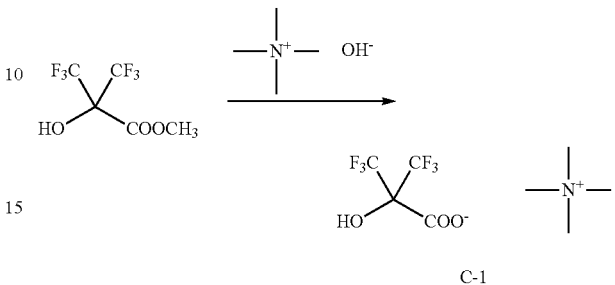

A flask was charged with 260.8 g of a 25 wt % aqueous solution of tetramethylammonium hydroxide. With stirring at room temperature, 154.0 g of methyl 3,3,3-trifluoro-2-hydroxy-2-(trifluoromethyl)propionate was added dropwise. At the end of addition, the solution was heated at 40° C. and aged, with stirring, at the temperature overnight. After the progress of reaction was confirmed by $^{19}$F-NMR spectroscopy, 80 g of toluene was added to the reaction solution, which was stirred. The water layer was taken out and washed with 80 g of toluene, obtaining an aqueous solution of the desired anion intermediate C-1. Concentration 1.48 mmol/g.

[2] Synthesis of Iodonium Salt

Example 1-1

Synthesis of Iodonium Salt I-1

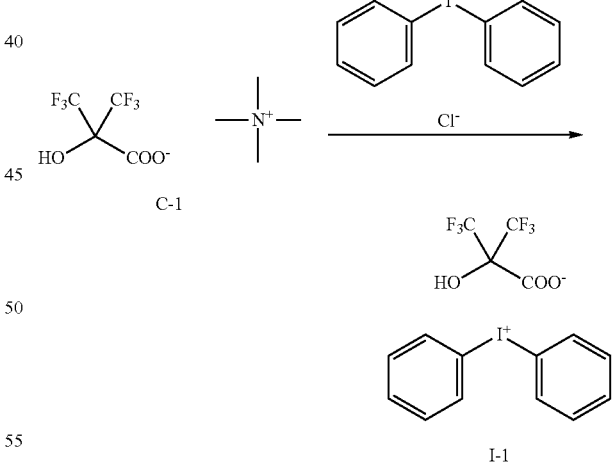

After 6.3 g of diphenyliodonium chloride, 16.2 g of the aqueous solution of anion intermediate C-1, 60 g of methylene chloride, 8 g of methanol, 12 g of 1-pentanol, and 16 g of deionized water were mixed and stirred for 1 hour, the organic layer was taken out. To the organic layer, 1.4 g of the aqueous solution of anion intermediate C-1 and 20 g of deionized water were added and stirred, after which the organic layer was taken out. The organic layer was further washed once with 20 g of deionized water, 3 times with 25 g of 25 wt % methanol aqueous solution, and once with 20 g of deionized water. The organic layer was concentrated under reduced pressure to remove methylene chloride, after which 56 g of diisopropyl ether was added and stirred for crystallization. The resulting solid was filtered, rinsed with diisopropyl ether, and dried at 40° C. under reduced pressure, obtaining 5.5 g (yield 56%) of the target iodonium salt I-1.

$^1$H-NMR (500 MHz, DMSO-$d_6$):

δ=6.34 (1H, s), 7.52 (4H, m), 7.66 (2H, m), 8.24 (4H, m) ppm $^{19}$F-NMR (500 MHz, DMSO-$d_6$):

δ=−74.6 (6F, s) ppm

TOFMS (MALDI)

Positive M$^+$ 281 (corresponding to $C_{12}H_{10}I^+$)

Negative M$^-$ 211 (corresponding to $C_4HF_6O_3^-$)

Example 1-2

Synthesis of Iodonium Salt 1-2

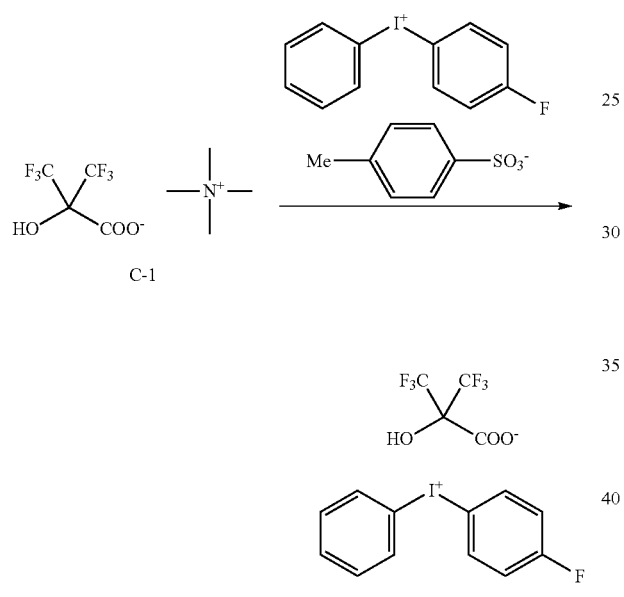

I-2

After 8.3 g of (4-fluorophenyl)phenyliodonium p-toluenesulfonate (known compound), 16.8 g of the aqueous solution of anion intermediate C-1, 63 g of 1-pentanol, 20 g of methanol, and 20 g of deionized water were mixed and stirred for 4 hours, the organic layer was taken out. The procedure of adding 1.8 g of the aqueous solution of anion intermediate C-1 and 10 g of deionized water to the organic layer, stirring the mixture, and taking out the organic layer was repeated 5 times. The organic layer was further washed 5 times with 10 g of deionized water. The organic layer was concentrated under reduced pressure to remove the solvent, after which 68 g of diisopropyl ether was added for crystallization. The resulting solid was filtered, rinsed with diisopropyl ether, and dried at 40° C. under reduced pressure, obtaining 5.7 g (yield 61%) of the target iodonium salt I-2.

$^1$H-NMR (500 MHz, DMSO-$d_6$):

δ=6.36 (1H, s), 7.40 (2H, m), 7.52 (2H, m), 7.65 (1H, m), 8.24 (2H, m), 8.31 (2H, m) ppm $^{19}$F-NMR (500 MHz, DMSO-$d_6$):

δ=−108.3 (1F, m), −74.6 (6F, s) ppm

TOFMS (MALDI)

Positive M$^+$ 299 (corresponding to $C_{12}H_9FI^+$)

Negative M$^-$ 211 (corresponding to $C_4HF_6O_3^-$)

Example 1-3

Synthesis of Iodonium Salt 1-3

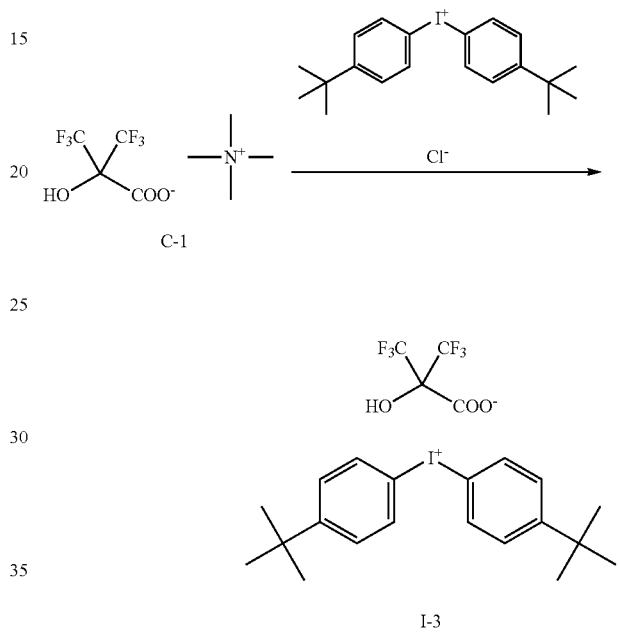

I-3

After 4.3 g of bis(4-tert-butylphenyl)phenyliodonium chloride, 8.1 g of the aqueous solution of anion intermediate C-1, 50 g of methylene chloride, and 20 g of deionized water were mixed and stirred for 1 hour, the organic layer was taken out. The procedure of adding 0.67 g of the aqueous solution of anion intermediate C-1 and 10 g of deionized water to the organic layer, stirring the mixture, and taking out the organic layer was repeated 3 times. The organic layer was further washed 5 times with 10 g of deionized water. The organic layer was concentrated under reduced pressure to remove the solvent, after which 60 g of diisopropyl ether was added for crystallization. The resulting solid was filtered, rinsed with diisopropyl ether, and dried at 45° C. under reduced pressure, obtaining 5.9 g (yield 97%) of the target iodonium salt I-3.

$^1$H-NMR (500 MHz, DMSO-$d_6$):

δ=1.25 (18H, s), 6.34 (1H, s), 7.53 (4H, m), 8.14 (4H, m) ppm $^{19}$F-NMR (500 MHz, DMSO-$d_6$):

δ=−74.6 (6F, s) ppm

TOFMS (MALDI)

Positive M$^+$ 393 (corresponding to $C_{20}H_{26}I^+$)

Negative M$^-$ 211 (corresponding to $C_4HF_6O_3^-$)

Example 1-4

Synthesis of Iodonium Salt I-4

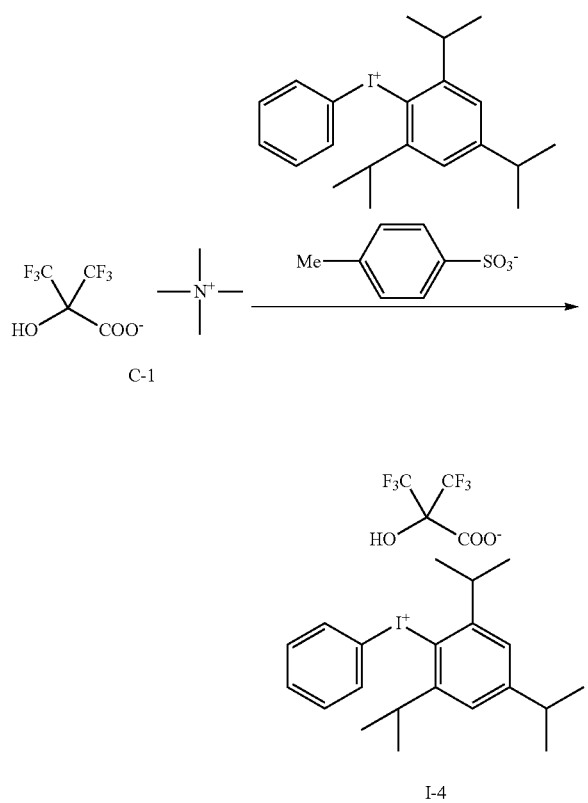

After 8.7 g of phenyl[2,4,6-tris(1-methylethyl)phenyl] iodonium p-toluenesulfonate (known compound), 11.1 g of the aqueous solution of anion intermediate C-1, 40 g of methylene chloride, and 10 g of deionized water were mixed and stirred for 1 hour, the organic layer was taken out. The procedure of adding 1.0 g of the aqueous solution of anion intermediate C-1 and 20 g of deionized water to the organic layer, stilling the mixture, and taking out the organic layer was repeated 7 times. The organic layer was further washed 5 times with 20 g of deionized water. The organic layer was concentrated under reduced pressure to remove the solvent, after which 60 g of tert-butyl methyl ether was added for crystallization. The resulting solid was filtered, rinsed with tert-butyl methyl ether, and dried at 50° C. under reduced pressure, obtaining 4.9 g (yield 52%) of the target iodonium salt I-4.

$^1$H-NMR (500 MHz, DMSO-$d_6$):

δ=1.20 (6H, d), 1.21 (12H, d), 2.96 (1H, m), 3.37 (2H, m), 6.38 (1H, s), 7.30 (2H, s), 7.52 (2H, m), 7.62 (1H, m), 7.91 (2H, m) ppm $^{19}$F-NMR (500 MHz, DMSO-$d_6$):

δ=−74.6 (6F, s) ppm

TOFMS (MALDI)

Positive M$^+$ 407 (corresponding to $C_{21}H_{28}I^+$)

Negative M$^−$ 211 (corresponding to $C_4HF_6O_3^−$)

Example 1-5

Synthesis of Iodonium Salt 1-5

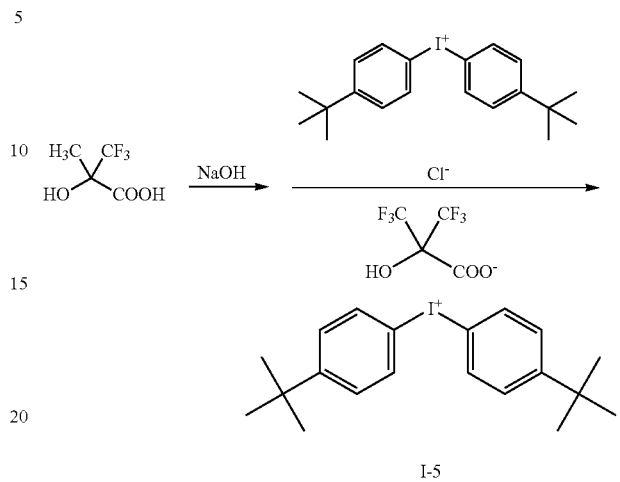

A flask was charged with 7.9 g of 3,3,3-trifluoro-2-hydroxy-2-methylpropionic acid and 34.1 g of deionized water. With stirring and under ice cooling, 8.0 g of a 25 wt % aqueous solution of sodium hydroxide was added drop wise. At the end of addition, stirring was continued at room temperature for 20 minutes, obtaining an aqueous solution of sodium 3,3,3-trifluoro-2-hydroxy-2-methylpropionate (concentration 1 mmol/g, referred to as aqueous solution A, hereinafter). Then 4.3 g of bis(4-tert-butylphenyl)iodonium chloride, 40 g of methylene chloride, and 30 g of aqueous solution A were mixed and stirred for 30 minutes, after which the organic layer was taken out. The procedure of adding 10 g of aqueous solution A to the organic layer, stirring the mixture, and taking out the organic layer was repeated twice. The organic layer was further washed 4 times with 15 of deionized water. The organic layer was concentrated under reduced pressure to remove the methylene chloride while a solid precipitated. The solid precipitate was dispersed in 30 g of diisopropyl ether, stirred for 1 hour, filtered, and rinsed with diisopropyl ether. The resulting solid was dried at 50° C. under reduced pressure, obtaining 4.9 g (yield 88%) of the target iodonium salt I-5.

$^1$H-NMR (500 MHz, DMSO-$d_6$):

δ=1.19 (3H, s), 1.24 (18H, s), 5.59 (1H, s), 7.51 (4H, m), 8.13 (4H, m) ppm $^{19}$F-NMR (500 MHz, DMSO-$d_6$):

δ=−78.5 (3F, s) ppm

TOFMS (MALDI)

Positive M$^+$ 393 (corresponding to $C_{20}H_{26}I^+$)

Negative M$^−$ 157 (corresponding to $C_4H_4F_3O_3^−$)

Examples 1-6 to 1-12

Synthesis of Iodonium Salts I-6 to I-12

By repeating the same procedure as in Examples aside from replacing the starting ester (methyl 3,3,3-trifluoro-2-hydroxy-2-(trifluoromethyl)propionate) or the starting carboxylic acid (3,3,3-trifluoro-2-hydroxy-2-methylpropionic acid) by a corresponding ester or carboxylic acid and using a corresponding iodonium cation, iodonium salts I-6 to I-12 as shown below were obtained. The starting anion and cation materials may be commercially available products or synthesized by well-known methods prior to use.

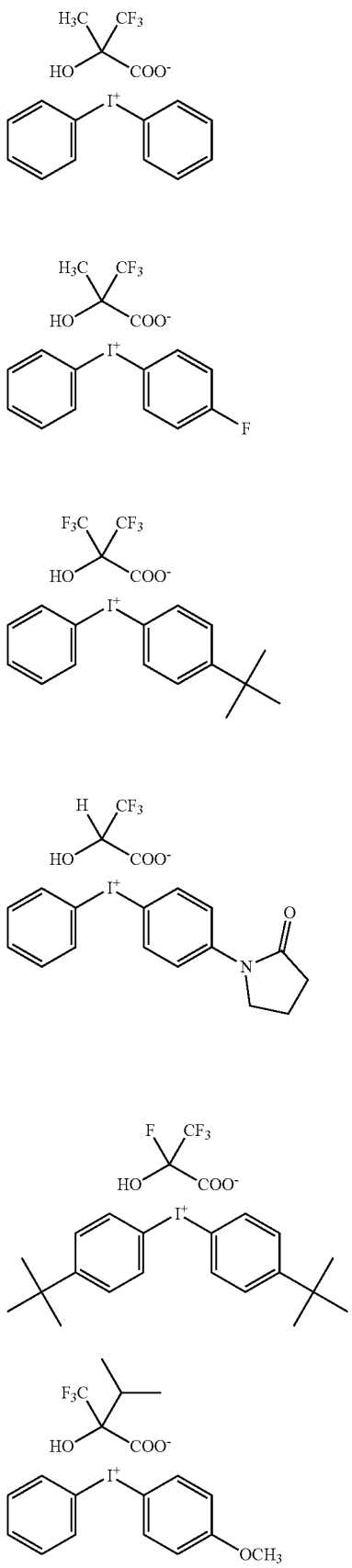

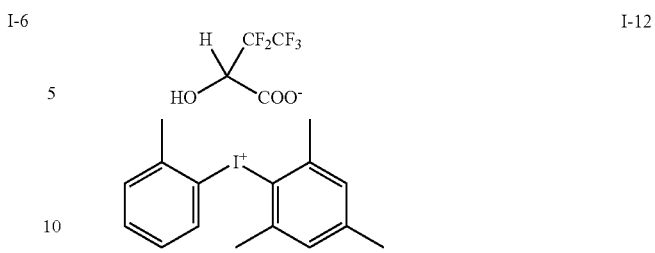

[3] Synthesis of Base Resins

Synthesis Example 2-1

Synthesis of Polymer P-1

In a flask under nitrogen atmosphere, 22 g of 1-tert-butylcyclopentyl methacrylate, 17 g of 2-oxotetrahydrofuran-3-yl methacrylate, 0.48 g of dimethyl 2,2'-azobis(2-methyl-propionate) (V-601 by Wako Pure Chemical Industries, Ltd.). 0.41 g of 2-mercaptoethanol, and 50 g of methyl ethyl ketone were combined to form a monomer/initiator solution. Another flask in nitrogen atmosphere was charged with 23 g of methyl ethyl ketone, which was heated at 80° C. with stirring. With stirring, the monomer/initiator solution was added dropwise to the flask over 4 hours. After the completion of dropwise addition, the polymerization solution was continuously stirred for 2 hours while maintaining the temperature of 80° C. The polymerization solution was cooled to room temperature, whereupon it was added dropwise to 640 g of methanol with vigorous stirring. The precipitate was collected by filtration, washed twice with 240 g of methanol, and vacuum dried at 50° C. for 20 hours, obtaining 36 g of Polymer P-1 in white powder form (yield 90%). On GPC analysis, Polymer P-1 had a Mw of 8,200 and a dispersity Mw/Mn of 1.63.

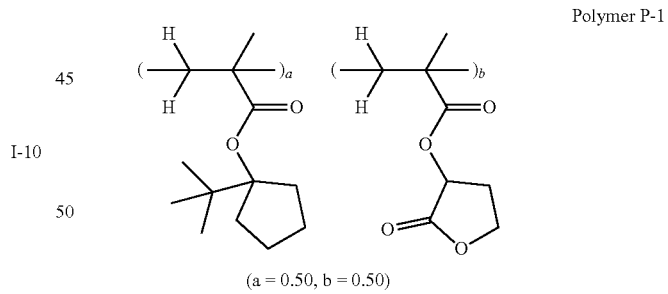

Polymer P-1

(a = 0.50, b = 0.50)

Synthesis Examples 2-2 to 2-10

Synthesis of Polymers P-2 to P-10

Polymers P-2 to P-10 were synthesized by the same procedure as in Synthesis Example 2-1 aside from changing the type and amount of monomers.

The composition of Polymers P-1 to P-10 is shown in Table 1. Table 1 shows the molar ratio of units incorporated in the polymers, and Tables 2 to 4 show the structure of recurring units.

TABLE 1
| Polymer | Unit 1 (ratio) | Unit 2 (ratio) | Unit 3 (ratio) | Unit 4 (ratio) | Mw | Mw/Mn |
|---|---|---|---|---|---|---|
| P-1 | A-1 (0.50) | B-1 (0.50) | — | — | 8,200 | 1.63 |
| P-2 | A-1 (0.45) | B-2 (0.50) | B-4 (0.05) | — | 7,700 | 1.69 |
| P-3 | A-1 (0.45) | B-1 (0.35) | B-3 (0.15) | B-4 (0.05) | 8,300 | 1.75 |
| P-4 | A-2 (0.10) | A-3 (0.40) | B-1 (0.25) | B-3 (0.25) | 8,200 | 1.68 |
| P-5 | A-2 (0.05) | A-3 (0.40) | B-2 (0.30) | B-3 (0.25) | 8,900 | 1.80 |
| P-6 | A-1 (0.45) | A-2 (0.05) | B-3 (0.40) | B-4 (0.10) | 10,000 | 1.88 |
| P-7 | A-1 (0.30) | A-4 (0.20) | B-3 (0.10) | B-5 (0.40) | 9,500 | 1.90 |
| P-8 | A-1 (0.50) | A-2 (0.10) | B-5 (0.30) | C-1 (0.10) | 11,000 | 1.85 |
| P-9 | A-2 (0.10) | A-3 (0.55) | B-5 (0.25) | C-2 (0.10) | 10,500 | 1.82 |
| P-10 | A-1 (0.60) | B-5 (0.30) | C-3 (0.10) | — | 10,800 | 1.79 |
TABLE 2
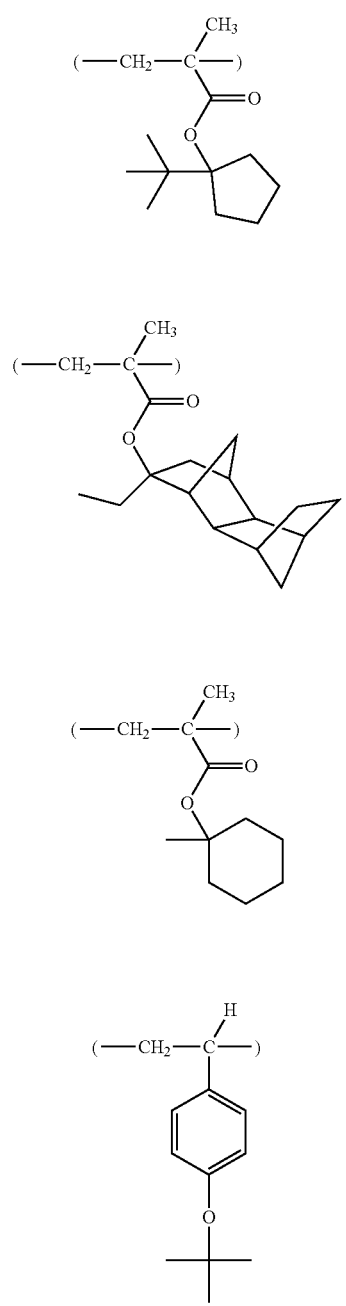
TABLE 3
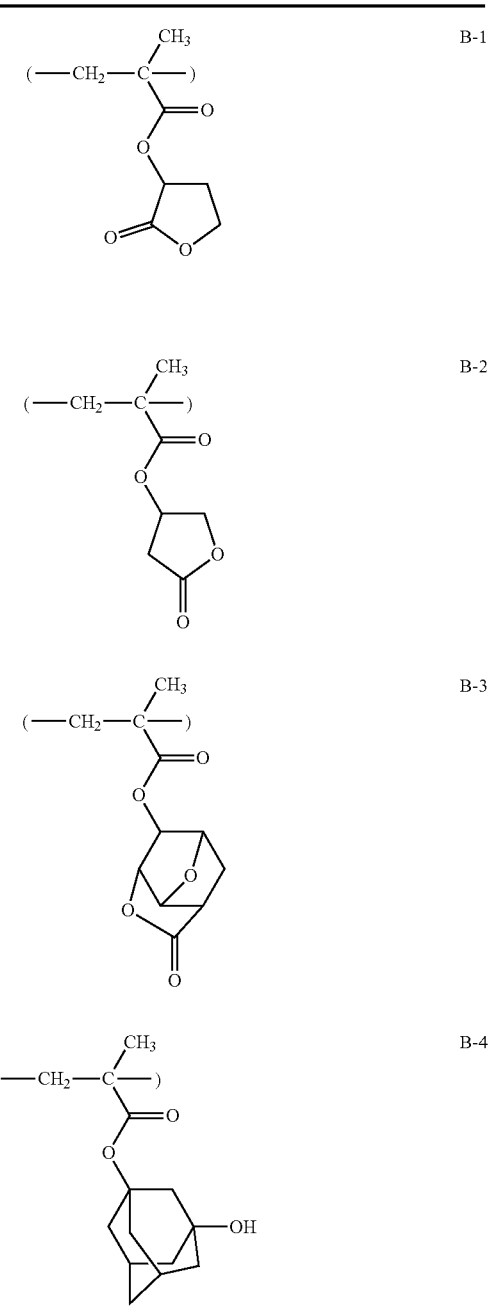

TABLE 3-continued

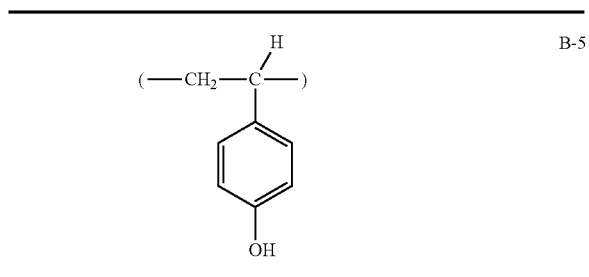
B-5

TABLE 4

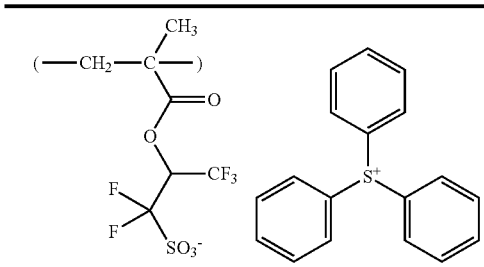 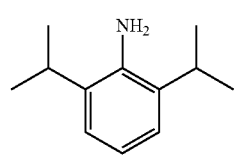
C-1

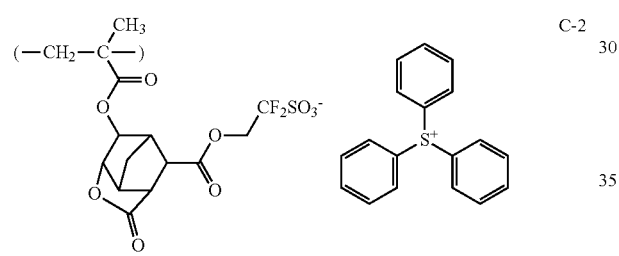 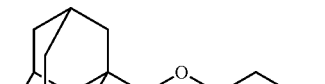
C-2

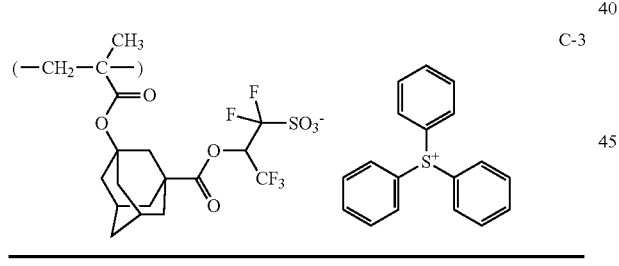 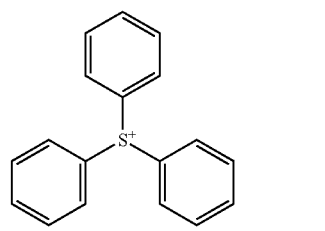
C-3

[4] Preparation of Resist Composition

Examples 2-1 to 2-24 and Comparative Examples 1-1 to 1-12

Resist compositions in solution form were prepared by dissolving an iodonium salt (1-1 to 1-12), polymer (P-1 to P-10), photoacid generator (PAG-A to PAG-C), quencher (Q-1 to Q-8), and alkali-soluble surfactant SF-1 in a solvent containing 0.01 wt % of surfactant A in accordance with the formulation shown in Tables 5 and 6, and filtering through a Teflon® filter with a pore size of 0.2 µm.

The quenchers Q-1 to Q-8, solvents, photoacid generators PAG-A to PAG-C, and alkali-soluble surfactant SF-1 in Tables 5 and 6 are identified below.

Quencher:

Q-1: 1-(tert-butoxycarbonyl)-4-hydroxypiperidine

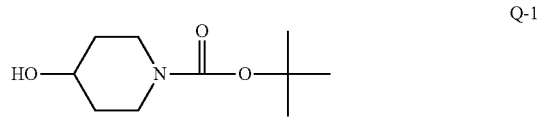
Q-1

Q-2: 2,6-diisopropylaniline

Q-2

Q-3: triphenylsulfonium 2-[(adamantane-1-carbonyl)oxy]ethylsulfonate

Q-3

Q-4: diphenyl iodonium-2-carboxylate

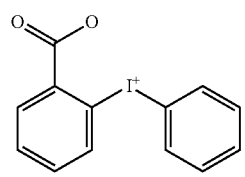
Q-4

Q-5: triphenylsulfonium 3,3,3-trifluoro-2-hydroxy-2-trifluoromethylpropionate

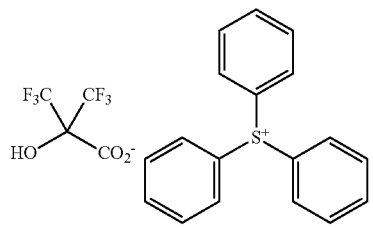

Q-6: bis(4-tert-butylphenyl)phenylsulfonium 3,3,3-trifluoro-2-hydroxy-2-trifluoromethylpropionate

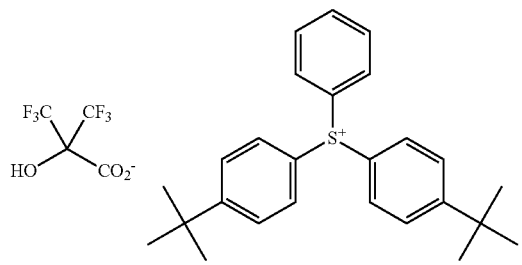

Q-7: triphenylsulfonium adamantanecarboxylate

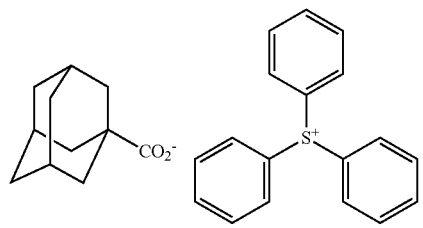

Q-8: triphenylsulfonium salicylate

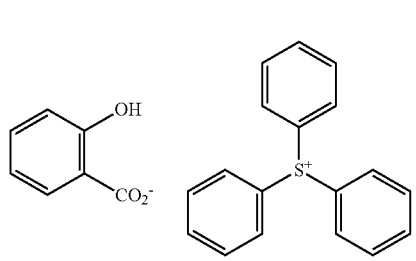

Solvent:
PGMEA=propylene glycol monomethyl ether acetate
GBL=γ-butyrolactone

Photoacid Generator:

PAG-A: triphenylsulfonium 2-[(adamantane-1-carbonyl)oxy]-1,1,3,3,3-pentafluoropropane-1-sulfonate

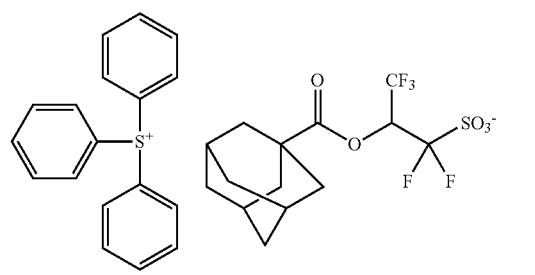

PAG-B: triphenylsulfonium 2-[(adamantane-1-carbonyl)oxy]-2-trifluoromethyl-3,3,3,-trifluoropropane-1-sulfonate

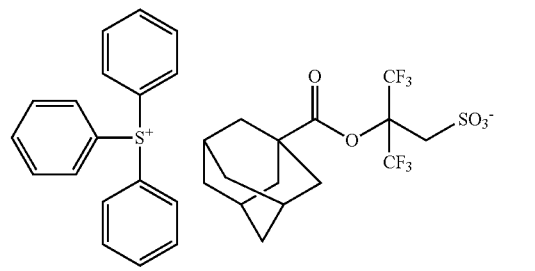

PAG-C: 4-[(2-methoxyethoxy)naphthalene]-1-tetrahydrothiophenium 2-[(adamantane-1-carbonyl)oxy]-1,1-difluoroethanesulfonate

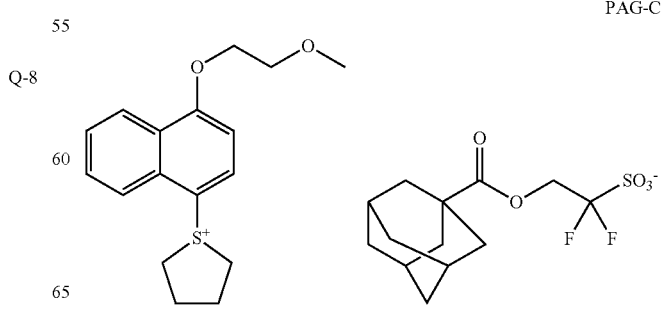

Alkali-Soluble Surfactant SF-1:

poly(2,2,3,3,4,4,4-heptafluoro-1-isobutyl-1-butyl methacrylate/9-(2,2,2-trifluoro-1-trifluoroethyloxy-carbonyl)-4-oxatricyclo[4.2.1.0$^{3,7}$]nonan-5-on-2-yl methacrylate)

Mw=7,700

Mw/Mn=1.82

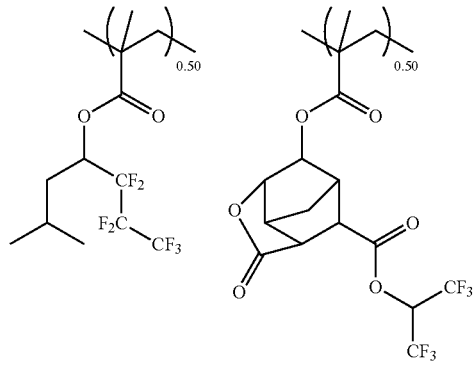

Surfactant A:

3-methyl-3-(2,2,2-trifluoroethoxymethyl)oxetane/ tetrahydrofuran/2,2-dimethyl-1,3-propane Diol Copolymer (Onmova Solutions, Inc.)

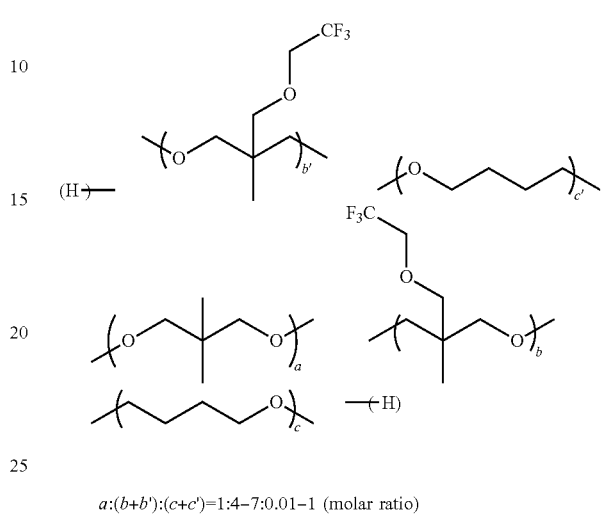

$a:(b+b'):(c+c')=1:4-7:0.01-1$ (molar ratio)

Mw=1,500

TABLE 5

|  |  | Resist composition | Polymer (pbw) | Acid generator (pbw) | Quencher (pbw) | Surfactant (pbw) | Solvent 1 (pbw) | Solvent 2 (pbw) |
|---|---|---|---|---|---|---|---|---|
| Example | 2-1 | R-1 | P-1 (80) | PAG-A (7.0) | I-1 (6.0) | SF-1 (3.0) | PGMEA (1,536) | GBL (384) |
|  | 2-2 | R-2 | P-2 (80) | PAG-A (8.0) | I-2 (5.0) | SF-1 (3.0) | PGMEA (1,536) | GBL (384) |
|  | 2-3 | R-3 | P-3 (80) | PAG-A (8.0) | I-3 (4.0) | SF-1 (3.0) | PGMEA (1,536) | GBL (384) |
|  | 2-4 | R-4 | P-4 (80) | PAG-A (6.0) PAG-B (2.0) | I-4 (4.0) | SF-1 (3.0) | PGMEA (1,536) | GBL (384) |
|  | 2-5 | R-5 | P-5 (80) | PAG-C (8.0) | I-5 (3.0) Q-1 (1.5) | SF-1 (3.0) | PGMEA (1,536) | GBL (384) |
|  | 2-6 | R-6 | P-6 (80) | PAG-A (8.0) | I-1 (5.0) | SF-1 (3.0) | PGMEA (1,536) | GBL (384) |
|  | 2-7 | R-7 | P-7 (80) | PAG-A (7.0) PAG-B (2.0) | I-2 (3.5) Q-3 (2.0) | SF-1 (3.0) | PGMEA (1,536) | GBL (384) |
|  | 2-8 | R-8 | P-8 (80) | — | I-1 (4.0) | SF-1 (3.0) | PGMEA (1,536) | GBL (384) |
|  | 2-9 | R-9 | P-9 (80) | PAG-A (6.0) | I-3 (5.0) Q-2 (2.0) | SF-1 (3.0) | PGMEA (1,536) | GBL (384) |
|  | 2-10 | R-10 | P-10 (80) | — | I-2 (4.0) | SF-1 (3.0) | PGMEA (1,536) | GBL (384) |
|  | 2-11 | R-11 | P-1 (80) | PAG-A (7.0) | I-2 (6.0) | SF-1 (3.0) | PGMEA (1,536) | GBL (384) |
|  | 2-12 | R-12 | P-1 (80) | PAG-A (7.0) | I-3 (5.0) | SF-1 (3.0) | PGMEA (1,536) | GBL (384) |
|  | 2-13 | R-13 | P-1 (80) | PAG-A (7.0) | I-4 (6.0) | SF-1 (3.0) | PGMEA (1,536) | GBL (384) |
|  | 2-14 | R-14 | P-1 (80) | PAG-A (7.0) | I-5 (5.0) | SF-1 (3.0) | PGMEA (1,536) | GBL (384) |
|  | 2-15 | R-15 | P-1 (80) | PAG-A (7.0) | I-6 (6.0) | SF-1 (3.0) | PGMEA (1,536) | GBL (384) |
|  | 2-16 | R-16 | P-1 (80) | PAG-A (7.0) | I-7 (6.0) | SF-1 (3.0) | PGMEA (1,536) | GBL (384) |
|  | 2-17 | R-17 | P-1 (80) | PAG-A (7.0) | I-8 (6.0) | SF-1 (3.0) | PGMEA (1,536) | GBL (384) |
|  | 2-18 | R-18 | P-1 (80) | PAG-A (7.0) | I-9 (4.5) | SF-1 (3.0) | PGMEA (1,536) | GBL (384) |
|  | 2-19 | R-19 | P-1 (80) | PAG-A (7.0) | I-10 (5.0) | SF-1 (3.0) | PGMEA (1,536) | GBL (384) |
|  | 2-20 | R-20 | P-1 (80) | PAG-A (7.0) | I-11 (6.0) | SF-1 (3.0) | PGMEA (1,536) | GBL (384) |
|  | 2-21 | R-21 | P-1 (80) | PAG-A (7.0) | I-12 (6.0) | SF-1 (3.0) | PGMEA (1,536) | GBL (384) |
|  | 2-22 | R-22 | P-8 (80) | — | I-2 (4.0) | SF-1 (3.0) | PGMEA (1,536) | GBL (384) |
|  | 2-23 | R-23 | P-8 (80) | — | I-3 (3.5) | SF-1 (3.0) | PGMEA (1,536) | GBL (384) |
|  | 2-24 | R-24 | P-8 (80) | — | I-5 (3.5) | SF-1 (3.0) | PGMEA (1,536) | GBL (384) |

TABLE 6

|  |  | Resist composition | Polymer (pbw) | Acid generator (pbw) | Quencher (pbw) | Surfact (pbw) | Solvent 1 (pbw) | Solvent 2 (pbw) |
|---|---|---|---|---|---|---|---|---|
| Comparative Example | 1-1 | R-25 | P-1 (80) | PAG-A (7.0) | Q-1 (6.0) | SF-1 (3.0) | PGMEA (1,536) | GBL (384) |
|  | 1-2 | R-26 | P-1 (80) | PAG-A (7.0) | Q-3 (6.0) | SF-1 (3.0) | PGMEA (1,336) | GBL (384) |
|  | 1-3 | R-27 | P-1 (80) | PAG-A (7.0) | Q-4 (6.0) | SF-1 (3.0) | PGMEA (1,536) | GBL (384) |

TABLE 6-continued

| Resist composition | Polymer (pbw) | Acid generator (pbw) | Quencher (pbw) | Surfact (pbw) | Solvent 1 (pbw) | Solvent 2 (pbw) |
|---|---|---|---|---|---|---|
| 1-4 R-28 | P-1 (80) | PAG-A (7.0) | Q-5 (6.0) | SF-1 (3.0) | PGMEA (1,536) | GBL (384) |
| 1-5 R-29 | P-1 (80) | PAG-A (7.0) | Q-5 (5.0) | SF-1 (3.0) | PGMEA (1,536) | GBL (384) |
| 1-6 R-30 | P-1 (80) | PAG-A (7.0) | Q-7 (6.0) | SF-1 (3.0) | PGMEA (1,536) | GBL (384) |
| 1-7 R-31 | P-1 (80) | PAG-A (7.0) | Q-8 (6.0) | SF-1 (3.0) | PGMEA (1,536) | GBL (384) |
| 1-8 R-32 | P-8 (80) | — | Q-2 (4.0) | SF-1 (3.0) | PGMEA (1,536) | GBL (384) |
| 1-9 R-33 | P-8 (80) | — | Q-5 (4.0) | SF-1 (3.0) | PGMEA (1,536) | GBL (384) |
| 1-10 R-34 | P-8 (80) | — | Q-6 (3.5) | SF-1 (3.0) | PGMEA (1,536) | GBL (384) |
| 1-11 R-35 | P-8 (80) | — | Q-7 (4.0) | SF-1 (3.0) | PGMEA (1,536) | GBL (384) |
| 1-12 R-36 | P-8 (80) | — | Q-8 (4.0) | SF-1 (3.0) | PGMEA (1,536) | GBL (384) |

[5] ArF Lithography Test #1: Evaluation of Hole Pattern

Examples 3-1 to 3-18 and Comparative Examples 2-1 to 2-7

On a substrate, a spin-on carbon film ODL-101 (Shin-Etsu Chemical Co., Ltd.) was deposited to a thickness of 200 nm and a silicon-containing spin-on hard mask SHB-A940 (Shin-Etsu Chemical Co., Ltd.) having a silicon content of 43 wt % was deposited thereon to a thickness of 35 nm. On this substrate for trilayer process, each of the resist compositions (R-1 to R-7, R-11 to R-$21$) and comparative resist compositions (R-25 to R-31) was spin coated, then baked on a hotplate at 100° C. for 60 seconds to form a resist film of 100 nm thick.

Using an ArF excimer laser immersion lithography stepper (NSR-610C by Nikon Corp., NA 1.30, σ 0.98/0.78, dipole opening 20 deg., azimuthally polarized illumination, dipole illumination, 6% halftone phase shift mask), live resist film was exposed through a first mask having X-axis direction lines with a pitch of 80 nm and a width of 40 nm (on-wafer size) and then through a second mask having Y-axis direction lines with a pitch of 80 nm and a width of 40 nm (on-wafer size). Water was used as the immersion liquid. After exposure, the resist film was baked (PEB) at the temperature shown in Table 7 for 60 seconds and developed. Specifically, butyl acetate was injected from a development nozzle for 3 seconds while the wafer was spun at 30 rpm, which was followed by stationary puddle development for 27 seconds.

Evaluation of Sensitivity

The hole pattern thus formed was observed under an electron microscope CD-SEM (CG-5000 by Hitachi High-Technologies Corp.). The optimum dose (Eop) is a dose (mJ/cm$^2$) which provides a hole pattern having a diameter of 40 nm at a pitch of 80 nm.

Evaluation of Mask Error Factor (MEF)

A pattern was formed by exposure in the optimum dose Eop (determined in the sensitivity evaluation) through a mask with the pitch fixed and the line width varied. MEF was calculated from variations of the mask line width and the pattern space width according to the following equation:

MEF=(pattern space width)/(mask line width)-$b$ wherein b is a constant. A value closer to unity (1) indicates better performance.

Evaluation of Critical Dimension Uniformity (CDU)

The hole pattern printed as above was observed under CD-SEM (CG-5000 by Hitachi High-Technologies Corp.), and 125 holes were measured for diameter. A three-fold value (3σ) of a standard variation (σ) was computed therefrom as a variation of hole size and reported as CDU. A smaller value (3σ) indicates a better CDU.

The results are shown in Table 7.

TABLE 7

| | | Resist composition | PEB temp. (° C.) | Eop (mJ/cm$^2$) | MEF | CDU (nm) |
|---|---|---|---|---|---|---|
| Example | 3-1 | R-1 | 85 | 35 | 3.1 | 3.4 |
| | 3-2 | R-2 | 85 | 34 | 3.2 | 3.4 |
| | 3-3 | R-3 | 85 | 39 | 2.9 | 3.1 |
| | 3-4 | R-4 | 90 | 38 | 3.3 | 3.6 |
| | 3-5 | R-5 | 90 | 40 | 3.3 | 3.5 |
| | 3-6 | R-6 | 85 | 35 | 3.2 | 3.6 |
| | 3-7 | R-7 | 90 | 43 | 3.4 | 3.5 |
| | 3-8 | R-11 | 85 | 35 | 3.1 | 3.3 |
| | 3-9 | R-12 | 85 | 39 | 3.3 | 3.4 |
| | 3-10 | R-13 | 85 | 38 | 3.1 | 3.5 |
| | 3-11 | R-14 | 85 | 41 | 3.0 | 3.2 |
| | 3-12 | R-15 | 85 | 37 | 3.2 | 3.3 |
| | 3-13 | R-16 | 85 | 36 | 3.2 | 3.2 |
| | 3-14 | R-17 | 85 | 39 | 3.3 | 3.5 |
| | 3-15 | R-18 | 90 | 45 | 3.2 | 3.3 |
| | 3-16 | R-19 | 85 | 40 | 3.0 | 3.2 |
| | 3-17 | R-20 | 85 | 39 | 3.2 | 3.5 |
| | 3-18 | R-21 | 90 | 42 | 3.5 | 3.6 |
| Comparative Example | 2-1 | R-25 | 85 | 37 | 4.5 | 4.2 |
| | 2-2 | R-26 | 85 | 42 | 4.1 | 4.0 |
| | 2-3 | R-27 | 85 | 37 | 3.7 | 3.9 |
| | 2-4 | R-28 | 85 | 34 | 3.6 | 4.0 |
| | 2-5 | R-29 | 85 | 39 | 3.5 | 3.8 |
| | 2-6 | R-30 | 85 | 40 | 3.6 | 4.1 |
| | 2-7 | R-31 | 85 | 39 | 3.6 | 4.2 |

It is evident from Table 7 that when a hole pattern is formed from the inventive resist composition via organic solvent development, MEF and CDU are improved. This suggests that the inventive resist composition is suited for the organic solvent development process.

[6] ArF Lithography Patterning Test #2: Evaluation of L/S Pattern

Examples 4-1 to 4-24 and Comparative Examples 3-1 to 3-12

On a substrate, a spin-on carbon film ODL-101 (Shin-Etsu Chemical Co., Ltd.) was deposited to a thickness of 200 mm and a silicon-containing spin-on hard mask SHB-A940 (Shin-Etsu Chemical Co., Ltd.) having a silicon content of 43 wt % was deposited thereon to a thickness of 35 nm. On this substrate for trilayer process, each of the inventive resist compositions (R-1 to R-24) and comparative resist compositions (R-25 to R-36) was spin coated and baked on a hotplate at 100° C. for 60 seconds to form a resist film of 100 nm thick.

Using an ArF excimer laser immersion lithography scanner NSR-610C (Nikon Corp., NA 1.30, σ 0.98/0.78, 4/5 annular illumination), pattern exposure was performed through a 6% halftone phase shift mask bearing a pattern with a pitch of 100 nm and a space width of 50 mu (on-wafer size). Water was used as the immersion liquid. After exposure, die wafer was baked (PEB) at the temperature shown in Table 8 for 60 seconds and developed. Specifically. 2.38 wt % TMAH aqueous solution was injected from a development nozzle for 3 seconds while the wafer was spun at 30 rpm, which was followed by stationary puddle development for 27 seconds. As a result, the exposed regions of the resist film were dissolved in the developer to form a line-and-space (US) pattern with a space width of 50 nm and a pitch of 100 nm.

Evaluation of Sensitivity

The US pattern was observed under an electron microscope CD-SEM (CG-5000). As an index of sensitivity, the optimum dose Eop (mJ/cm²) which provided a US pattern with a space width of 50 nm and a pitch of 100 nm was determined.

Evaluation of MEF

A pattern was formed by exposure in the optimum dose Eop (determined in the sensitivity evaluation) through a mask with the pitch fixed and the line width varied. MEF was calculated from variations of the mask line width and the pattern space width according to the following equation:

MEF=(pattern space width)/(mask line width)−b wherein b is a constant. A value closer to unity (1) indicates better performance.

Evaluation of LWR

The L/S pattern formed by exposure in the optimum dose Eop was observed under CD-SEM (CG-5000). The space width was measured at longitudinally spaced apart 10 points, from which a 3-fold value (3σ) of standard deviation (σ) was determined and reported as LWR. A smaller value of 3σ indicates a pattern having a lower roughness and more uniform space width.

Evaluation of Profile

The L/S pattern formed by exposure in the optimum dose Eop was observed under CD-SEM (CG-5000). The pattern was rated "OK" when the patient profile was rectangular and the sidewalls were substantially perpendicular, or "NG" when the pattern had a tapered profile with noticeably graded sidewalls or a top rounded profile due to top loss.

The results are shown in Table 8.

TABLE 8

|  |  | Resist composition | PEB temp. (° C.) | Eop (mJ/cm²) | MEF | LWR (nm) | Profile |
|---|---|---|---|---|---|---|---|
| Example | 4-1 | R-1 | 85 | 35 | 3.3 | 2.4 | OK |
|  | 4-2 | R-2 | 85 | 34 | 3.4 | 2.4 | OK |
|  | 4-3 | R-3 | 85 | 38 | 3.2 | 2.5 | OK |
|  | 4-4 | R-4 | 90 | 38 | 3.6 | 2.6 | OK |
|  | 4-5 | R-5 | 90 | 40 | 3.5 | 2.5 | OK |
|  | 4-6 | R-6 | 85 | 35 | 3.5 | 2.6 | OK |
|  | 4-7 | R-7 | 90 | 42 | 3.7 | 2.7 | OK |
|  | 4-8 | R-8 | 90 | 30 | 3.0 | 2.3 | OK |
|  | 4-9 | R-9 | 95 | 31 | 3.1 | 2.3 | OK |
|  | 4-10 | R-10 | 90 | 31 | 2.9 | 7.7 | OK |
|  | 4-11 | R-11 | 85 | 35 | 3.4 | 2.5 | OK |
|  | 4-12 | R-12 | 85 | 39 | 3.5 | 2.5 | OK |
|  | 4-13 | R-13 | 85 | 39 | 3.4 | 2.7 | OK |
|  | 4-14 | R-14 | 85 | 41 | 3.3 | 2.6 | OK |
|  | 4-15 | R-15 | 85 | 37 | 3.5 | 2.7 | OK |
|  | 4-16 | R-16 | 85 | 36 | 3.4 | 7.7 | OK |
|  | 4-17 | R-17 | 85 | 38 | 3.5 | 2.6 | OK |
|  | 4-18 | R-18 | 90 | 45 | 3.5 | 2.7 | OK |
|  | 4-19 | R-19 | 85 | 40 | 3.2 | 2.7 | OK |
|  | 4-20 | R-20 | 85 | 38 | 3.4 | 2.6 | OK |
|  | 4-21 | R-21 | 90 | 41 | 3.7 | 2.6 | OK |
|  | 4-22 | R-22 | 90 | 30 | 3.1 | 2.2 | OK |
|  | 4-23 | R-23 | 95 | 32 | 2.9 | 2.4 | OK |
|  | 4-24 | R-24 | 90 | 31 | 3.0 | 2.3 | OK |
| Comparative Example | 3-1 | R-25 | 85 | 37 | 4.8 | 3.8 | NG |
|  | 3-2 | R-26 | 85 | 42 | 4.3 | 3.6 | NG |
|  | 3-3 | R-27 | 85 | 37 | 3.9 | 3.3 | NG |
|  | 3-4 | R-28 | 85 | 35 | 3.8 | 3.0 | NG |
|  | 3-5 | R-29 | 85 | 39 | 3.8 | 2.9 | NG |
|  | 3-6 | R-30 | 85 | 40 | 3.9 | 3.3 | NG |
|  | 3-7 | R-31 | 85 | 38 | 3.9 | 3.3 | NG |
|  | 3-8 | R-32 | 90 | 36 | 3.8 | 2.9 | NG |
|  | 3-9 | R-33 | 90 | 31 | 3.5 | 2.7 | NG |
|  | 3-10 | R-34 | 95 | 33 | 3.6 | 2.6 | NG |
|  | 3-11 | R-35 | 90 | 34 | 3.6 | 2.8 | NG |
|  | 3-12 | R-36 | 90 | 33 | 3.6 | 2.8 | NG |

It is evident from Table 8 that the inventive resist composition is improved in profile (rectangularity), MEF and LWR upon positive pattern formation via alkaline aqueous solution development. This suggests that the inventive resist composition is suited for the alkaline aqueous solution development process.

[7] EB Lithography Test: Evaluation of L/S Pattern

Examples 5-1 to 5-7 and Comparative Examples 4-1 to 4-5

A silicon substrate was coated with an antireflective coating of 60 nm thick (DUV-42, Nissan Chemical Corp.). Each of the inventive resist compositions (R-7 to R-10, R-22 to R-24) and comparative resist compositions (R-32 to R-36)

was spin coated on the substrate and prebaked on a hotplate at 105° C. for 60 seconds to form a resist film of 50 nm thick. The resist film was exposed to EB using an EB lithography system ELS-F125 (Elionix Co., Ltd., accelerating voltage 125 kV). The resist film was baked (PEB) on a hotplate at the temperature shown in Table 9 for 60 seconds. The resist film was then developed in a 2.38 wt % TMAH aqueous solution for 30 seconds. The resist film in the exposed regions was dissolved in the developer to form a positive resist pattern which was a L/S pattern having a space width of 45 nm and a pitch 90 nm.

Evaluation of Sensitivity

The L/S pattern was observed under an electron microscope CD-SEM (S-9380. Hitachi High-Technologies Corp.). As an index of sensitivity, the optimum dose Fop (µC/cm$^2$) which provided a L/S pattern with a space width of 50 nm and a pitch of 90 nm was determined.

Evaluation of LWR

The L/S pattern formed by exposure in the optimum dose Eop was observed under CD-SEM (S-9380). The space width was measured at longitudinally spaced apart 10 points, from which a 3-fold value (3σ) of standard deviation (σ) was determined and reported as LWR. A smaller value of 3σ indicates a pattern having a lower roughness and more uniform space width.

Evaluation of Profile

The L/S pattern formed by exposure in the optimum dose Eop was observed under CD-SEM (S-9380). The pattern was rated "OK" when the pattern profile was rectangular and the sidewalls were substantially perpendicular, or "NG" when the pattern had a tapered profile with noticeably graded sidewalls or a top rounded profile due to top loss.

The results are shown in Table 9.

TABLE 9

|  |  | Resist composition | PEB temp (° C.) | Eop (µC/cm$^2$) | LWR (nm) | Profile |
|---|---|---|---|---|---|---|
| Example |  | 5-1 R-7 | 100 | 330 | 3.5 | OK |
|  |  | 5-2 R-8 | 90 | 270 | 3.4 | OK |
|  |  | 5-3 R-9 | 95 | 280 | 3.5 | OK |
|  |  | 5-4 R-10 | 90 | 260 | 3.3 | OK |
|  |  | 5-5 R-22 | 90 | 260 | 3.4 | OK |
|  |  | 5-6 R-23 | 95 | 280 | 3.3 | OK |
|  |  | 5-7 R-24 | 90 | 280 | 3.5 | OK |
| Comparative Example |  | 4-1 R-32 | 90 | 360 | 3.9 | NG |
|  |  | 4-2 R-33 | 90 | 300 | 3.8 | NG |
|  |  | 4-3 R-34 | 95 | 320 | 3.7 | NG |
|  |  | 4-4 R-35 | 90 | 330 | 3.9 | NG |
|  |  | 4-5 R-36 | 90 | 320 | 3.7 | NG |

It is evident from Table 9 that the inventive resist composition is improved in sensitivity, profile (rectangularity), and LWR upon positive pattern formation by EB lithography via alkaline aqueous solution development. In Examples 5-1 to 5-7, EB was used for exposure of the resist films. It is generally known that even when radiation of short wavelength such as EUV is used, similar basic resist properties are obtainable, that is, the EB lithography test and the EUV lithography test are correlated. It is thus estimated that the inventive resist composition is improved in sensitivity, profile, and LWR when processed by the EUV lithography.

Japanese Patent Application No. 2018-169547 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A resist composition comprising
   a quencher comprising an iodonium salt having the formula (1), and
   a base resin consisting of recurring units having the formula (a) and recurring units having the formula (b) and optionally recurring units of at least one type selected from recurring units having the formulae (c1) to (c4):

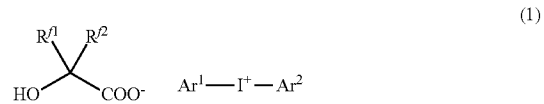

(1)

wherein $R^{f1}$ and $R^{f2}$ are each independently hydrogen, fluorine, or a $C_1$-$C_4$ straight or branched monovalent hydrocarbon group which may contain fluorine, at least one of $R^{f1}$ and $R^{f2}$ being fluorine or a $C_1$-$C_4$ straight or branched monovalent hydrocarbon group which may contain fluorine, $Ar^1$ and $Ar^2$ are each independently a $C_6$-$C_{40}$ aryl group which may contain a heteroatom, or $Ar^1$ and $Ar^2$ may bond together to form a ring with the iodine atom to which they are attached, and

(a)

(b)

wherein $R^A$ is hydrogen, fluorine, methyl or trifluoromethyl, $Z^A$ is a single bond, phenylene, naphthylene or (backbone)-C(=O)-O-Z'-, Z' is a $C_1$-$C_{10}$ alkanediyl group which may contain a hydroxyl moiety, ether bond, ester bond or lactone ring, or phenylene or naphthylene, $X^A$ is an acid labile group, and $Y^A$ is hydrogen or a polar group containing at least one structure selected from the group consisting of hydroxyl, cyano, carbonyl, carboxyl, ether bond, ester bond, sulfonic acid ester bond, carbonate bond, lactone ring, sultone ring and carboxylic anhydride,

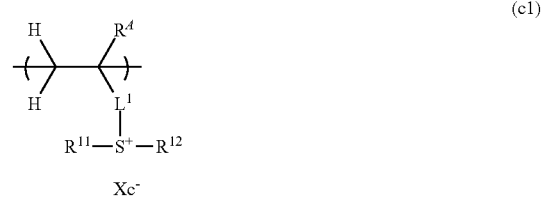

(c1)

-continued

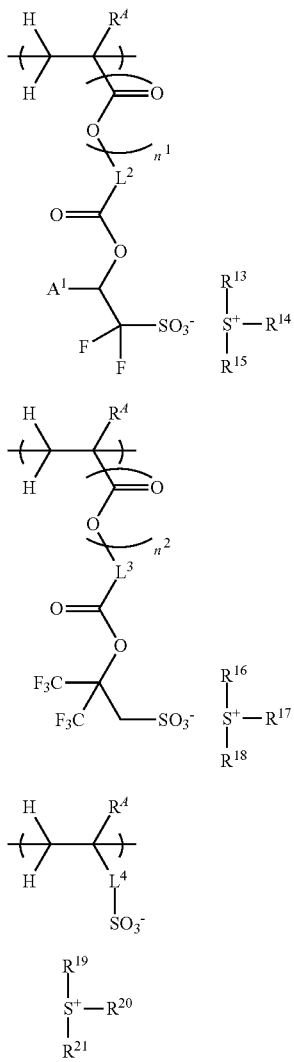

(c2)

(c3)

(c4)

wherein $R^A$ is hydrogen, fluorine, methyl or trifluoromethyl,
$L^1$ is a single bond, phenylene, —O-$L^{11}$-, —C(=O)—O-$L^{11}$- or —C(=O)—NH-$L^{11}$-, $L^{11}$ is a $C_1$-$C_{20}$ alkanediyl group, $C_2$-$C_{20}$ alkenediyl group or phenylene group, which may contain a heteroatom,
$L^2$ and $L^3$ are each independently a single bond or a $C_1$-$C_{20}$ divalent hydrocarbon group which may contain a heteroatom,
$L^4$ is a single bond, methylene, ethylene, phenylene, fluorinated phenylene, —O-$L^{41}$-, —C(=O)—O-$L^{41}$- or —C(=O)—NH-$L^{41}$-, $L^{41}$ is an optionally substituted phenylene group,
$R^{11}$ to $R^{21}$ are each independently a $C_1$-$C_{20}$ monovalent hydrocarbon group which may contain a heteroatom, any two of $L^1$, $R^{11}$ and $R^{12}$ may bond together to form a ring with the sulfur atom to which they are attached, any two of $R^{13}$, $R^{14}$ and $R^{15}$, any two of $R^{16}$, $R^{17}$ and $R^{18}$, or any two of $R^{19}$, $R^{20}$ and $R^{21}$ may bond together to form a ring with the sulfur atom to which they are attached,
$Xc^-$ is a non-nucleophilic counter ion,
$A^1$ is hydrogen or trifluoromethyl,
$n^1$ is 0 or 1, $n^1$ is 0 when $L^2$ is a single bond, $n^2$ is 0 or 1, $n^2$ is 0 when $L^3$ is a single bond.

2. The resist composition of claim 1, further comprising an organic solvent.

3. The resist composition of claim 1, further comprising a photoacid generator.

4. The resist composition of claim 3 wherein the photoacid generator has the formula (2) or (3):

$$R^{102}-\underset{R^{103}}{\overset{R^{101}}{S^+}}\quad X^- \tag{2}$$

wherein $R^{101}$, $R^{102}$ and $R^{103}$ are each independently a $C_1$-$C_{20}$ monovalent hydrocarbon group which may contain a heteroatom, any two of $R^{101}$, $R^{102}$ and $R^{103}$ may bond together to form a ring with the sulfur atom to which they are attached, and $X^-$ is an anion selected from the following formulae (2A) to (2D):

$$R^{fa}-CF_2-SO_3^- \tag{2A}$$

$$\begin{array}{c} R^{fb1}-CF_2-SO_2 \\ \phantom{R^{fb1}-CF_2-SO_2}\diagdown \\ \phantom{R^{fb1}-CF_2-SO_2-}N^- \\ \phantom{R^{fb1}-CF_2-SO_2}\diagup \\ R^{fb2}-CF_2-SO_2 \end{array} \tag{2B}$$

$$R^{fc1}-CF_2-SO_2-\underset{\underset{\underset{R^{fc3}}{\mid}}{\underset{\mid}{CF_2}}}{\underset{\mid}{\overset{\mid}{\underset{SO_2}{\mid}}}}\overset{\overset{\overset{R^{fc2}}{\mid}}{\overset{\mid}{CF_2}}}{\overset{\mid}{\underset{SO_2}{\mid}}}C^- \tag{2C}$$

$$R^{fd}-\overset{O}{\overset{\|}{C}}-O-\underset{\underset{CF_3}{\mid}}{\overset{\overset{CF_3}{\mid}}{C}}-CH_2-SO_3^- \tag{2D}$$

wherein $R^{fa}$, $R^{fb1}$, $R^{fb2}$, $R^{fc1}$, $R^{fc2}$ and $R^{fc3}$ are each independently fluorine or a $C_1$-$C_{40}$ monovalent hydrocarbon group which may contain a heteroatom, or a pair of $R^{fb1}$ and $R^{fb2}$, or $R^{fc1}$ and $R^{fc2}$ may bond together to form a ring with the carbon atom to which they are attached and any intervening atoms, $R^{fd}$ is a $C_1$-$C_{40}$ monovalent hydrocarbon group which may contain a heteroatom, $$R^{201}-\underset{R^{202}}{\overset{}{S^+}}-R^{203}-L^A-\underset{\underset{X^2}{\mid}}{\overset{\overset{X^3}{\mid}}{C}}-\underset{\underset{X^2}{\mid}}{\overset{\overset{X^1}{\mid}}{C}}-SO_3^- \tag{3}$$

wherein $R^{201}$ and $R^{202}$ are each independently a $C_1$-$C_{30}$ monovalent hydrocarbon group which may contain a heteroatom, $R^{203}$ is a $C_1$-$C_{30}$ divalent hydrocarbon group which may contain a heteroatom, any two of $R^{201}$, $R^{202}$ and $R^{203}$ may bond together to form a ring with the sulfur atom to which they are attached, $L^A$ is a single bond, ether bond or a $C_1$-$C_{20}$ divalent hydrocarbon group which may contain a heteroatom, $X^1$, $X^2$, $X^3$ and $X^4$ are each independently hydrogen, fluorine or trifluoromethyl, at least one of $X^1$, $X^2$, $X^3$ and $X^4$ is fluorine or trifluoromethyl.

5. The resist composition of claim 1, further comprising an amine compound.

6. The resist composition of claim 1, further comprising a surfactant which is insoluble or substantially insoluble in water and soluble in alkaline developer, and/or a surfactant which is insoluble or substantially insoluble in water and alkaline developer.

7. A pattern forming process comprising the steps of applying the resist composition of claim 1 onto a substrate to form a resist film, exposing a selected region of the resist film to KrF excimer laser, ArF excimer laser, EB or EUV, and developing the exposed resist film in a developer.

8. The pattern forming process of claim 7 wherein the developing step uses an alkaline aqueous solution as the developer, thereby forming a positive pattern in which an exposed region of the resist film is dissolved away and an unexposed region of the resist film is not dissolved.

9. The pattern forming process of claim 7 wherein the developing step uses an organic solvent as the developer, thereby forming a negative pattern in which an unexposed region of the resist film is dissolved away and an exposed region of the resist film is not dissolved.

10. The pattern forming process of claim 9 wherein the organic solvent is at least one solvent selected from the group consisting of 2-octanone, 2-nonanone, 2-heptanone, 3-heptanone, 4-heptanone, 2-hexanone, 3-hexanone, diisobutyl ketone, methylcyclohexanone, acetophenone, methylacetophenone, propyl acetate, butyl acetate, isobutyl acetate, pentyl acetate, butenyl acetate, isopentyl acetate, propyl formate, butyl formate, isobutyl formate, pentyl formate, isopentyl formate, methyl valerate, methyl pentenoate, methyl crotonate, ethyl crotonate, methyl propionate, ethyl propionate, ethyl 3-ethoxypropionate, methyl lactate, ethyl lactate, propyl lactate, butyl lactate, isobutyl lactate, pentyl lactate, isopentyl lactate, methyl 2-hydroxyisobutyrate, ethyl 2-hydroxyisobutyrate, methyl benzoate, ethyl benzoate, phenyl acetate, benzyl acetate, methyl phenylacetate, benzyl formate, phenylethyl formate, methyl 3-phenylpropionate, benzyl propionate, ethyl phenylacetate, and 2-phenylethyl acetate.

11. The process of claim 7 wherein the exposure step is carried out by immersion lithography while a liquid having a refractive index of at least 1.0 is held between the resist film and a projection lens.

12. The process of claim 11, further comprising the step of coating a protective film on the resist film prior to the exposure step,
wherein immersion lithography is carried out while the liquid is held between the protective film and the projection lens.

* * * * *